(12) United States Patent
Tsuyama et al.

(10) Patent No.: US 10,270,043 B2
(45) Date of Patent: Apr. 23, 2019

(54) ORGANIC TRANSISTOR, COMPOUND, ORGANIC SEMICONDUCTOR MATERIAL FOR NON-LIGHT-EMITTING ORGANIC SEMICONDUCTOR DEVICE, MATERIAL FOR ORGANIC TRANSISTOR, COATING SOLUTION FOR NON-LIGHT-EMITTING ORGANIC SEMICONDUCTOR DEVICE, METHOD FOR MANUFACTURING ORGANIC TRANSISTOR, METHOD FOR MANUFACTURING ORGANIC SEMICONDUCTOR FILM, ORGANIC SEMICONDUCTOR FILM FOR NON-LIGHT-EMITTING ORGANIC SEMICONDUCTOR DEVICE, AND METHOD FOR SYNTHESIZING ORGANIC SEMICONDUCTOR MATERIAL

(71) Applicants: FUJIFILM Corporation, Tokyo (JP); The University of Tokyo, Tokyo (JP)

(72) Inventors: Hiroaki Tsuyama, Kanagawa (JP); Kimiatsu Nomura, Kanagawa (JP); Yoshihisa Usami, Kanagawa (JP); Eiji Fukuzaki, Kanagawa (JP); Masashi Koyanagi, Kanagawa (JP); Tetsu Kitamura, Kanagawa (JP); Tetsuya Watanabe, Kanagawa (JP); Toshihiro Okamoto, Tokyo (JP); Junichi Takeya, Tokyo (JP)

(73) Assignees: FUJIFILM Corporation, Tokyo (JP); The University of Tokyo, Tokyo (JP)

(*) Notice: Subject to any disclaimer, the term of this patent is extended or adjusted under 35 U.S.C. 154(b) by 45 days.

(21) Appl. No.: 15/274,062

(22) Filed: Sep. 23, 2016

(65) Prior Publication Data
US 2017/0018724 A1 Jan. 19, 2017

Related U.S. Application Data

(63) Continuation of application No. PCT/JP2015/059297, filed on Mar. 26, 2015.

(30) Foreign Application Priority Data

Mar. 26, 2014 (JP) .................. 2014-063111
Mar. 12, 2015 (JP) .................. 2015-049036

(51) Int. Cl.
*H01L 51/00* (2006.01)
*C07D 493/14* (2006.01)
(Continued)

(52) U.S. Cl.
CPC ........ *H01L 51/0074* (2013.01); *C07D 493/14* (2013.01); *C07D 495/14* (2013.01);
(Continued)

(58) Field of Classification Search
CPC .................................................. H01L 51/0071
See application file for complete search history.

(56) References Cited

U.S. PATENT DOCUMENTS

| 2014/0319473 | A1* | 10/2014 | Lee ..................... H01L 51/0052 257/40 |
| 2017/0012220 | A1* | 1/2017 | Tsuyama ............. H01L 51/0074 |
| 2018/0226589 | A1* | 8/2018 | Tsuyama ............. H01L 51/0074 |

FOREIGN PATENT DOCUMENTS

| CN | 102206225 A | 10/2011 |
| JP | S63-180960 A | 7/1988 |

(Continued)

OTHER PUBLICATIONS

Wex, B., et al. "End-capping of conjugated thiophene-benzene aromatic systems." Tetrahedron. vol. 66 (2010), pp. 8778-8784.*

(Continued)

*Primary Examiner* — Andrew D Kosar
*Assistant Examiner* — John S Kenyon
(74) *Attorney, Agent, or Firm* — Studebaker & Brackett PC

(57) ABSTRACT

Provided are an organic transistor with high carrier mobility having a semiconductor active layer containing a compound which is represented by the following formula and has a molecular weight of equal to or less than 3,000, a compound, an organic semiconductor material for a non-light-emitting organic semiconductor device, a material for an organic transistor, a coating solution for a non-light-emitting organic semiconductor device, a method for manufacturing an organic transistor, a method for manufacturing an organic semiconductor film, an organic semiconductor film for a non-light-emitting organic semiconductor device, and a method for manufacturing an organic semiconductor material.

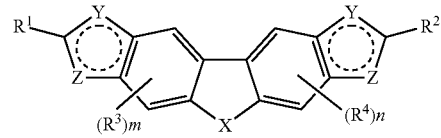

(X represents an oxygen, sulfur, selenium, or tellurium atom or $NR^5$; Y and Z each represents $CR^6$, an oxygen, sulfur, selenium, or nitrogen atom, or $NR^7$; a ring containing Y and Z is an aromatic heterocycle; any one of $R^1$ and $R^2$ and the aromatic heterocycle containing Y and Z or any one of $R^3$ and $R^4$ and a benzene ring may be bonded to each other through a specific divalent linking group; $R^1$, $R^2$, and $R^5$ to $R^8$ each represent a hydrogen atom, an alkyl group, an alkenyl group, an alkynyl group, an aryl group, or a heteroaryl group; $R^3$ and $R^4$ each represent an alkyl group, an alkenyl group, an alkynyl group, an aryl group, or heteroaryl group; and each of m and n is an integer of 0 to 2).

23 Claims, 5 Drawing Sheets

(51) Int. Cl.
| | |
|---|---|
| C07D 495/14 | (2006.01) |
| C07D 497/14 | (2006.01) |
| C07D 513/14 | (2006.01) |
| C07D 517/14 | (2006.01) |
| C07D 519/00 | (2006.01) |
| C09D 5/24 | (2006.01) |
| C09B 57/00 | (2006.01) |
| H01L 51/05 | (2006.01) |

(52) U.S. Cl.
CPC ......... *C07D 497/14* (2013.01); *C07D 513/14* (2013.01); *C07D 517/14* (2013.01); *C07D 519/00* (2013.01); *C09B 57/00* (2013.01); *C09D 5/24* (2013.01); *H01L 51/0068* (2013.01); *H01L 51/0071* (2013.01); *H01L 51/0003* (2013.01); *H01L 51/0545* (2013.01); *H01L 51/0558* (2013.01); *Y02E 10/549* (2013.01); *Y02P 70/521* (2015.11)

(56) References Cited

FOREIGN PATENT DOCUMENTS

| | | | |
|---|---|---|---|
| JP | 2010-045281 A | | 2/2010 |
| JP | 2013-235903 A | | 11/2013 |
| WO | 2011/126225 A1 | | 10/2011 |
| WO | WO-2018061821 A1 | * | 4/2018 |

OTHER PUBLICATIONS

Sureshbabu, R., et al. "Lewis Acid Mediated One-Pot Synthesis of Aryl/Heteroaryl-Fused Carbazoles Involving a Cascade Friedel-Crafts Alkylation/Electrocyclization/Aromatization Reaction Sequence." Eur. J. Org. Chem. (2011), pp. 922-935.*

Wex, B., et al. "End-capping of conjugated thiophene-benzene aromatic systems." Tetrahedron. (2010), vol. 66, pp. 8778-8784.*
International Preliminary Report on Patentability (Chapter I) and Translation of Written Opinion of the International Searching Authority; PCT/JP2015/059297; dated Sep. 27, 20165.
International Search Report and Written Opinion issued in PCT/JP2015/059297; dated Apr. 28, 2015.
Wex et al.; End-capping of conjugated thiophene-benzene aromatic systems; Tetrahedron; 2010 ; pp. 8778-8784.
Holiday et al.; Advances in Charge Carrier Mobilities of Semiconducting Polymers Used in Organic Transistors; Chemistry of Materials; 2014 ; pp. 647-663.
Wex et al.; Synthesis of the anti and syn Isomers of Thieno[f,f']bis[1]benzothiophene. Comparison of the Optical and Electrochemical Properties of the anti and syn Isomers1; J. Org. Chem.; 2005; pp. 4502-4505.
The extended European search report issued by the European Patent Office dated Mar. 1, 2017, which corresponds to European Patent Application No. 15770420.6-1555 and is related to U.S. Appl. No. 15/274,062; 9pp.
Wex et al.; "End-capping of conjugated thiophene-benzene aromatic systems"; Tetrahedron, Elsevier Science Publishers; Amsterdam, NL; vol. 66; No. 45; Nov. 6, 2010; pp. 8778-8784.
Radhakrishnan et al.; "Lewis Acid Mediated One-Pot Synthesis of Aryll Heteroaryl-Fused Carbazoles Involving a Cascade Friedel-Crafts Alkylation\Electrocyclization\Aromatization Reaction Sequence"; European Journal of Organic Chemistry; vol. 2011; No. 5; Dec. 22, 2010; pp. 922-935.
An Office Action; "Notification of Reasons for Refusal," issued by the Korean Patent Office dated Jan. 11, 2018, which corresponds to Korean Patent Application No. 10-2016-7026434 and is related to U.S. Appl. No. 15/274,062; with English language translation.
An Office Action issued by the Chinese Patent Office (SIPO) dated Sep. 29, 2018, which corresponds to Chinese Patent Application No. 201580014491.8 and is related to U.S. Appl. No. 15/274,062; with English language translation.

* cited by examiner

ORGANIC TRANSISTOR, COMPOUND, ORGANIC SEMICONDUCTOR MATERIAL FOR NON-LIGHT-EMITTING ORGANIC SEMICONDUCTOR DEVICE, MATERIAL FOR ORGANIC TRANSISTOR, COATING SOLUTION FOR NON-LIGHT-EMITTING ORGANIC SEMICONDUCTOR DEVICE, METHOD FOR MANUFACTURING ORGANIC TRANSISTOR, METHOD FOR MANUFACTURING ORGANIC SEMICONDUCTOR FILM, ORGANIC SEMICONDUCTOR FILM FOR NON-LIGHT-EMITTING ORGANIC SEMICONDUCTOR DEVICE, AND METHOD FOR SYNTHESIZING ORGANIC SEMICONDUCTOR MATERIAL

CROSS-REFERENCE TO RELATED APPLICATIONS

This application is a Continuation of PCT International Application No. PCT/JP2015/059297, filed on Mar. 26, 2015, which claims priority under 35 U.S.C. Section 119(a) to Japanese Patent Application No. 2014-063111 filed on Mar. 26, 2014 and Japanese Patent Application No. 2015-049036 filed on Mar. 12, 2015. Each of the above applications is hereby expressly incorporated by reference, in its entirety, into the present application.

BACKGROUND OF THE INVENTION

1. Field of the Invention

The present invention relates to a compound, an organic semiconductor material for a non-light-emitting organic semiconductor device, a material for an organic transistor, a coating solution for a non-light-emitting organic semiconductor device, a method for manufacturing an organic transistor, a method for manufacturing an organic semiconductor film, an organic semiconductor film for a non-light-emitting organic semiconductor device, and a method for synthesizing an organic semiconductor material. Specifically, the present invention relates to a compound having a fused-ring skeletal structure, an organic transistor containing the compound, an organic semiconductor material for a non-light-emitting organic semiconductor device containing the compound, a material for an organic transistor containing the compound, a coating solution for a non-light-emitting organic semiconductor device containing the compound, a method for manufacturing an organic semiconductor film using the compound, a method for manufacturing an organic transistor using the coating solution for a non-light-emitting organic semiconductor device, an organic semiconductor film for a non-light-emitting organic semiconductor device containing the compound, and a method for synthesizing an organic semiconductor material.

2. Description of the Related Art

Devices using organic semiconductor materials are drawing great attention because they are expected to be superior in various aspects to devices using inorganic semiconductor materials of the related art such as silicon. Examples of the devices using organic semiconductor materials include a photoelectric conversion element such as an organic thin-film solar cell or a solid-state imaging element using organic semiconductor materials as photoelectric conversion materials, an organic transistor (referred to as an organic thin-film transistor in some cases) having non-light-emitting properties (in the present specification, "non-light-emitting" refers to properties by which a luminous efficiency of equal to or less than 1 lm/W is obtained in a case where electric currents are applied to a device at a current density of 0.1 mW/cm$^2$ at room temperature in the atmosphere; non-light-emitting organic semiconductor devices mean organic semiconductor devices excluding light-emitting organic semiconductor devices such as organic electroluminescence elements), and the like. Compared to the devices using inorganic semiconductor materials, the devices using organic semiconductor materials are likely to make it possible to prepare large area elements at lower temperature and lower costs. Furthermore, the characteristics of the materials can be easily changed by varying the molecular structure thereof. Therefore, the materials show a wide variation and can realize functions or elements that cannot be obtained by inorganic semiconductor materials.

Regarding organic semiconductor materials, the use of compounds having a fused-ring skeletal structure in a semiconductor active layer is examined so as to improve carrier mobility and to improve transistor performances.

For example, CN102206225A describes an organic semiconductor polymer having a fused-ring skeletal structure and a low-molecular weight compound used for synthesizing the organic semiconductor polymer having a fused-ring skeletal structure. In CN102206225A, carrier mobility obtained at the time when the organic semiconductor polymer having a fused-ring skeletal structure is applied to an organic transistor is examined.

Meanwhile, a case is known where a compound having a fused-ring skeletal structure similar to the organic semiconductor polymer having a fused-ring skeletal structure described in CN102206225A is used in an element other than an organic transistor. For example, JP2013-235903A describes a case where an organic semiconductor polymer having a fused-ring skeletal structure is used in a photoelectric conversion layer of an organic thin-film solar cell.

A case is also known where a low-molecular weight compound having a fused-ring skeletal structure similar to the organic semiconductor polymer having a fused-ring skeletal structure described in CN102206225A is used. For example, JP2010-045281A describes an organic electroluminescence element material containing a compound which has, as a partial structure, a fused ring consisting of five aromatic rings having a chalcogen atom-containing aromatic heterocycle as one of the constituents. Furthermore, WO2011/126225A discloses, as a novel compound for an organic electronic material, a compound having a fused-ring skeletal structure consisting of five rings, and discloses a case where the compound is used in an organic electroluminescence element.

JP1988-180960A (JP-S63-180960A) discloses an example of an electrophotographic photoreceptor containing, as a photoconductor, a disazo pigment having a fused-ring skeletal structure.

In addition, Tetrahedron 66 (2010) 8778-8784 discloses a method for synthesizing a compound C6-TBBT or C12-TBBT obtained by substituting thieno[3,2-f:4,5-f']bis[1]benzothiophene (hereinafter referred to as TBBT as well) with an alkyl group having 6 carbon atoms or an alkyl group having 12 carbon atoms respectively, and discloses absorption/emission spectra and cyclic voltammetry (CV) as physical properties thereof. Although Tetrahedron 66 (2010) 8778-8784 describes the application of the compound to an organic transistor in the introduction part of the document, it does not describe the evaluation of organic transistor characteristics such as mobility.

SUMMARY OF THE INVENTION

Under the circumstances described above, the inventors of the present invention examined organic transistors using the compounds described in CN102206225A, JP2013-235903A, WO2011/126225A, JP1988-180960A (JP-S63-180960A), and Tetrahedron 66 (2010) 8778-8784. As a result, the inventors found that the organic transistors have low carrier mobility.

Therefore, in order to solve the problem of the related art described above, the inventors of the present invention continued examination. An object of the present invention is to provide an organic transistor having high carrier mobility.

As a result of conducting intensive examination for achieving the above object, the inventors obtained knowledge that, by substituting a skeleton having a specific fused-ring structure consisting of five rings with a specific substituent, an organic transistor having high carrier mobility can be obtained. Based on the knowledge, the inventors accomplished the present invention.

The present invention as specific means for achieving the above object has the following constitution.

[1] An organic transistor comprising a semiconductor active layer which is represented by the following Formula (1) and has a molecular weight of equal to or less than 3,000;

Formula (1)

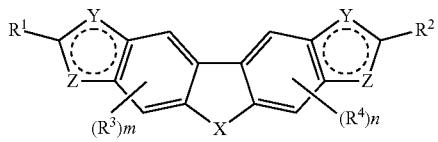

in Formula (1),

X represents an oxygen atom, a sulfur atom, a selenium atom, a tellurium atom, or $NR^5$;

Y and Z each independently represent $CR^6$, an oxygen atom, a sulfur atom, a selenium atom, a nitrogen atom, or $NR^7$, two Y's may be the same as or different from each other, and two Z's may be the same as or different from each other;

a ring containing Y and Z is an aromatic heterocycle;

any one of $R^1$ and $R^2$ and the aromatic heterocycle containing Y and Z may be bonded to each other through the following group A of divalent linking groups;

any one of $R^3$ and $R^4$ and a benzene ring may be bonded to each other through the following group A of divalent linking groups;

the group A of divalent linking groups represents any one of divalent linking groups —O—, —S—, —$NR^8$—, —CO—, —SO—, and —$SO_2$— or represents a divalent linking group in which two or more of these divalent linking groups are bonded to each other;

$R^1$, $R^2$, $R^5$, $R^6$, $R^7$, and $R^8$ each independently represent a hydrogen atom, an alkyl group, an alkenyl group, an alkynyl group, an aryl group, or a heteroaryl group and may further have a substituent;

$R^3$ and $R^4$ each independently represent an alkyl group, an alkenyl group, an alkynyl group, an aryl group, or a heteroaryl group and may further have a substituent, in a case where m is 2, $R^3$'s may be the same as or different from each other, and in a case where n is 2, $R^4$'s may be the same as or different from each other;

m and n each independently represent an integer of 0 to 2;

here, a case where both of Y and Z are $CR^6$ and a case where both of Y and Z are any one of a nitrogen atom and $NR^7$ are excluded;

in a case where X is $NR^5$, Y is $CR^6$, and Z is a sulfur atom, a case where both of $R^1$ and $R^2$ are a hydrogen atom is excluded;

in a case where X is a sulfur atom, Y is CH, Z is a sulfur atom, and both of $R^1$ and $R^2$ are an alkyl group, any one of $R^1$ and $R^2$ and the aromatic heterocycle containing Y and Z are bonded to each other through the group A of divalent linking groups; and a case where both of $R^1$ and $R^2$ are a hydrogen atom, and both of m and n are 0 is excluded.

[2] The organic transistor described in [1], in which in Formula (1), each of the aromatic heterocycles containing Y and Z is preferably independently any one of a thiophene ring, a furan ring, a pyrrole ring, a thiazole ring, and an oxazole ring.

[3] The organic transistor described in [1] or [2], in which in Formula (1), the number of carbon atoms contained in $R^1$, $R^2$, $R^3$, and $R^4$ is preferably equal to or less than 30.

[4] The organic transistor described in any one of [1] to [3], in which in Formula (1), both of m and n are preferably 0.

[5] The organic transistor described in any one of [1] to [4], in which in Formula (1), each of $R^1$ and $R^2$ is preferably independently an alkyl group having 20 or less carbon atoms, an aryl group having 20 or less carbon atoms, or a heteroaryl group having 20 or less carbon atoms.

[6] The organic transistor described in any one of [1] to [5], in which in Formula (1), $R^1$ and $R^2$ are preferably the same as each other, $R^3$ and $R^4$ are preferably the same as each other, and m and n are preferably the same as each other.

[7] The organic transistor described in any one of [1] to [6], in which the compound which is represented by Formula (1) and has a molecular weight of equal to or less than 3,000 is preferably a compound which is represented by the following Formula (2) or (3) and has a molecular weight of equal to or less than 3,000;

Formula (2)

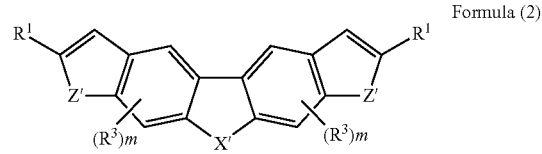

Formula (3)

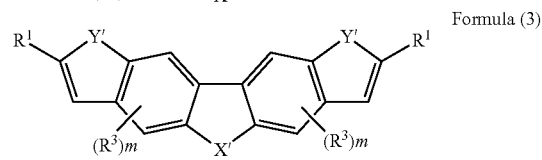

in Formulae (2) and (3), each X' independently represents an oxygen atom, a sulfur atom, or a selenium atom;

each of Y' and Z' is independently selected from $NR^7$, an oxygen atom, a sulfur atom, and a selenium atom;

a ring containing Y' and Z' is an aromatic heterocycle;

$R^1$ and the aromatic heterocycle containing Y' and Z' may be bonded to each other through the following group A of divalent linking groups;

$R^3$ and a benzene ring may be bonded to each other through the following group A of divalent linking groups;

the group A of divalent linking groups represents any one of divalent linking groups —O—, —S—, —NR$^8$—, —CO—, —SO—, and —SO$_2$— or represents a divalent linking group in which two or more of these divalent linking groups are bonded to each other;

R$^1$, R$^7$, and R$^8$ each independently represent a hydrogen atom, an alkyl group, an alkenyl group, an alkynyl group, an aryl group, or a heteroaryl group and may further have a substituent, and two or more R$^1$'s may be the same as or different from each other;

each R$^3$ independently represents an alkyl group, an alkenyl group, an alkynyl group, an aryl group, or a heteroaryl group and may further have a substituent, and in a case where m is 2, R$^3$'s may be the same as or different from each other;

each m is independently an integer of 0 to 2;

here, a case where both of Y' and Z' are NR$^7$ is excluded;

in a case where X', Z', and R$^1$ in Formula (2) are a sulfur atom, a sulfur atom, and an alkyl group respectively, R$^1$ and the aromatic heterocycle containing Z' are bonded to each other through the group A of divalent linking groups; and a case where R$^1$ is a hydrogen atom and all of m's are 0 is excluded.

[8] The organic transistor described in any one of [1] to [7], in which the compound which is represented by Formula (1) and has a molecular weight of equal to or less than 3,000 is preferably a compound which is represented by the following Formula (4) or (5) and has a molecular weight of equal to or less than 3,000;

Formula (4)

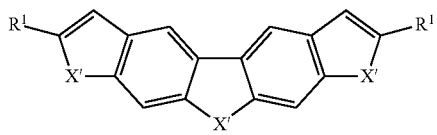

Formula (5)

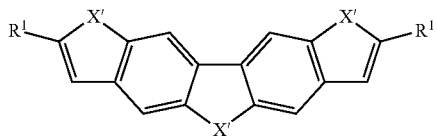

in Formulae (4) and (5), each X' independently represents an oxygen atom, a sulfur atom, or a selenium atom;

R$^1$ and an aromatic heterocycle containing X' may be bonded to each other through the following group A of divalent linking groups;

the group A of divalent linking groups represents any one of divalent linking groups —O—, —S—, —NR$^8$—, —CO—, —SO—, and —SO$_2$— or represents a divalent linking group in which two or more of these divalent linking groups are bonded to each other;

R$^1$ and R$^8$ each independently represent a hydrogen atom, an alkyl group, an alkenyl group, an alkynyl group, an aryl group, or a heteroaryl group and may further have a substituent, and two or more R$^1$'s may be the same as or different from each other;

in a case where all of X's in Formula (4) are a sulfur atom, and R$^1$ in Formula (4) is an alkyl group, R$^1$ and the aromatic heterocycle containing X' are bonded to each other through the group A of divalent linking groups; and a case where R$^1$ is a hydrogen atom is excluded.

[9] The organic transistor described in [8], in which in Formula (4) or (5), R$^1$ preferably has an aliphatic hydrocarbon group.

[10] The organic transistor described in [8] or [9], in which in Formula (4) or (5), R$^1$ is preferably an aryl group having a linear aliphatic hydrocarbon group or a heteroaryl group having a linear aliphatic hydrocarbon group.

[11] A compound which is represented by the following Formula (1A) and has a molecular weight of equal to or less than 3,000;

Formula (1A)

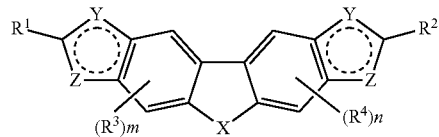

in Formula (1A),

X represents an oxygen atom, a sulfur atom, a selenium atom, a tellurium atom, or NR$^5$;

Y and Z each independently represent CR$^6$, an oxygen atom, a sulfur atom, a selenium atom, a nitrogen atom, or NR$^7$, two Y's may be the same as or different from each other, and two Z's may be the same as or different from each other;

a ring containing Y and Z is an aromatic heterocycle;

any one of R$^1$ and R$^2$ and the aromatic heterocycle containing Y and Z may be bonded to each other through the following group A of divalent linking groups;

any one of R$^3$ and R$^4$ and a benzene ring may be bonded to each other through the following group A of divalent linking groups;

the group A of divalent linking groups represents any one of divalent linking groups —O—, —S—, —NR$^8$—, —CO—, —SO—, and —SO$_2$— or represents a divalent linking group in which two or more of these divalent linking groups are bonded to each other;

R$^1$, R$^2$, R$^5$, R$^6$, R$^7$, and R$^8$ each independently represent a hydrogen atom, an alkyl group, an alkenyl group, an alkynyl group, an aryl group, or a heteroaryl group and may further have a substituent;

R$^3$ and R$^4$ each independently represent an alkyl group, an alkenyl group, an alkynyl group, an aryl group, or a heteroaryl group and may further have a substituent, in a case where m is 2, R$^3$'s may be the same as or different from each other, and in a case where n is 2, R$^4$'s may be the same as or different from each other;

m and n each independently represent an integer of 0 to 2;

here, a case where both of Y and Z are CR$^6$ and a case where both of Y and Z are any one of a nitrogen atom and NR$^7$ are excluded;

a case where X is NR$^5$, Y is a nitrogen atom, and Z is an oxygen atom is excluded;

in a case where X is NR$^5$, Y is CR$^6$, and Z is a sulfur atom, a case where both of R$^1$ and R$^2$ are a hydrogen atom is excluded;

in a case where X is a sulfur atom, Y is CH, Z is a sulfur atom, and both of R$^1$ and R$^2$ are an alkyl group, any one of R$^1$ and R$^2$ and the aromatic heterocycle containing Y and Z are bonded to each other through the group A of divalent linking groups; and a case where both of R¹ and R² are a hydrogen atom, and both of m and n are 0 is excluded.

[12] The compound described in [11], in which in Formula (1A), each of the aromatic heterocycles containing Y and Z is preferably independently any one of a thiophene ring, a furan ring, a pyrrole ring, a thiazole ring, and an oxazole ring.

[13] The compound described in [11] or [12], in which in Formula (1A), the number of carbon atoms contained in IV, R², R³, and R⁴ is preferably equal to or less than 30.

[14] The compound described in any one of [11] to [13], in which in Formula (1A), both of m and n are preferably 0.

[15] The compound described in any one of [11] to [14], in which in Formula (1A), each of R¹ and R² is preferably independently an alkyl group having 20 or less carbon atoms, an aryl group having 20 or less carbon atoms, or a heteroaryl group having 20 or less carbon atoms.

[16] The compound described in any one of [11] to [15], in which in Formula (1A), R¹ and R² are preferably the same as each other, R³ and R⁴ are preferably the same as each other, and m and n are preferably the same as each other.

[17] The compound described in any one of [11] to [16], in which the compound which is represented by Formula (1A) and has a molecular weight of equal to or less than 3,000 is preferably a compound which is represented by the following Formula (2) or (3) and has a molecular weight of equal to or less than 3,000;

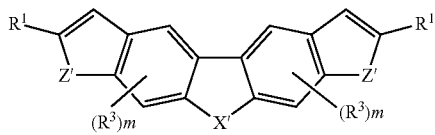

Formula (2)

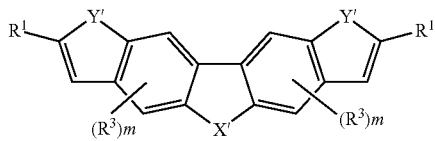

Formula (3)

in Formulae (2) and (3), each X' independently represents an oxygen atom, a sulfur atom, or a selenium atom;

each of Y' and Z' is independently selected from NR⁷, an oxygen atom, a sulfur atom, and a selenium atom;

a ring containing Y' and Z' is an aromatic heterocycle;

R¹ and the aromatic heterocycle containing Y' and Z' may be bonded to each other through the following group A of divalent linking groups;

R³ and a benzene ring may be bonded to each other through the following group A of divalent linking groups;

the group A of divalent linking groups represents any one of divalent linking groups among —O—, —S—, —NR⁸—, —CO—, —SO—, and —SO₂— or represents a divalent linking group in which two or more of these divalent linking groups are bonded to each other;

R¹, R⁷, and R⁸ each independently represent a hydrogen atom, an alkyl group, an alkenyl group, an alkynyl group, an aryl group, or a heteroaryl group and may further have a substituent, and two or more R¹'s may be the same as or different from each other;

each R³ independently represents an alkyl group, an alkenyl group, an alkynyl group, an aryl group, or a heteroaryl group and may further have a substituent, and in a case where m is 2, R³'s may be the same as or different from each other;

each m is independently an integer of 0 to 2;

here, a case where both of Y' and Z' are NR⁷ is excluded;

in a case where X', Z', and R¹ in Formula (2) are a sulfur atom, a sulfur atom, and an alkyl group respectively, R¹ and the aromatic heterocycle containing Z' are bonded to each other through the group A of divalent linking groups; and a case where R¹ is a hydrogen atom and all of m's are 0 is excluded.

[18] The compound described in any one of [11] to [17], in which the compound which is represented by Formula (1A) and has a molecular weight of equal to or less than 3,000 is preferably a compound which is represented by the following Formula (4) or (5) and has a molecular weight of equal to or less than 3,000;

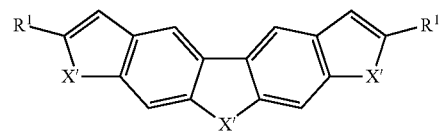

Formula (4)

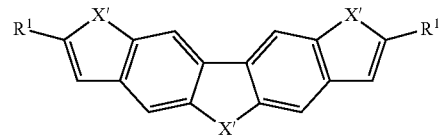

Formula (5)

in Formulae (4) and (5), each X' independently represents an oxygen atom, a sulfur atom, or a selenium atom;

R¹ and an aromatic heterocycle containing X' may be bonded to each other through the following group A of divalent linking groups;

the group A of divalent linking groups represents one of divalent linking groups —O—, —S—, —CO—, —SO—, and —SO₂— or represents a divalent linking group in which two or more of these divalent linking groups are bonded to each other;

R¹ and R⁸ each independently represent a hydrogen atom, an alkyl group, an alkenyl group, an alkynyl group, an aryl group, or a heteroaryl group and may further have a substituent, and two or more R¹'s may be the same as or different from each other;

here, in a case where all of X's in Formula (4) are a sulfur atom, and R¹ in Formula (4) is an alkyl group, R¹ and the aromatic heterocycle containing X' are bonded to each other through the group A of divalent linking groups; and a case where R¹ is a hydrogen atom is excluded.

[19] The compound described in [18], in which in Formula (4) or (5), R¹ preferably has an aliphatic hydrocarbon group.

[20] The compound described in [18] or [19], in which in Formula (4) or (5), R¹ is preferably an aryl group having a linear aliphatic hydrocarbon group or a heteroaryl group having a linear aliphatic hydrocarbon group.

[21] An organic semiconductor material for a non-light-emitting organic semiconductor device containing the compound described in any one of [1] to [10] that is represented by Formula (1) and has a molecular weight of equal to or less than 3,000.

[22] A material for an organic transistor containing the compound described in any one of [1] to [10] that is represented by Formula (1) and has a molecular weight of equal to or less than 3,000.

[23] A coating solution for a non-light-emitting organic semiconductor device containing the compound described in any one of [1] to [10] that is represented by Formula (1) and has a molecular weight of equal to or less than 3,000.

[24] A method for manufacturing an organic transistor, comprising a step of preparing a semiconductor active layer by coating a substrate with the coating solution for a non-light-emitting organic semiconductor device described in [23] and drying the coating solution.

[25] A method for manufacturing an organic semiconductor film, in which in a state where a distance between a substrate A and a member B not being fixed to the substrate A is kept constant or in a state where the substrate A and the member B are caused to remain in contact with each other, a coating solution prepared by dissolving the compound described in any one of [1] to [10] that is represented by Formula (1) and has a molecular weight of equal to or less than 3,000 in a solvent is dropped onto a portion within the surface of the substrate A such that the coating solution contacts both of the substrate A and the member B, and the dropped coating solution is slowly dried, such that crystals of the compound described in any one of [1] to [10] that is represented by Formula (1) and has a molecular weight of equal to or less than 3,000 are precipitated and a semiconductor active layer is formed; here, as long as the distance between the substrate A and the member B is kept constant or as long as the substrate A and the member B are caused to remain in contact with each other, the positional relationship between the substrate A and the member B may be maintained or changed when the coating solution is dropped or dried.

[26] An organic semiconductor film for a non-light-emitting organic semiconductor device containing the compound described in any one of [1] to [10] that is represented by Formula (1) and has a molecular weight of equal to or less than 3,000.

[27] The organic semiconductor film for a non-light-emitting organic semiconductor device described in [26] preferably further containing a polymer binder.

[28] A method for synthesizing an organic semiconductor material, in which a compound represented by the following Formula (6) or (7) is reacted with a compound represented by the following Formula (8) by heating in the presence of a transition metal catalyst and an organic solvent such that the compound described in any one of [1] to [10] that is represented by Formula (1) and has a molecular weight of equal to or less than 3,000 is synthesized;

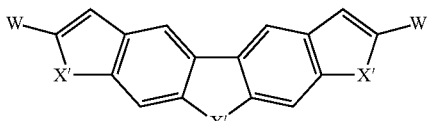

Formula (6)

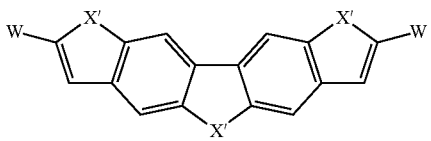

Formula (7)

in Formulae (6) and (7), each X' independently represents an oxygen atom, a sulfur atom, or a selenium atom; and each W independently represents a halogen atom or a perfluoroalkylsulfonyloxy group;

$$R^{11}\text{-}M(R^{12})_i$$ Formula (8)

$R^{11}$ represents an alkyl group, an alkenyl group, an alkynyl group, an aryl group, or a heteroaryl group and may further have a substituent;

M represents magnesium, silicon, boron, tin, or zinc;

each $R^{12}$ independently represents a halogen atom, an alkyl group, an alkenyl group, an alkynyl group, an alkoxy group, or a hydroxyl group, $R^{12}$'s may be the same as or different from each other and may form a ring; and i represents an integer of 1 to 3 and equals a valency of M−1, here, in a case where M is boron, i may be 3.

According to the present invention, it is possible to provide an organic transistor having high carrier mobility.

BRIEF DESCRIPTION OF THE DRAWINGS

FIGS. 3A to 3C are schematic views showing an aspect in which in a state where a distance between a substrate A and a member B not being fixed to the substrate A is kept constant, a coating solution is dropped onto a portion within the surface of the substrate A such that the coating solution contacts both of the substrate A and the member B, and the dropped coating solution is slowly dried in a state where the positional relationship between the substrate A and the member B is maintained.

FIGS. 4A to 4C are schematic views showing another example of the method for manufacturing an organic semiconductor film of the present invention. Specifically, FIGS. 4A to 4C are schematic views showing an aspect in which in a state where the substrate A and the member B remain in contact with each other, a coating solution is dropped onto a portion within the surface of the substrate A such that the coating solution contacts both of the substrate A and the member B, and the dropped coating solution is slowly dried in a state where the positional relationship between the substrate A and the member B is maintained.

FIGS. 5A to 5C are schematic views showing an aspect in which in a state where the substrate A and the member B remain in contact with each other, a coating solution is dropped onto a portion within the surface of the substrate A such that the coating solution contacts both of the substrate A and the member B, and the dropped coating solution is slowly dried by changing the positional relationship between the substrate A and the member B.

DESCRIPTION OF THE PREFERRED EMBODIMENTS

Figure 1:
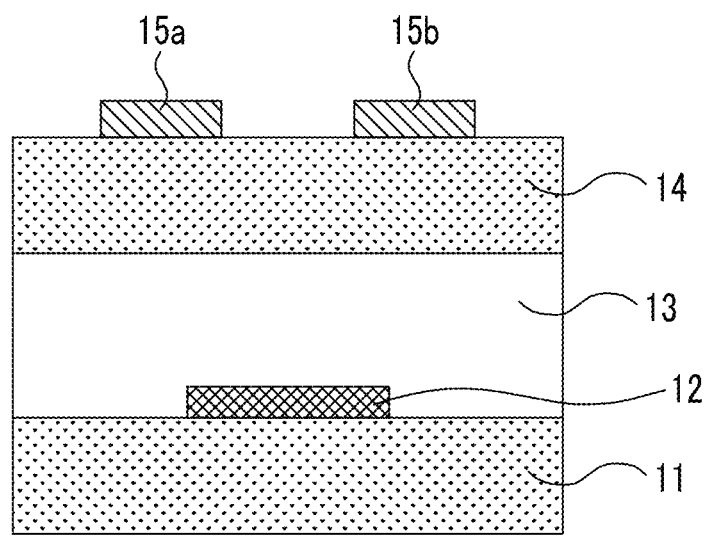
FIG. 1 is a schematic view showing a section of an exemplary structure of on organic transistor of the present invention.

Hereinafter, the present invention will be specifically described. The constituents described below will be explained based on representative embodiments or specific examples, but the present invention is not limited to the embodiments. In the present specification, a range of numerical values described using "to" means a range including the numerical values listed before and after "to" as a lower limit and an upper limit respectively.

In the present invention, unless otherwise specified, a hydrogen atom used in the description of each formula represents a hydrogen atom including an isotope (deuterium atom or the like). Furthermore, an atom constituting a substituent represents an atom including an isotope thereof.

[Organic Transistor]

An organic transistor of the present invention contains a compound, which is represented by the following Formula (1) and has a molecular weight of equal to or less than 3,000, in a semiconductor active layer.

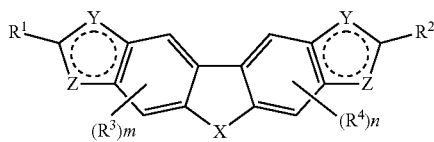

Formula (1)

In Formula (1),

X represents an oxygen atom, a sulfur atom, a selenium atom, a tellurium atom, or $NR^5$;

Y and Z each independently represent $CR^6$, an oxygen atom, a sulfur atom, a selenium atom, a nitrogen atom, or $NR^7$, two Y's may be the same as or different from each other, and two Z's may be the same as or different from each other;

a ring containing Y and Z is an aromatic heterocycle;

any one of $R^1$ and $R^2$ and the aromatic heterocycle containing Y and Z may be bonded to each other through the following group A of divalent linking groups;

any one of $R^3$ and $R^4$ and a benzene ring may be bonded to each other through the following group A of divalent linking groups;

the group A of divalent linking groups represents any one of divalent linking groups —O—, —S—, —$NR^8$—, —CO—, —SO—, and —$SO_2$— or represents a divalent linking group in which two or more of these divalent linking groups are bonded to each other;

$R^1$, $R^2$, $R^5$, $R^6$, $R^7$, and $R^8$ each independently represent a hydrogen atom, an alkyl group, an alkenyl group, an alkynyl group, an aryl group, or a heteroaryl group and may further have a substituent;

$R^3$ and $R^4$ each independently represent an alkyl group, an alkenyl group, an alkynyl group, an aryl group, or a heteroaryl group and may further have a substituent, in a case where m is 2, $R^3$'s may be the same as or different from each other, and in a case where n is 2, $R^4$'s may be the same as or different from each other;

m and n each independently represent an integer of 0 to 2;

here, a case where both of Y and Z are $CR^6$ and a case where both of Y and Z are any one of a nitrogen atom and $NR^7$ are excluded;

in a case where X is $NR^5$, Y is $CR^6$, and Z is a sulfur atom, a case where both of $R^1$ and $R^2$ are a hydrogen atom is excluded;

in a case where X is a sulfur atom, Y is CH, Z is a sulfur atom, and both of $R^1$ and $R^2$ are an alkyl group, any one of $R^1$ and $R^2$ and the aromatic heterocycle containing Y and Z are bonded to each other through the group A of divalent linking groups; and a case where both of $R^1$ and $R^2$ are a hydrogen atom, and both of m and n are 0 is excluded.

Due to the above constitution, the organic transistor of the present invention has high carrier mobility.

The reason why the organic transistor of the present invention has high carrier mobility is not limited and is considered to be as below according to the inventors of the present invention. By the selection of a specific substituent typified by the compound represented by Formula (1) and the selection of a substitution position, overlapping of orbitals between molecules becomes great, anisotropy is reduced, and as a result, carrier mobility can be improved.

It cannot be said that being useful as a material of an organic electroluminescence (EL) element means being useful as a semiconductor material for an organic transistor. This is because the characteristics required for an organic compound vary between an organic EL element and an organic transistor. A mobility of about $10^{-3}$ $cm^2$/Vs is enough for driving an organic EL element, and for improving organic EL characteristics, it is more important to improve luminous efficiency than to improve charge transport properties. Therefore, an element having high luminous efficiency and resulting in uniform in-plane luminescence is required. Generally, organic compounds having high crystallinity (high mobility) cause luminescence defectiveness such as non-uniform in-plane field intensity, non-uniform luminescence, and quenching of luminescence. Therefore, as materials for an organic EL element, those having low crystallinity but having high amorphousness (low mobility) are desirable. In contrast, in a semiconductor material for an organic transistor, extremely high mobility is desired. Accordingly, an organic compound showing highly ordered molecular arrangement and having high crystallinity is required.

Furthermore, for the expression of high carrier mobility, a π-conjugate plane is preferably upright against a substrate.

Hereinafter, preferred aspects of the compound and the organic transistor of the present invention will be described.

<Compound Represented by Formula (1) and Having Molecular Weight of Equal to or Less than 3,000>

Hereinafter, the compound which is represented by Formula (1) and has a molecular weight of equal to or less than 3,000 will be described.

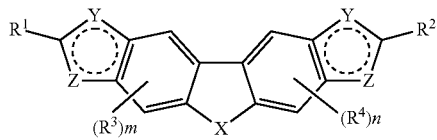

Formula (1)

In Formula (1), X represents an oxygen atom, a sulfur atom, a selenium atom, a tellurium atom, or $NR^5$. From the viewpoint of improving carrier mobility, X is preferably an oxygen atom, a sulfur atom, or a selenium atom, more preferably an oxygen atom or a sulfur atom, and particularly preferably a sulfur atom. In contrast, from the viewpoint of improving solubility, X is preferably a selenium atom.

In Formula (1), Y and Z each independently represent $CR^6$, an oxygen atom, a sulfur atom, a selenium atom, a nitrogen atom, or $NR^7$. Two Y's may be the same as or different from each other, and two Z's may be the same as or different from each other.

In Formula (1), a ring containing Y and Z is an aromatic heterocycle. Because the ring containing Y and Z is an aromatic heterocycle, for example, there is no case where both of Y and Z are a nitrogen atom and thus the ring becomes a radical compound.

Here, a case where both of Y and Z are $CR^6$ and a case where both of Y and Z are any one of a nitrogen atom and $NR^7$ are excluded from the range of Formula (1). In a case where both of Y and Z are $CR^6$, the ring does not become an aromatic heterocycle. In a case where both of Y and Z are any one of a nitrogen atom and $NR^7$, the highest occupied molecular orbital (HOMO) becomes too deep.

Each Y independently represents $CR^6$, an oxygen atom, a sulfur atom, a selenium atom, a nitrogen atom, or $NR^7$. Y is preferably $CR^6$, an oxygen atom, or a sulfur atom, and more preferably $CR^6$ or a sulfur atom.

Two Y's may be the same as or different from each other and are preferably the same as each other.

Each Z independently represents $CR^6$, an oxygen atom, a sulfur atom, a selenium atom, a nitrogen atom, or $NR^7$. Z is preferably $CR^6$, an oxygen atom, a sulfur atom, or $NR^7$, more preferably $CR^6$, an oxygen atom, or a sulfur atom, and particularly preferably $CR^6$ or a sulfur atom.

Two Z's may be the same as or different from each other and are preferably the same as each other.

Regarding a preferred combination of Y and Z, in a case where Y represents $CR^6$, Z is preferably an oxygen atom, a sulfur atom, or $NR^7$, more preferably an oxygen atom or a sulfur atom, and particularly preferably a sulfur atom.

In a case where Y represents an oxygen atom, Z is preferably $CR^6$, an oxygen atom, or a sulfur atom, more preferably $CR^6$ or a sulfur atom, and particularly preferably $CR^6$.

In a case where Y represents a sulfur atom, Z is preferably $CR^6$, an oxygen atom, a sulfur atom, or a nitrogen atom, more preferably $CR^6$ or a nitrogen atom, and particularly preferably $CR^6$.

In Formula (1), the ring containing Y and Z is an aromatic heterocycle. Each of the rings is preferably independently any one of a thiophene ring, a furan ring, a pyrrole ring, a thiazole ring, and an oxazole ring, more preferably a furan ring, a pyrrole ring, or a thiophene ring, and particularly preferably a thiophene ring.

In Formula (1), $R^1$ and $R^2$ each independently represent a hydrogen atom, an alkyl group, an alkenyl group, an alkynyl group, an aryl group, or a heteroaryl group and may further have a substituent. Each of $R^1$ and $R^2$ is preferably independently an alkyl group, an alkenyl group, an alkynyl group, an aryl group, or a heteroaryl group, more preferably an alkyl group, an aryl group, or a heteroaryl group, particularly preferably an alkyl group having 20 or less carbon atoms, an aryl group having 20 or less carbon atoms, or a heteroaryl group having 20 or less carbon atoms, and more particularly preferably a heteroaryl group having 20 or less carbon atoms.

In a case where $R^1$ or $R^2$ is an alkyl group, the number of carbon atoms of the alkyl group is preferably 1 to 30, more preferably 1 to 15 from the viewpoint of chemical stability and carrier mobility, and even more preferably 3 to 11. It is preferable that the $R^1$ and $R^2$ are preferably the alkyl group of the above range, because then molecular linearity and carrier mobility can be improved.

In a case where $R^1$ or $R^2$ represents an alkyl group, the alkyl group may be a linear, branched, or cyclic alkyl group. The alkyl group is preferably a linear alkyl group because then molecular linearity and carrier mobility can be improved.

In a case where $R^1$ or $R^2$ is an alkyl group having a substituent, the substituent is not particularly limited. Examples of the substituent include a halogen atom, an alkyl group (including an alkyl group having 1 to 40 carbon atoms such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, or a pentadecyl group; here, the alkyl group also includes a 2,6-dimethyloctyl group, a 2-decyltetradecyl group, a 2-hexyldodecyl group, a 2-ethyloctyl group, a 2-butyldecyl group, a 1-octylnonyl group, a 2-octyltetradecyl group, a 2-ethylhexyl group, a cycloalkyl group, a bicycloalkyl group, a tricycloalkyl group, and the like), an alkenyl group (including a 1-pentenyl group, a cycloalkenyl group, a bicycloalkenyl group, and the like), an alkynyl group (including a 1-pentynyl group, a trimethylsilylethynyl group, a triethylsilylethynyl group, a tri-1-propylsilylethynyl group, a 2-p-propylphenylethynyl group, and the like), an aryl group (including an aryl group having 6 to 20 carbon atoms such as a phenyl group, a naphthyl group, a p-pentylphenyl group, a 3,4-dipentylphenyl group, a p-heptoxyphenyl group, a 3,4-diheptoxyphenyl group, and the like), a hetero ring group (may be referred to as a heterocyclic group as well, including a 2-hexylfuranyl group and the like), a cyano group, a hydroxyl group, a nitro group, an acyl group (including a hexanoyl group, a benzoyl group, and the like), an alkoxy group (including a butoxy group and the like), an aryloxy group, a silyloxy group, a heterocyclic oxy group, an acyloxy group, a carbamoyloxy group, an amino group (including an anilino group), an acylamino group, an aminocarbonylamino group (including a ureido group), alkoxy- and aryloxycarbonylamino groups, alkyl- and aryl sulfonylamino groups, a mercapto group, alkyl- and arylthio groups (including a methylthio group, an octylthio group, and the like), a heterocyclic thio group, a sulfamoyl group, a sulfo group, alkyl- and aryl sulfinyl groups, alkyl- and aryl sulfonyl groups, alkyloxy- and aryloxycarbonyl groups, a carbamoyl group, aryl- and heterocyclic azo group, an imido group, a phosphino group, a phosphinyl group, a phosphinyloxy group, a phosphinylamino group, a phosphono group, a silyl group (a ditrimethylsiloxy methylbutoxy group), a hydrazino group, a ureido group, a boronic acid group ($-B(OH)_2$), a phosphate group ($-OPO(OH)_2$), a sulfate group ($-OSO_3H$), and other known substituents.

Among these, as the substituent adopted in a case where $R^1$ or $R^2$ is an alkyl group, a decyl group is preferable. Here, $R^1$ or $R^2$ is preferably an unsubstituted alkyl group.

In a case where $R^1$ or $R^2$ is an alkenyl group, the number of carbon atoms of the alkenyl group is preferably 2 to 30, more preferably 2 to 10, and particularly preferably 2 to 4.

In a case where $R^1$ or $R^2$ is an alkenyl group having a substituent, the substituent is not particularly limited. Examples of the substituent include the same substituents as exemplified above as the substituent adopted in a case where $R^1$ or $R^2$ is an alkyl group.

In a case where $R^1$ or $R^2$ is an alkynyl group, the number of carbon atoms of the alkynyl group is preferably 2 to 30, more preferably 2 to 10, and particularly preferably 2.

In a case where $R^1$ or $R^2$ is an alkynyl group having a substituent, the substituent is not particularly limited. Examples of the substituent include the same substituents as exemplified above as the substituent adopted in a case where IV and $R^2$ are an alkyl group. The substituent is more preferably a silyl group or an aryl group, particularly preferably a substituted or unsubstituted trialkylsilyl group or a substituted or unsubstituted phenyl group, and more particularly preferably a substituted or unsubstituted trialkylsilyl group. In a case where IV or $R^2$ is an alkynyl group, the substituent of a trialkylsilyl group substituting the alkynyl group is not particularly limited. The substituent is preferably a substituted or unsubstituted alkyl group, and more preferably a branched alkyl group. In this case, the number of carbon atoms of the alkyl group bonded to a Si atom is preferably 1 to 3. For example, the alkyl group is preferably a methyl group, an ethyl group, or an isopropyl group. The alkyl groups bonded to the Si atom may be the same as or different from each other.

In a case where $R^1$ or $R^2$ is an aryl group, the number of carbon atoms of the aryl group is preferably 6 to 30, more preferably 6 to 18, and particularly preferably 6 to 12.

In a case where $R^1$ or $R^2$ is an aryl group having a substituent, the substituent is not particularly limited. Examples of the substituent include the same substituents as exemplified above as the substituent adopted in a case where $R^1$ or $R^2$ is an alkyl group. The substituent is preferably an alkyl group. In a case where $R^1$ or $R^2$ is an aryl group, a preferred range of the alkyl group substituting the aryl group is the same as the preferred range of the alkyl group represented by $R^1$ or $R^2$.

In a case where $R^1$ or $R^2$ is an aryl group having a substituent, the number of substituents is not particularly limited. The number of substituents is preferably 1 to 3, more preferably 1 or 2, and particularly preferably 1.

In a case where $R^1$ or $R^2$ is a heteroaryl group, the number of carbon atoms of the heteroaryl group is preferably 3 to 30, more preferably 4 to 20, and particularly preferably 4. The heteroaryl group represented by $R^1$ or $R^2$ is preferably a furanyl group, a pyrrolyl group (in which a hydrogen atom may be substituted), a pyrazolyl group, an imidazolyl group, a thienyl group, a thiazolyl group, a thienothienyl group, a benzothienyl group, a thienophenyl group, a pyridyl group, a pyrimidinyl group, a pyridazinyl group, or a pyrazinyl group, more preferably a thienyl group or a furyl group, and particularly preferably a thienyl group.

In a case where $R^1$ or $R^2$ is a heteroaryl group having a substituent, the substituent is not particularly limited. Examples of the substituent include the same substituents as exemplified above as the substituent adopted in a case where $R^1$ or $R^2$ is an alkyl group. The substituent is preferably an alkyl group. In a case where $R^1$ or $R^2$ is a heteroaryl group, a preferred range of the alkyl group substituting the heteroaryl group is the same as the preferred range of the alkyl group represented by $R^1$ or $R^2$.

In Formula (1), between $R^1$ and $R^2$, each $R^1$ is more preferably independently a group having a aliphatic hydrocarbon group from the viewpoint of improving carrier mobility, and even more preferably independently an aryl group having a linear aliphatic hydrocarbon group or a heteroaryl group having a linear aliphatic hydrocarbon group from the viewpoint of further improving carrier mobility.

In Formula (1), the number of carbon atoms contained in $R^1$ or $R^2$ is preferably equal to or less than 30 from the viewpoint of carrier mobility. The number of carbon atoms contained in $R^1$ or $R^2$ is preferably 1 to 18, more preferably 5 to 18, and particularly preferably 7 to 18. If the total number of carbon atoms contained in $R^1$ or $R^2$ is equal to or greater than the lower limit of the above range, carrier mobility is improved.

In Formula (1), any one of $R^1$ and $R^2$ and the aromatic heterocycle containing Y and Z may be bonded to each other through the following group A of divalent linking groups. The group A of divalent linking groups represents any one of divalent linking groups —O—, —S—, —NR$^8$—, —CO—, —SO—, and —SO$_2$— or represents a divalent linking group in which two or more of these divalent linking group are bonded to each other. Among these, the group A of divalent linking groups is preferably any one of divalent linking groups —O—, —S—, —CO—, —SO—, and —SO$_2$—, more preferably —O— or —S—, and particularly preferably —O—.

In Formula (1), the combination of X, Y, Z, $R^1$, and $R^2$ is partially limited. From the viewpoint of carrier mobility, in a case where X is NR$^5$, Y is CR$^6$, and Z is a sulfur atom, a case where both of $R^1$ and $R^2$ are a hydrogen atom is excluded from the range represented by Formula (1). Furthermore, in a case where X, Y, and Z in Formula (1) are a sulfur atom, CH, and a sulfur atom respectively, and both of $R^1$ and $R^2$ in Formula (1) are an alkyl group, any one of $R^1$ and $R^2$ and the aromatic heterocycle containing Y and Z are bonded to each other through the group A of divalent linking groups.

In Formula (1), $R^1$ and $R^2$ are preferably the same as each other.

In Formula (1), $R^3$ and $R^4$ each independently represent an alkyl group, an alkenyl group, an alkynyl group, an aryl group, or a heteroaryl group and may further have a substituent. In a case where m in Formula (1) is 2, $R^3$'s may be the same as or different from each other. In a case where n in Formula (1) is 2, $R^4$'s may be the same as or different from each other. $R^3$ and $R^4$ are preferably an alkyl group having 3 to 11 carbon atoms.

In Formula (1), the number of carbon atoms contained in $R^3$ or $R^4$ is preferably equal to or less than 30 from the viewpoint of carrier mobility.

In Formula (1), any one of $R^3$ and $R^4$ and a benzene ring may be bonded to each other through the group A of divalent linking groups.

In Formula (1), $R^3$ and $R^4$ are preferably the same as each other.

In Formula (1), $R^5$ in NR$^5$ that can be adopted as X represents a hydrogen atom, an alkyl group, an alkenyl group, an alkynyl group, an aryl group, or a heteroaryl group and may further have a substituent. $R^5$ is preferably an alkyl group having 3 to 11 carbon atoms.

In Formula (1), $R^6$ in CR$^6$ that can be adopted as Y and Z represents a hydrogen atom, an alkyl group, an alkenyl group, an alkynyl group, an aryl group, or a heteroaryl group and may further have a substituent. $R^6$ is preferably a hydrogen atom or an alkyl group, and more preferably a hydrogen atom. A preferred range of the alkyl group that can be adopted as $R^6$ is the same as the preferred range of the alkyl group that can be adopted as $R^1$ and $R^2$.

In Formula (1), $R^7$ in NR$^7$ that can be adopted as Y and Z represents a hydrogen atom, an alkyl group, an alkenyl group, an alkynyl group, an aryl group, or a heteroaryl group and may further have a substituent. $R^7$ is preferably an alkyl group or an aryl group, and more preferably an alkyl group. A preferred range of the alkyl group that can be adopted as $R^7$ is the same as the preferred range of the alkyl group that can be adopted as $R^1$ and $R^2$.

In Formula (1), $R^8$ in NR$^8$ that can be adopted as the group A of divalent linking groups represents a hydrogen atom, an alkyl group, an alkenyl group, an alkynyl group, an aryl group, or a heteroaryl group and may further have a substituent. $R^8$ is more preferably an alkyl group or an aryl group.

In Formula (1), each of m and n is independently an integer of 0 to 2. Each of m and n is preferably 0 or 1, and more preferably 0. It is particularly preferable that both of m and n are 0.

Here, from the viewpoint of carrier mobility, a case where both of $R^1$ and $R^2$ in Formula (1) are a hydrogen atom and both of m and n in Formula (1) are 0 is excluded.

In Formula (1), m and n are preferably the same as each other.

From the viewpoint of improving carrier mobility by improving molecular symmetry, $R^1$ and $R^2$ in Formula (1) are preferably the same as each other, $R^3$ and $R^4$ in Formula (1) are preferably the same as each other, and m and n in Formula (1) are preferably the same as each other.

(Compound Represented by Formula (1A) and Having Molecular Weight of Equal to or Less than 3,000)

Among compounds which are represented by Formula (1) and have a molecular weight of equal to or less than 3,000, a compound which is represented by the following Formula (1A) and has a molecular weight of equal to or less than 3,000 is preferable.

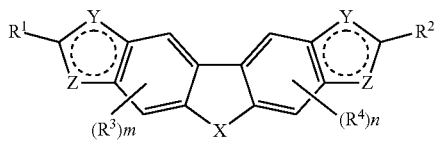

Formula (1A)

In Formula (1A),

X represents an oxygen atom, a sulfur atom, a selenium atom, a tellurium atom, or $NR^5$;

Y and Z each independently represent $CR^6$, an oxygen atom, a sulfur atom, a selenium atom, a nitrogen atom, or $NR^7$, two Y's may be the same as or different from each other, and two Z's may be the same as or different from each other;

a ring containing Y and Z is an aromatic heterocycle;

any one of $R^1$ and $R^2$ and the aromatic heterocycle containing Y and Z may be bonded to each other through the following group A of divalent linking groups;

any one of $R^3$ and $R^4$ and a benzene ring may be bonded to each other through the following group A of divalent linking groups;

the group A of divalent linking groups represents any one of divalent linking groups —O—, —S—, —$NR^8$—, —CO—, —SO—, and —$SO_2$— or represents a divalent linking group in which two or more of these divalent linking groups are bonded to each other;

$R^1$, $R^2$, $R^5$, $R^6$, $R^7$, and $R^8$ each independently represent a hydrogen atom, an alkyl group, an alkenyl group, an alkynyl group, an aryl group, or a heteroaryl group and may further have a substituent;

$R^3$ and $R^4$ each independently represent an alkyl group, an alkenyl group, an alkynyl group, an aryl group, or a heteroaryl group and may further have a substituent, in a case where m is 2, $R^3$'s may be the same as or different from each other, and in a case where n is 2, $R^4$'s may be the same as or different from each other;

m and n each independently represent an integer of 0 to 2;

here, a case where both of Y and Z are $CR^6$ and a case where both of Y and Z are any one of a nitrogen atom and $NR^7$ are excluded;

a case where X is $NR^5$, Y is a nitrogen atom, and Z is an oxygen atom is excluded;

in a case where X is $NR^5$, Y is $CR^6$, and Z is a sulfur atom, a case where both of $R^1$ and $R^2$ are a hydrogen atom is excluded;

in a case where X is a sulfur atom, Y is CH, Z is a sulfur atom, and both of $R^1$ and $R^2$ are an alkyl group, any one of $R^1$ and $R^2$ and an aromatic heterocycle containing Y and Z are bonded to each other through the group A of divalent linking groups; and a case where both of $R^1$ and $R^2$ are a hydrogen atom, and both of m and n are 0 is excluded.

The compound which is represented by Formula (1A) and has a molecular weight of equal to or less than 3,000 is a novel compound. The novel compound is referred to as a compound of the present invention. That is, the compound of the present invention is represented by the following Formula (1A) and has a molecular weight of equal to or less than 3,000. The range of Formula (1A) does not include a case where X, Y, and Z in Formula (1) are $NR^5$, a nitrogen atom, and an oxygen atom respectively.

A preferred range of Formula (1A) is the same as the preferred range of Formula (1).

Similar to the compound which is represented by Formula (1) and has a molecular weight of equal to or less than 3,000, the compound of the present invention is contained in a semiconductor active layer, which will be described later, of the organic transistor of the present invention. That is, the compound of the present invention can be used as a material for an organic transistor.

(Compound Represented by Formula (2) or (3) and Having Molecular Weight of Equal to or Less than 3,000)

The compound which is represented by Formula (1) and has a molecular weight of equal to or less than 3,000 is preferably a compound which is represented by the following Formula (2) or (3) and has a molecular weight of equal to or less than 3,000.

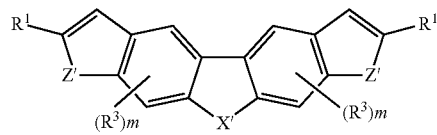

Formula (2)

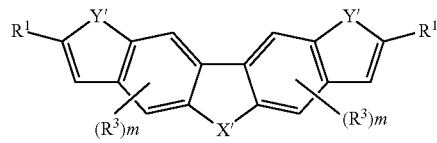

Formula (3)

In Formulae (2) and (3), each X' independently represents an oxygen atom, a sulfur atom, or a selenium atom;

each of Y' and Z' is independently selected from $NR^7$, an oxygen atom, a sulfur atom, and a selenium atom;

a ring containing Y' and Z' is an aromatic heterocycle;

$R^1$ and the aromatic heterocycle containing Y' and Z' may be bonded to each other through the following group A of divalent linking groups;

$R^3$ and a benzene ring may be bonded to each other through the following group A of divalent linking groups;

the group A of divalent linking groups represents any one of divalent linking groups —O—, —S—, —$NR^8$—, —CO—, —SO—, and —SO$_2$— or represents a divalent linking group in which two or more of these divalent linking groups are bonded to each other;

R$^1$, R$^7$, and R$^8$ each independently represent a hydrogen atom, an alkyl group, an alkenyl group, an alkynyl group, an aryl group, or a heteroaryl group and may further have a substituent, and two or more R$^1$'s may be the same as or different from each other;

each R$^3$ independently represents an alkyl group, an alkenyl group, an alkynyl group, an aryl group, or a heteroaryl group and may further have a substituent, and in a case where m is 2, R$^3$'s may be the same as or different from each other;

each m is independently an integer of 0 to 2;

here, a case where both of Y' and Z' are NR$^7$ is excluded;

in a case where X', Z', and R' in Formula (2) are a sulfur atom, a sulfur atom, and an alkyl group respectively, R$^1$ and the aromatic heterocycle containing Z' are bonded to each other through the group A of divalent linking groups; and a case where R$^1$ is a hydrogen atom and both of m's are 0 is excluded.

In Formulae (2) and (3), a preferred range of X' is the same as the preferred range of X in Formula (1).

In Formulae (2) and (3), a preferred range of each of Y' and Z' is the same as the preferred range of each of Y and Z in Formula (1).

In Formulae (2) and (3), a definition and a preferred range of the group A of divalent linking groups are the same as the definition and the preferred range of the group A of divalent linking groups in Formula (1).

In Formulae (2) and (3), a preferred range of R$^1$ is the same as the preferred range of the combination of R$^1$ and R$^2$ in Formula (1).

In Formulae (2) and (3), a preferred range of R$^3$ is the same as the preferred range of the combination of R$^3$ and R$^4$ in Formula (1).

In Formulae (2) and (3), a preferred range of each of R$^7$ and R$^8$ is the same as the preferred range of each of R$^7$ and R$^8$ in Formula (1).

In Formulae (2) and (3), a definition and a preferred range of m is the same as the definition and the preferred range of m in Formula (1).

(Compound Represented by Formula (4) or (5) and Having Molecular Weight of Equal to or Less than 3,000)

The compound which is represented by Formula (1) and has a molecular weight of equal to or less than 3,000 is preferably a compound which is represented by the following Formula (4) or (5) and has a molecular weight of equal to or less than 3,000.

The compound which is represented by Formula (2) and has a molecular weight of equal to or less than 3,000 is preferably a compound which is represented by Formula (4) and has a molecular weight of equal to or less than 3,000.

The compound which is represented by Formula (3) and has a molecular weight of equal to or less than 3,000 is preferably a compound which is represented by Formula (5) and has a molecular weight of equal to or less than 3,000.

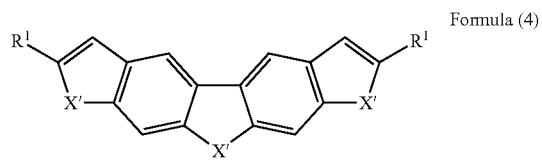

Formula (4)

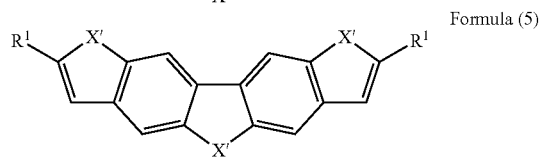

Formula (5)

In Formulae (4) and (5), each X$^1$ independently represents an oxygen atom, a sulfur atom, or a selenium atom;

R$^1$ and an aromatic heterocycle containing X' may be bonded to each other through the following group A of divalent linking groups;

the group A of divalent linking groups represents any one of divalent linking groups —O—, —S—, —NR$^8$—, —CO—, —SO—, and —SO$_2$— or represents a divalent linking group in which two or more of these divalent linking groups are bonded to each other;

R$^1$ and R$^8$ each independently represent a hydrogen atom, an alkyl group, an alkenyl group, an alkynyl group, an aryl group, or a heteroaryl group and may further have a substituent, and two or more R$^1$'s may be the same as or different from each other;

here, in a case where all of X's in Formula (4) are a sulfur atom, and R$^1$ in Formula (4) is an alkyl group, R$^1$ and the aromatic heterocycle containing X' are bonded to each other through the group A of divalent linking groups; and a case where R$^1$ is a hydrogen atom is excluded.

In Formula (4), a preferred range of X' is the same as the preferred range of the combination of X and Y in Formula (1).

In Formula (5), a preferred range of X' is the same as the preferred range of the combination of X and Y in Formula (1).

In Formulae (4) and (5), a definition and a preferred range of the group A of divalent linking groups is the same as the definition and the preferred range of the group A of divalent linking groups in Formula (1).

In Formulae (4) and (5), a preferred range of R$^1$ is the same as the preferred range of the combination of R$^1$ and R$^2$ in Formula (1). R$^1$ is more preferably a group having an aliphatic hydrocarbon group, and evenmore preferably an aryl group having a linear aliphatic hydrocarbon group or a heteroaryl group having a linear aliphatic hydrocarbon group.

Specific examples of the compound which is represented by Formula (1) and has a molecular weight of equal to or less than 3,000 will be shown below. However, the compound, which is represented by Formula (1) and has a molecular weight of equal to or less than 3,000, usable in the present invention is not limited to the following specific examples.

From Table 2, each of the columns in the following tables has the same definition as each of the columns on the first line of Table 1. That is, from Table 2, each of the columns represents X, Y, Z, m, n, R$^1$, R$^2$, R$^3$, and R$^4$ in this order from left. Furthermore, in a case where Z in each table represents NR$^7$, N(n-C$_{10}$H$_{21}$) is listed.

TABLE 1

| Specific example | X | Y | Z | m | n | R¹ | R² | R³ | R⁴ |
|---|---|---|---|---|---|---|---|---|---|
| 1 | O | CH | O | 0 | 0 | $CH_3$ | $CH_3$ | — | — |
| 2 | O | CH | O | 0 | 0 | $n\text{-}C_4H_9$ | $n\text{-}C_4H_9$ | — | — |
| 3 | O | CH | O | 0 | 0 | $n\text{-}C_5H_{11}$ | $n\text{-}C_5H_{11}$ | — | — |
| 4 | O | CH | O | 0 | 0 | $n\text{-}C_6H_{13}$ | $n\text{-}C_6H_{13}$ | — | — |
| 5 | O | CH | O | 0 | 0 | $n\text{-}C_7H_{15}$ | $n\text{-}C_7H_{15}$ | — | — |
| 6 | O | CH | O | 0 | 0 | $n\text{-}C_8H_{17}$ | $n\text{-}C_8H_{17}$ | — | — |
| 7 | O | CH | O | 0 | 0 | $n\text{-}C_9H_{19}$ | $n\text{-}C_9H_{19}$ | — | — |
| 8 | O | CH | O | 0 | 0 | $n\text{-}C_{10}H_{21}$ | $n\text{-}C_{10}H_{21}$ | — | — |
| 9 | O | CH | O | 0 | 0 | $n\text{-}C_{11}H_{23}$ | $n\text{-}C_{11}H_{23}$ | — | — |
| 10 | O | CH | O | 0 | 0 | $n\text{-}C_{12}H_{25}$ | $n\text{-}C_{12}H_{25}$ | — | — |
| 11 | O | CH | O | 0 | 0 | –O–$nC_6H_{13}$ | –O–$nC_6H_{13}$ | — | — |
| 12 | O | CH | O | 0 | 0 | –O–$nC_{10}H_{21}$ | –O–$nC_{10}H_{21}$ | — | — |
| 13 | O | CH | O | 0 | 0 | 2-ethylhexyl | 2-ethylhexyl | — | — |
| 14 | O | CH | O | 0 | 0 | propenyl | propenyl | — | — |
| 15 | O | CH | O | 0 | 0 | ethynyl | ethynyl | — | — |
| 16 | O | CH | O | 0 | 0 | (triisopropylsilyl)ethynyl | (triisopropylsilyl)ethynyl | — | — |
| 17 | O | CH | O | 0 | 0 | phenyl | phenyl | — | — |
| 18 | O | CH | O | 0 | 0 | 3-($nC_6H_{13}$)phenyl | 3-($nC_6H_{13}$)phenyl | — | — |
| 19 | O | CH | O | 0 | 0 | 3-($nC_{10}H_{21}$)phenyl | 3-($nC_{10}H_{21}$)phenyl | — | — |
| 20 | O | CH | O | 0 | 0 | 3-(2-ethylhexyl)phenyl | 3-(2-ethylhexyl)phenyl | — | — |

TABLE 2

| # | | | | | | Ar1 | Ar2 | | |
|---|---|---|---|---|---|---|---|---|---|
| 21 | O | CH | O | 0 | 0 | 4-nC6H13-phenyl | 4-nC6H13-phenyl | — | — |
| 22 | O | CH | O | 0 | 0 | 4-nC10H21-phenyl | 4-nC10H21-phenyl | — | — |
| 23 | O | CH | O | 0 | 0 | 3,5-di(nC6H13)-phenyl | 3,5-di(nC6H13)-phenyl | — | — |
| 24 | O | CH | O | 0 | 0 | 3,5-di(nC10H21)-phenyl | 3,5-di(nC10H21)-phenyl | — | — |
| 25 | O | CH | O | 0 | 0 | furan-2-yl | furan-2-yl | — | — |
| 26 | O | CH | O | 0 | 0 | 5-nC6H13-furan-2-yl | 5-nC6H13-furan-2-yl | — | — |
| 27 | O | CH | O | 0 | 0 | 5-nC10H21-furan-2-yl | 5-nC10H21-furan-2-yl | — | — |
| 28 | O | CH | O | 0 | 0 | 4-nC6H13-furan-2-yl | 4-nC6H13-furan-2-yl | — | — |
| 29 | O | CH | O | 0 | 0 | 4-nC10H21-furan-2-yl | 4-nC10H21-furan-2-yl | — | — |
| 30 | O | CH | O | 0 | 0 | 1H-pyrrol-2-yl | 1H-pyrrol-2-yl | — | — |
| 31 | O | CH | O | 0 | 0 | 1-methyl-5-nC6H13-pyrrol-2-yl | 1-methyl-5-nC6H13-pyrrol-2-yl | — | — |
| 32 | O | CH | O | 0 | 0 | 1-nC6H13-pyrrol-2-yl | 1-nC6H13-pyrrol-2-yl | — | — |
| 33 | O | CH | O | 0 | 0 | 1-nC10H21-pyrrol-2-yl | 1-nC10H21-pyrrol-2-yl | — | — |
| 34 | O | CH | O | 0 | 0 | thiophen-2-yl | thiophen-2-yl | — | — |
| 35 | O | CH | O | 0 | 0 | thiophen-3-yl | thiophen-3-yl | — | — |
| 36 | O | CH | O | 0 | 0 | 4-nC5H11-thiophen-2-yl | 4-nC5H11-thiophen-2-yl | — | — |
| 37 | O | CH | O | 0 | 0 | 4-nC6H13-thiophen-2-yl | 4-nC6H13-thiophen-2-yl | — | — |
| 38 | O | CH | O | 0 | 0 | 4-nC8H17-thiophen-2-yl | 4-nC8H17-thiophen-2-yl | — | — |
| 39 | O | CH | O | 0 | 0 | 4-nC10H21-thiophen-2-yl | 4-nC10H21-thiophen-2-yl | — | — |
| 40 | O | CH | O | 0 | 0 | 4-nC12H25-thiophen-2-yl | 4-nC12H25-thiophen-2-yl | — | — |

TABLE 3

| # | | | | | | Ar1 | Ar2 | | |
|---|---|---|---|---|---|---|---|---|---|
| 41 | O | CH | O | 0 | 0 | 5-nC6H13-thiophen-2-yl (bithiophene) | 5-nC6H13-thiophen-2-yl (bithiophene) | — | — |
| 42 | O | CH | O | 0 | 0 | 5-nC10H21-thiophen-2-yl (bithiophene) | 5-nC10H21-thiophen-2-yl (bithiophene) | — | — |
| 43 | O | CH | O | 0 | 0 | 5-nC5H11-thiophen-2-yl (bithiophene) | 5-nC5H11-thiophen-2-yl (bithiophene) | — | — |
| 44 | O | CH | O | 0 | 0 | 5-nC6H13-thiophen-2-yl (bithiophene) | 5-nC6H13-thiophen-2-yl (bithiophene) | — | — |

TABLE 3-continued
| 45 | O | CH | O | 0 | 0 | 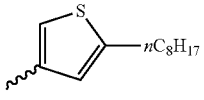 | 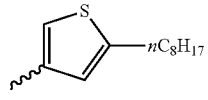 | — | — |
| 46 | O | CH | O | 0 | 0 | 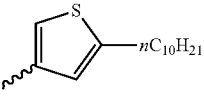 | 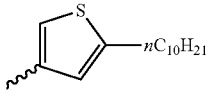 | — | — |
| 47 | O | CH | O | 0 | 0 | 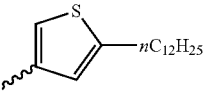 | 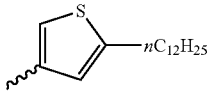 | — | — |
| 48 | O | CH | O | 0 | 0 | 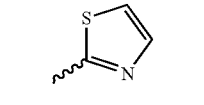 | 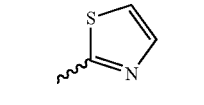 | — | — |
| 49 | O | CH | O | 0 | 0 | 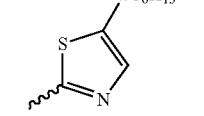 | 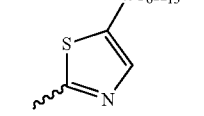 | — | — |
| 50 | O | CH | O | 0 | 0 | 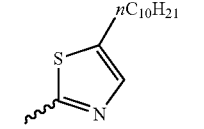 | 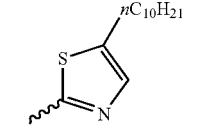 | — | — |
| 51 | O | CH | O | 0 | 0 | 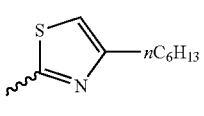 | 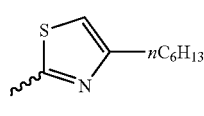 | — | — |
| 52 | O | CH | O | 0 | 0 | 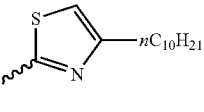 | 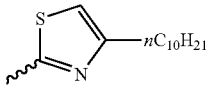 | — | — |
| 53 | O | CH | O | 0 | 0 | 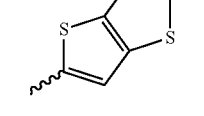 | 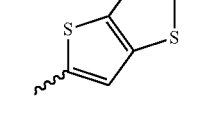 | — | — |
| 54 | O | CH | O | 0 | 0 | 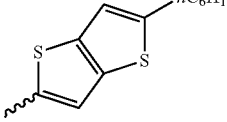 | 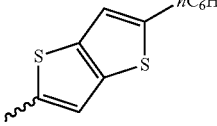 | — | — |
| 55 | O | CH | O | 0 | 0 | 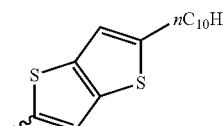 | 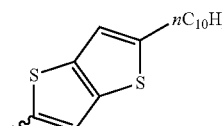 | — | — |
| 56 | O | CH | O | 0 | 0 | 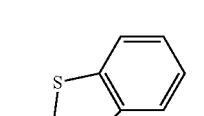 | 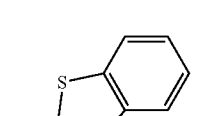 | — | — |
| 57 | O | CH | O | 0 | 0 | 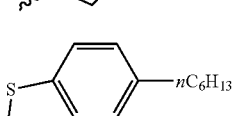 | 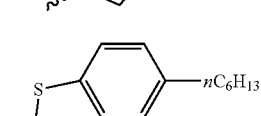 | — | — |

TABLE 3-continued
| | | | | | | | | | |
|---|---|---|---|---|---|---|---|---|---|
| 58 | O | CH | O | 0 | 0 | 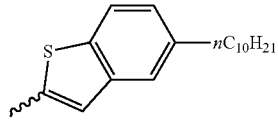 | 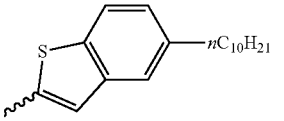 | — | — |
| 59 | O | CH | O | 0 | 0 | 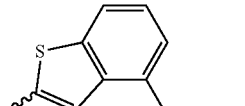 |  | — | — |
| 60 | O | CH | O | 0 | 0 | 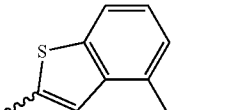 | 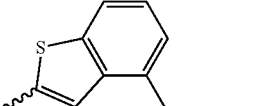 | — | — |
TABLE 4
| | | | | | | | | | |
|---|---|---|---|---|---|---|---|---|---|
| 61 | O | CH | O | 0 | 0 | 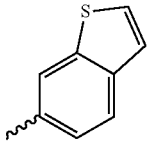 | 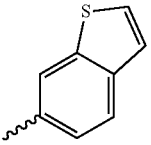 | — | — |
| 62 | O | CH | O | 0 | 0 | 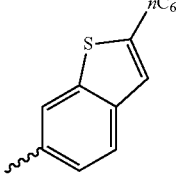 | 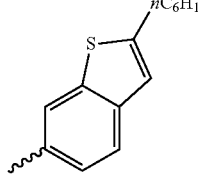 | — | — |
| 63 | O | CH | O | 0 | 0 | 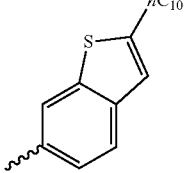 | 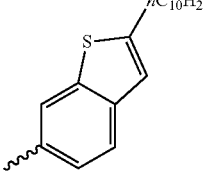 | — | — |
| 64 | O | CH | O | 0 | 0 | 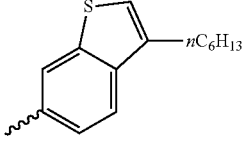 | 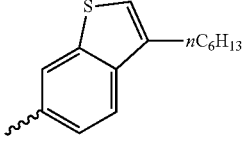 | — | — |
| 65 | O | CH | O | 0 | 0 | 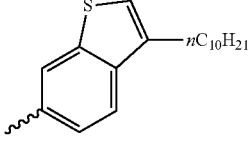 | 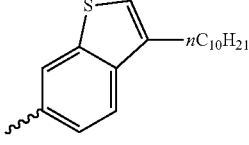 | — | — |
| 66 | O | CH | O | 0 | 0 | 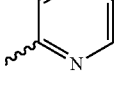 | 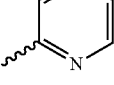 | — | — |
| 67 | O | CH | O | 0 | 0 | 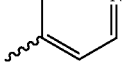 | 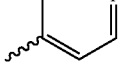 | — | — |

TABLE 4-continued

| # | | | | | | Ar1 | Ar2 | R1 | R2 |
|---|---|---|---|---|---|---|---|---|---|
| 68 | O | CH | O | 0 | 0 | 3-pyridyl | 3-pyridyl | — | — |
| 69 | O | CH | O | 0 | 0 | 4-nC6H13-pyridin-2-yl | 4-nC6H13-pyridin-2-yl | — | — |
| 70 | O | CH | O | 0 | 0 | 4-nC10H21-pyridin-2-yl | 4-nC10H21-pyridin-2-yl | — | — |
| 71 | O | CH | O | 0 | 0 | 5-nC6H13-pyridin-2-yl | 5-nC6H13-pyridin-2-yl | — | — |
| 72 | O | CH | O | 0 | 0 | 5-nC10H21-pyridin-2-yl | 5-nC10H21-pyridin-2-yl | — | — |
| 73 | O | CH | O | 0 | 0 | 2-nC6H13-pyridin-4-yl | 2-nC6H13-pyridin-4-yl | — | — |
| 74 | O | CH | O | 0 | 0 | 2-nC10H21-pyridin-4-yl | 2-nC10H21-pyridin-4-yl | — | — |
| 75 | O | CH | O | 0 | 0 | 5-nC6H13-pyridin-3-yl | 5-nC6H13-pyridin-3-yl | — | — |
| 76 | O | CH | O | 0 | 0 | 5-nC10H21-pyridin-3-yl | 5-nC10H21-pyridin-3-yl | — | — |
| 77 | O | CH | O | 2 | 2 | H | H | n-C6H13 | n-C6H13 |
| 78 | O | CH | O | 2 | 2 | H | H | n-C10H21 | n-C10H21 |
| 79 | S | CH | O | 0 | 0 | CH3 | CH3 | — | — |
| 80 | S | CH | O | 0 | 0 | n-C4H9 | n-C4H9 | — | — |

TABLE 5

| # | | | | | | Ar1 | Ar2 | | |
|---|---|---|---|---|---|---|---|---|---|
| 81 | S | CH | O | 0 | 0 | n-C5H11 | n-C5H11 | — | — |
| 82 | S | CH | O | 0 | 0 | n-C6H13 | n-C6H13 | — | — |
| 83 | S | CH | O | 0 | 0 | n-C7H15 | n-C7H15 | — | — |
| 84 | S | CH | O | 0 | 0 | n-C8H17 | n-C8H17 | — | — |
| 85 | S | CH | O | 0 | 0 | n-C9H19 | n-C9H19 | — | — |
| 86 | S | CH | O | 0 | 0 | n-C10H21 | n-C10H21 | — | — |
| 87 | S | CH | O | 0 | 0 | n-C11H23 | n-C11H23 | — | — |
| 88 | S | CH | O | 0 | 0 | n-C12H25 | n-C12H25 | — | — |
| 89 | S | CH | O | 0 | 0 | O-nC6H13 | O-nC6H13 | — | — |

TABLE 5-continued
| | | | | | | | | |
|---|---|---|---|---|---|---|---|---|
| 90 | S | CH | O | 0 | 0 | 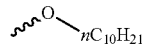 | 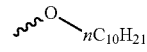 | — — |
| 91 | S | CH | O | 0 | 0 | 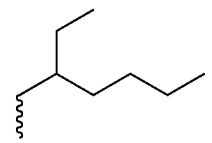 | 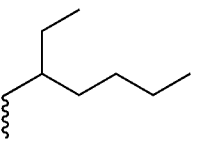 | — — |
| 92 | S | CH | O | 0 | 0 | 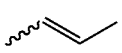 | 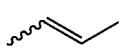 | — — |
| 93 | S | CH | O | 0 | 0 |  |  | — — |
| 94 | S | CH | O | 0 | 0 | 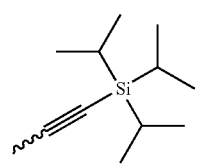 | 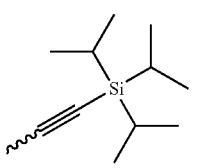 | — — |
| 95 | S | CH | O | 0 | 0 | 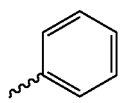 | 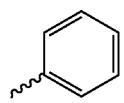 | — — |
| 96 | S | CH | O | 0 | 0 | 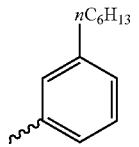 | 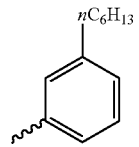 | — — |
| 97 | S | CH | O | 0 | 0 | 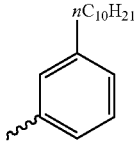 | 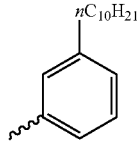 | — — |
| 98 | S | CH | O | 0 | 0 | 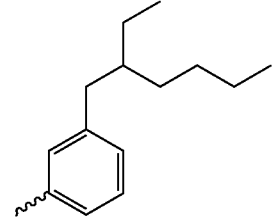 | 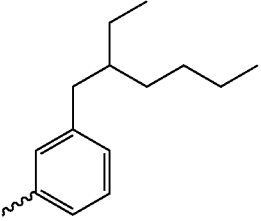 | — — |
| 99 | S | CH | O | 0 | 0 | 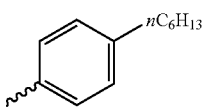 | 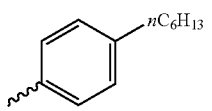 | — — |
| 100 | S | CH | O | 0 | 0 | 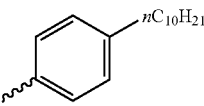 | 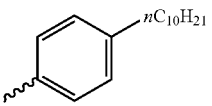 | — — |

TABLE 6
| 101 | S | CH | O | 0 | 0 | 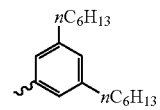 | 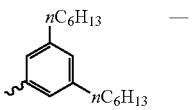 | — | — |
| 102 | S | CH | O | 0 | 0 | 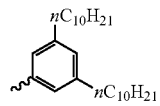 | 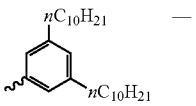 | — | — |
| 103 | S | CH | O | 0 | 0 | 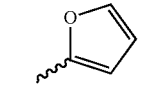 | 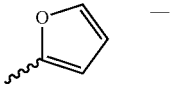 | — | — |
| 104 | S | CH | O | 0 | 0 | 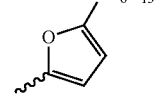 | 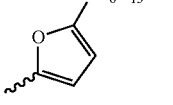 | — | — |
| 105 | S | CH | O | 0 | 0 | 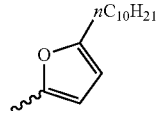 | 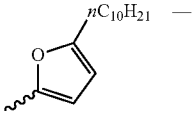 | — | — |
| 106 | S | CH | O | 0 | 0 | 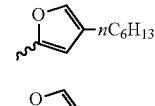 | 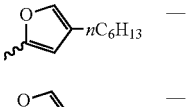 | — | — |
| 107 | S | CH | O | 0 | 0 | 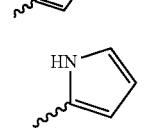 | 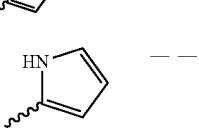 | — | — |
| 108 | S | CH | O | 0 | 0 | 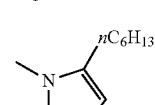 | 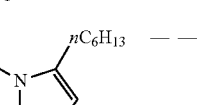 | — | — |
| 109 | S | CH | O | 0 | 0 | 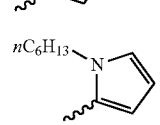 | 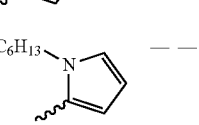 | — | — |
| 110 | S | CH | O | 0 | 0 |  |  | — | — |
TABLE 6-continued
| 111 | S | CH | O | 0 | 0 | 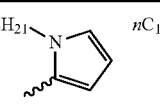 | 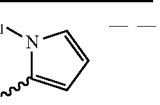 | — | — |
| 112 | S | CH | O | 0 | 0 | 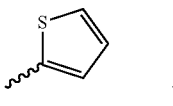 | 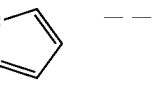 | — | — |
| 113 | S | CH | O | 0 | 0 | 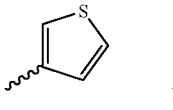 | 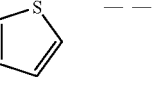 | — | — |
| 114 | S | CH | O | 0 | 0 | 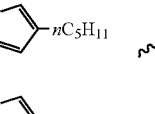 | 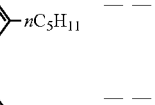 | — | — |
| 115 | S | CH | O | 0 | 0 | 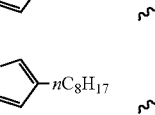 | 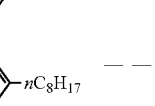 | — | — |
| 116 | S | CH | O | 0 | 0 | 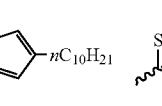 | 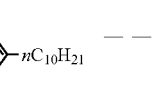 | — | — |
| 117 | S | CH | O | 0 | 0 | 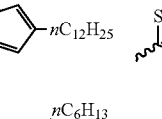 | 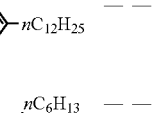 | — | — |
| 118 | S | CH | O | 0 | 0 | 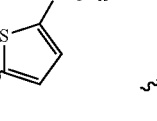 |  | — | — |
| 119 | S | CH | O | 0 | 0 | 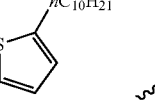 | 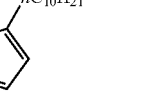 | — | — |
| 120 | S | CH | O | 0 | 0 | 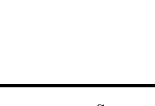 | 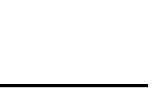 | — | — |
TABLE 7
| 121 | S | CH | O | 0 | 0 | 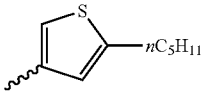 | 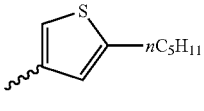 | — | — |
| 122 | S | CH | O | 0 | 0 | 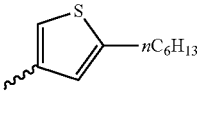 | 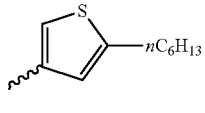 | — | — |
| 123 | S | CH | O | 0 | 0 | 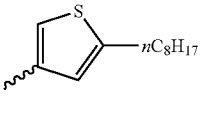 | 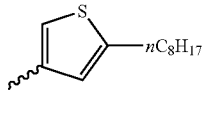 | — | — |
| 124 | S | CH | O | 0 | 0 | 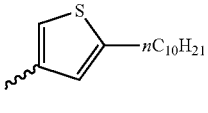 | 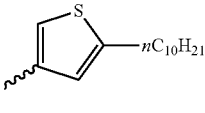 | — | — |

TABLE 7-continued

| 125 | S | CH | O | 0 | 0 | thiophene-nC₁₂H₂₅ | thiophene-nC₁₂H₂₅ | — | — |
| 126 | S | CH | O | 0 | 0 | thiazole | thiazole | — | — |
| 127 | S | CH | O | 0 | 0 | thiazole-nC₆H₁₃ | thiazole-nC₆H₁₃ | — | — |
| 128 | S | CH | O | 0 | 0 | thiazole-nC₁₀H₂₁ | thiazole-nC₁₀H₂₁ | — | — |
| 129 | S | CH | O | 0 | 0 | thiazole-nC₆H₁₃ | thiazole-nC₆H₁₃ | — | — |
| 130 | S | CH | O | 0 | 0 | thiazole-nC₁₀H₂₁ | thiazole-nC₁₀H₂₁ | — | — |
| 131 | S | CH | O | 0 | 0 | thienothiophene | thienothiophene | — | — |
| 132 | S | CH | O | 0 | 0 | thienothiophene-nC₆H₁₃ | thienothiophene-nC₆H₁₃ | — | — |
| 133 | S | CH | O | 0 | 0 | thienothiophene-nC₁₀H₂₁ | thienothiophene-nC₁₀H₂₁ | — | — |
| 134 | S | CH | O | 0 | 0 | benzothiophene | benzothiophene | — | — |
| 135 | S | CH | O | 0 | 0 | benzothiophene-nC₆H₁₃ | benzothiophene-nC₆H₁₃ | — | — |
| 136 | S | CH | O | 0 | 0 | benzothiophene-nC₁₀H₂₁ | benzothiophene-nC₁₀H₂₁ | — | — |

TABLE 7-continued
| | | | | | | | | | |
|---|---|---|---|---|---|---|---|---|---|
| 137 | S | CH | O | 0 | 0 | 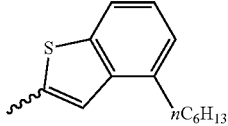 | 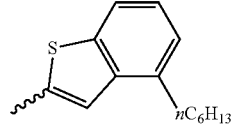 | — | — |
| 138 | S | CH | O | 0 | 0 | 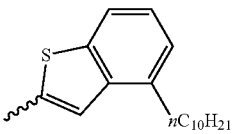 | 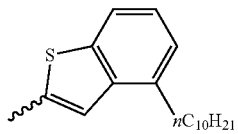 | — | — |
| 139 | S | CH | O | 0 | 0 | 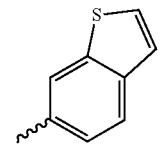 | 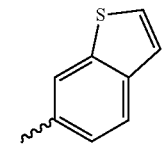 | — | — |
| 140 | S | CH | O | 0 | 0 | 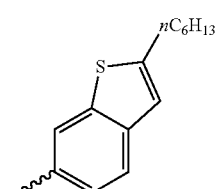 | 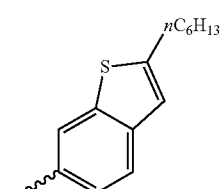 | — | — |
TABLE 8
| | | | | | | | | | |
|---|---|---|---|---|---|---|---|---|---|
| 141 | S | CH | O | 0 | 0 | 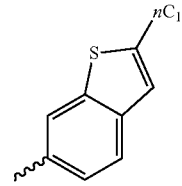 | 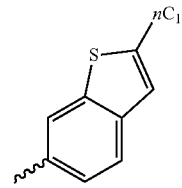 | — | — |
| 142 | S | CH | O | 0 | 0 | 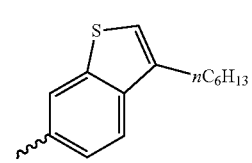 | 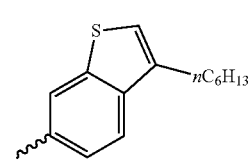 | — | — |
| 143 | S | CH | O | 0 | 0 | 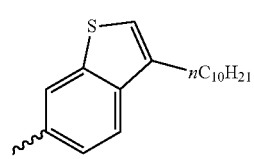 | 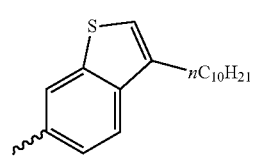 | — | — |
| 144 | S | CH | O | 0 | 0 | 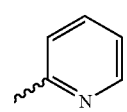 | 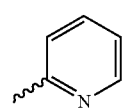 | — | — |
| 145 | S | CH | O | 0 | 0 | 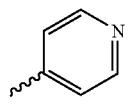 | 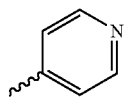 | — | — |
| 146 | S | CH | O | 0 | 0 | 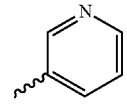 | 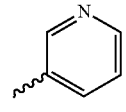 | — | — |

TABLE 8-continued
| | | | | | | | | | |
|---|---|---|---|---|---|---|---|---|---|
| 147 | S | CH | O | 0 | 0 | 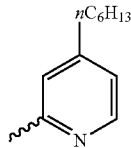 | 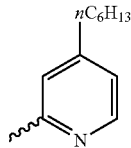 | — | — |
| 148 | S | CH | O | 0 | 0 | 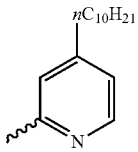 | 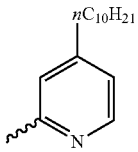 | — | — |
| 149 | S | CH | O | 0 | 0 | 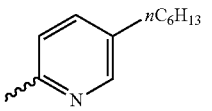 | 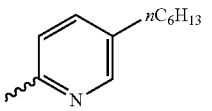 | — | — |
| 150 | S | CH | O | 0 | 0 | 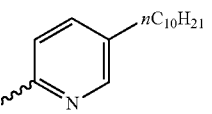 | 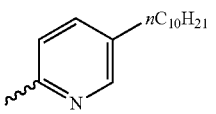 | — | — |
| 151 | S | CH | O | 0 | 0 | 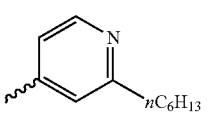 | 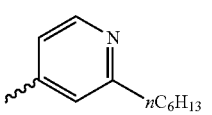 | — | — |
| 152 | S | CH | O | 0 | 0 | 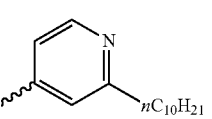 | 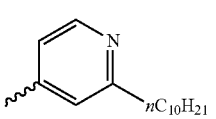 | — | — |
| 153 | S | CH | O | 0 | 0 | 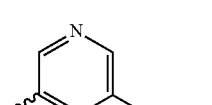 | 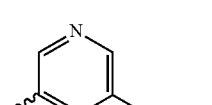 | — | — |
| 154 | S | CH | O | 0 | 0 | 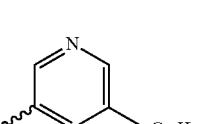 | 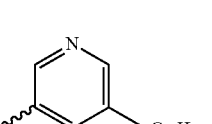 | — | — |
| 155 | S | CH | O | 2 | 2 | H | H | n-C6H13 | n-C6H13 |
| 156 | S | CH | O | 2 | 2 | H | H | n-C10H21 | n-C10H21 |
| 157 | S | CH | S | 0 | 0 | OCH$_3$ | OCH$_3$ | — | — |
| 158 | S | CH | S | 0 | 0 | O-n-C$_4$H$_9$ | O-n-C$_4$H$_9$ | — | — |
| 159 | S | CH | S | 0 | 0 | O-n-C$_5$H$_{11}$ | O-n-C$_5$H$_{11}$ | — | — |
| 160 | S | CH | S | 0 | 0 | O-n-C$_6$H$_{13}$ | O-n-C$_6$H$_{13}$ | — | — |
TABLE 9
| | | | | | | | | | |
|---|---|---|---|---|---|---|---|---|---|
| 161 | S | CH | S | 0 | 0 | O-n-C$_7$H$_{15}$ | O-n-C$_7$H$_{15}$ | — | — |
| 162 | S | CH | S | 0 | 0 | O-n-C$_8$H$_{17}$ | O-n-C$_8$H$_{17}$ | — | — |
| 163 | S | CH | S | 0 | 0 | O-n-C$_9$H$_{19}$ | O-n-C$_9$H$_{19}$ | — | — |
| 164 | S | CH | S | 0 | 0 | O-n-C$_{10}$H$_{21}$ | O-n-C$_{10}$H$_{21}$ | — | — |
| 165 | S | CH | S | 0 | 0 | O-n-C$_{11}$H$_{23}$ | O-n-C$_{11}$H$_{23}$ | — | — |
| 166 | S | CH | S | 0 | 0 | O-n-C$_{12}$H$_{25}$ | O-n-C$_{12}$H$_{25}$ | — | — |
| 167 | S | CH | S | 0 | 0 | 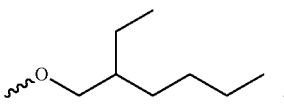 | 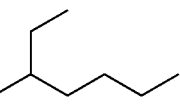 | — | — |
| 168 | S | CH | S | 0 | 0 | 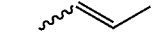 |  | — | — |

TABLE 9-continued
| | | | | | | | | | |
|---|---|---|---|---|---|---|---|---|---|
| 169 | S | CH | S | 0 | 0 |  |  | — | — |
| 170 | S | CH | S | 0 | 0 | 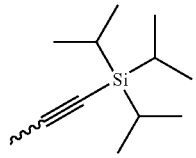 | 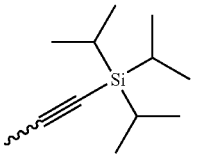 | — | — |
| 171 | S | CH | S | 0 | 0 | 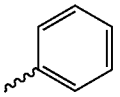 | 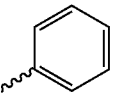 | — | — |
| 172 | S | CH | S | 0 | 0 | 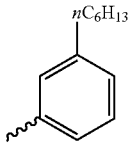 | 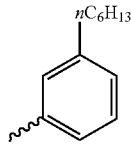 | — | — |
| 173 | S | CH | S | 0 | 0 | 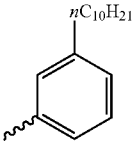 | 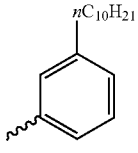 | — | — |
| 174 | S | CH | S | 0 | 0 | 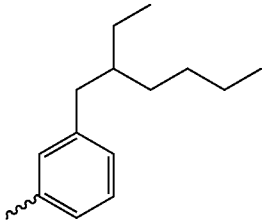 | 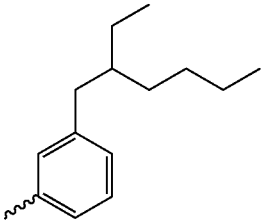 | — | — |
| 175 | S | CH | S | 0 | 0 | 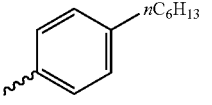 | 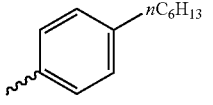 | — | — |
| 176 | S | CH | S | 0 | 0 | 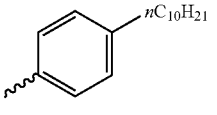 | 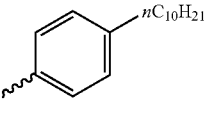 | — | — |
| 177 | S | CH | S | 0 | 0 | 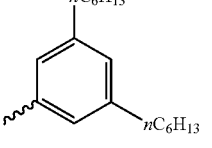 | 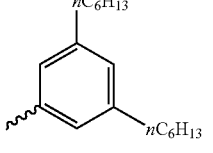 | — | — |
| 178 | S | CH | S | 0 | 0 | 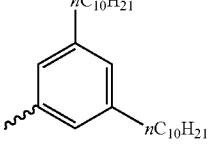 | 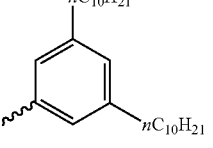 | — | — |
| 179 | S | CH | S | 0 | 0 | 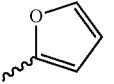 | 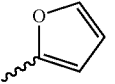 | — | — |

TABLE 9-continued

| 180 | S | CH | S | 0 | 0 | | | — | — |

TABLE 10

| 181 | S | CH | S | 0 | 0 | | | — | — |
| 182 | S | CH | S | 0 | 0 | | | — | — |
| 183 | S | CH | S | 0 | 0 | | | — | — |
| 184 | S | CH | S | 0 | 0 | | | — | — |
| 185 | S | CH | S | 0 | 0 | | | — | — |
| 186 | S | CH | S | 0 | 0 | | | — | — |
| 187 | S | CH | S | 0 | 0 | | | — | — |
| 188 | S | CH | S | 0 | 0 | | | — | — |
| 189 | S | CH | S | 0 | 0 | | | — | — |
| 190 | S | CH | S | 0 | 0 | | | — | — |
| 191 | S | CH | S | 0 | 0 | | | — | — |
| 192 | S | CH | S | 0 | 0 | | | — | — |
| 193 | S | CH | S | 0 | 0 | | | — | — |
| 194 | S | CH | S | 0 | 0 | | | — | — |
| 195 | S | CH | S | 0 | 0 | | | — | — |
| 196 | S | CH | S | 0 | 0 | | | — | — |
| 197 | S | CH | S | 0 | 0 | | | — | — |
| 198 | S | CH | S | 0 | 0 | | | — | — |
| 199 | S | CH | S | 0 | 0 | | | — | — |
| 200 | S | CH | S | 0 | 0 | | | — | — |

TABLE 11

| 201 | S | CH | S | 0 | 0 | | | — | — |
| 202 | S | CH | S | 0 | 0 | | | — | — |

TABLE 11-continued
| | | | | | | | | |
|---|---|---|---|---|---|---|---|---|
| 203 | S | CH | S | 0 0 | 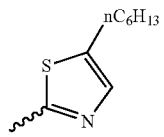 | 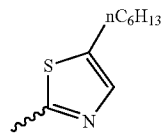 | — | — |
| 204 | S | CH | S | 0 0 | 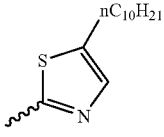 | 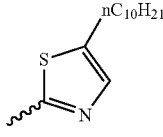 | — | — |
| 205 | S | CH | S | 0 0 | 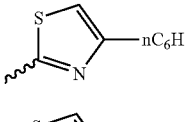 | 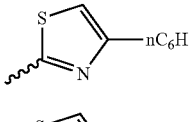 | — | — |
| 206 | S | CH | S | 0 0 | 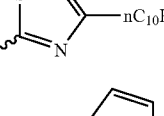 | 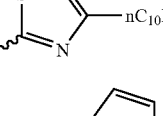 | — | — |
| 207 | S | CH | S | 0 0 | 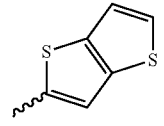 | 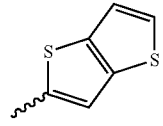 | — | — |
| 208 | S | CH | S | 0 0 | 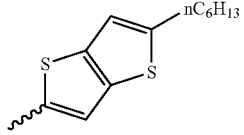 | 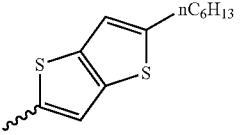 | — | — |
| 209 | S | CH | S | 0 0 | 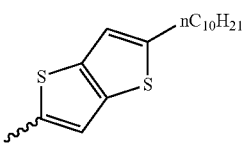 | 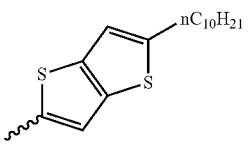 | — | — |
| 210 | S | CH | S | 0 0 | 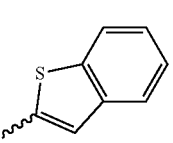 | 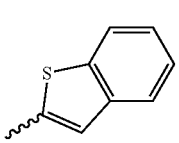 | — | — |
| 211 | S | CH | S | 0 0 | 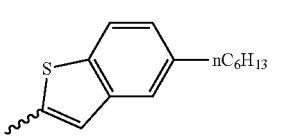 | 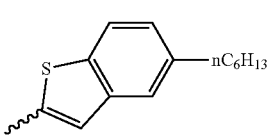 | — | — |
| 212 | S | CH | S | 0 0 | 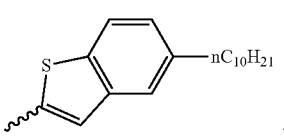 | 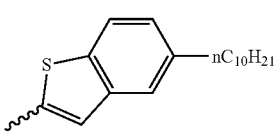 | — | — |
| 213 | S | CH | S | 0 0 | 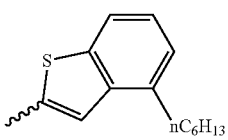 | 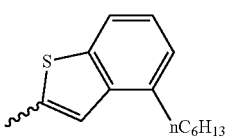 | — | — |
| 214 | S | CH | S | 0 0 | 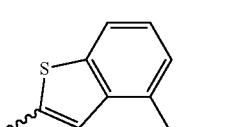 | 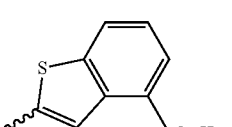 | — | — |

TABLE 11-continued

| | | | | | | Ar1 | Ar2 | | |
|---|---|---|---|---|---|---|---|---|---|
| 215 | S | CH | S | 0 | 0 | benzothiophene-6-yl | benzothiophene-6-yl | — | — |
| 216 | S | CH | S | 0 | 0 | 2-nC$_6$H$_{13}$-benzothiophene-6-yl | 2-nC$_6$H$_{13}$-benzothiophene-6-yl | — | — |
| 217 | S | CH | S | 0 | 0 | 2-nC$_{10}$H$_{21}$-benzothiophene-6-yl | 2-nC$_{10}$H$_{21}$-benzothiophene-6-yl | — | — |
| 218 | S | CH | S | 0 | 0 | 3-nC$_6$H$_{13}$-benzothiophene-6-yl | 3-nC$_6$H$_{13}$-benzothiophene-6-yl | — | — |
| 219 | S | CH | S | 0 | 0 | 3-nC$_{10}$H$_{21}$-benzothiophene-6-yl | 3-nC$_{10}$H$_{21}$-benzothiophene-6-yl | — | — |
| 220 | S | CH | S | 0 | 0 | pyridin-2-yl | pyridin-2-yl | — | — |

TABLE 12

| | | | | | | Ar1 | Ar2 | | |
|---|---|---|---|---|---|---|---|---|---|
| 221 | S | CH | S | 0 | 0 | pyridin-4-yl | pyridin-4-yl | — | — |
| 222 | S | CH | S | 0 | 0 | pyridin-3-yl | pyridin-3-yl | — | — |
| 223 | S | CH | S | 0 | 0 | 4-nC$_6$H$_{13}$-pyridin-2-yl | 4-nC$_6$H$_{13}$-pyridin-2-yl | — | — |
| 224 | S | CH | S | 0 | 0 | 4-nC$_{10}$H$_{21}$-pyridin-2-yl | 4-nC$_{10}$H$_{21}$-pyridin-2-yl | — | — |

TABLE 12-continued

| # | | | | | | | | | |
|---|---|---|---|---|---|---|---|---|---|
| 225 | S | CH | S | 0 | 0 | 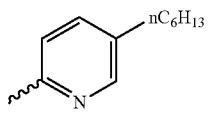 nC$_6$H$_{13}$ | 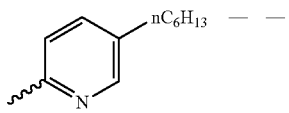 nC$_6$H$_{13}$ | — | — |
| 226 | S | CH | S | 0 | 0 | 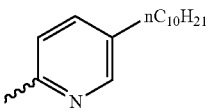 nC$_{10}$H$_{21}$ | 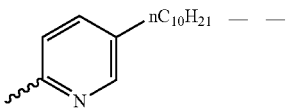 nC$_{10}$H$_{21}$ | — | — |
| 227 | S | CH | S | 0 | 0 | 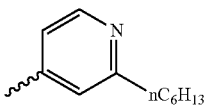 nC$_6$H$_{13}$ | 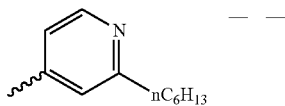 nC$_6$H$_{13}$ | — | — |
| 228 | S | CH | S | 0 | 0 | 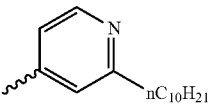 nC$_{10}$H$_{21}$ | 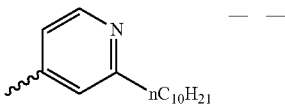 nC$_{10}$H$_{21}$ | — | — |
| 229 | S | CH | S | 0 | 0 | 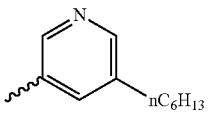 nC$_6$H$_{13}$ | 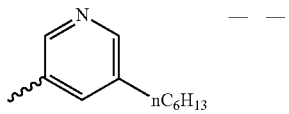 nC$_6$H$_{13}$ | — | — |
| 230 | S | CH | S | 0 | 0 | 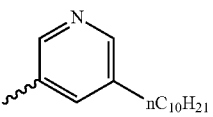 nC$_{10}$H$_{21}$ | 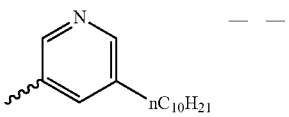 nC$_{10}$H$_{21}$ | — | — |
| 231 | S | S | CH | 0 | 0 | CH$_3$ | CH$_3$ | — | — |
| 232 | S | S | CH | 0 | 0 | n—C$_4$H$_9$ | n—C$_4$H$_9$ | — | — |
| 233 | S | S | CH | 0 | 0 | n—C$_5$H$_{11}$ | n—C$_5$H$_{11}$ | — | — |
| 234 | S | S | CH | 0 | 0 | n—C$_6$H$_{13}$ | n—C$_6$H$_{13}$ | — | — |
| 235 | S | S | CH | 0 | 0 | n—C$_7$H$_{15}$ | n—C$_7$H$_{15}$ | — | — |
| 236 | S | S | CH | 0 | 0 | n—C$_8$H$_{17}$ | n—C$_8$H$_{17}$ | — | — |
| 237 | S | S | CH | 0 | 0 | n—C$_9$H$_{19}$ | n—C$_9$H$_{19}$ | — | — |
| 238 | S | S | CH | 0 | 0 | n—C$_{10}$H$_{21}$ | n—C$_{10}$H$_{21}$ | — | — |
| 239 | S | S | CH | 0 | 0 | n—C$_{11}$H$_{23}$ | n—C$_{11}$H$_{23}$ | — | — |
| 240 | S | S | CH | 0 | 0 | n—C$_{12}$H$_{25}$ | n—C$_{12}$H$_{25}$ | — | — |

TABLE 13

| 241 | S | S | CH | 0 | 0 | 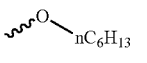 O—nC$_6$H$_{13}$ | 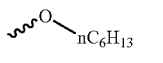 O—nC$_6$H$_{13}$ | — | — |
|---|---|---|---|---|---|---|---|---|---|
| 242 | S | S | CH | 0 | 0 | 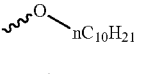 O—nC$_{10}$H$_{21}$ | 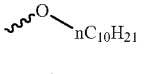 O—nC$_{10}$H$_{21}$ | — | — |
| 243 | S | S | CH | 0 | 0 | 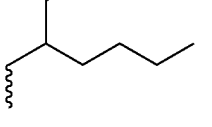 | 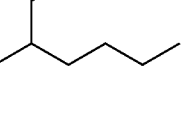 | — | — |
| 244 | S | S | CH | 0 | 0 | 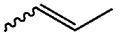 | 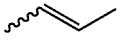 | — | — |
| 245 | S | S | CH | 0 | 0 |  |  | — | — |

TABLE 13-continued
| 246 | S | S | CH | 0 | 0 | 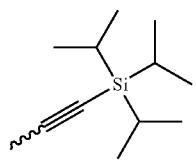 | 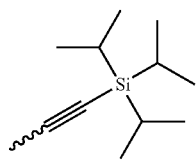 | — | — |
| 247 | S | S | CH | 0 | 0 | 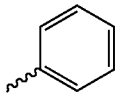 | 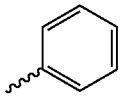 | — | — |
| 248 | S | S | CH | 0 | 0 | 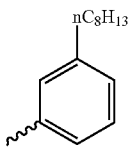 | 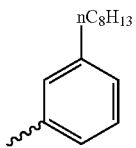 | — | — |
| 249 | S | S | CH | 0 | 0 | 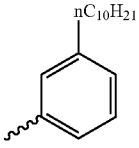 | 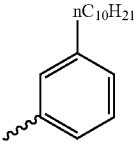 | — | — |
| 250 | S | S | CH | 0 | 0 | 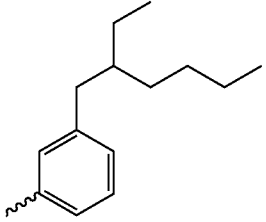 | 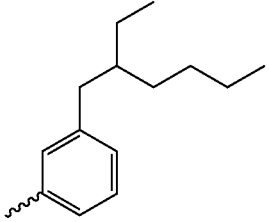 | — | — |
| 251 | S | S | CH | 0 | 0 | 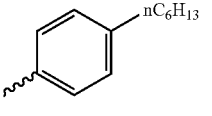 | 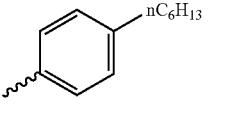 | — | — |
| 252 | S | S | CH | 0 | 0 | 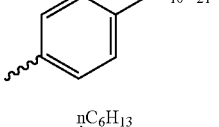 | 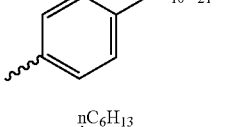 | — | — |
| 253 | S | S | CH | 0 | 0 | 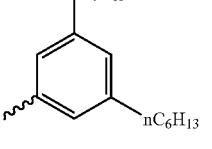 | 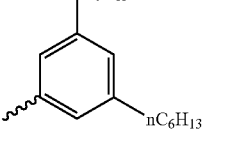 | — | — |
| 254 | S | S | CH | 0 | 0 | 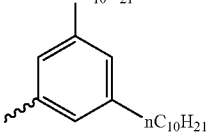 | 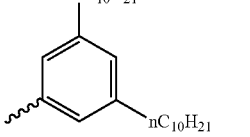 | — | — |
| 255 | S | S | CH | 0 | 0 | 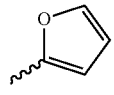 | 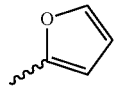 | — | — |
| 256 | S | S | CH | 0 | 0 | 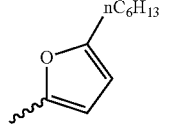 | 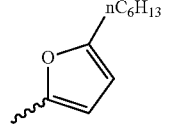 | — | — |

TABLE 13-continued

| 257 | S | S | CH | 0 | 0 | ⌇⟨furan⟩-nC10H21 | ⌇⟨furan⟩-nC10H21 | — | — |
| 258 | S | S | CH | 0 | 0 | ⌇⟨furan⟩-nC6H13 | ⌇⟨furan⟩-nC6H13 | — | — |
| 259 | S | S | CH | 0 | 0 | ⌇⟨furan⟩-nC10H21 | ⌇⟨furan⟩-nC10H21 | — | — |
| 260 | S | S | CH | 0 | 0 | ⌇⟨pyrrole⟩ | ⌇⟨pyrrole⟩ | — | — |

TABLE 14

| 261 | S | S | CH | 0 | 0 | ⌇⟨N-Me-pyrrole⟩-nC6H13 | ⌇⟨N-Me-pyrrole⟩-nC6H13 | — | — |
| 262 | S | S | CH | 0 | 0 | nC6H13-⟨N-pyrrole⟩ | nC6H13-⟨N-pyrrole⟩ | — | — |
| 263 | S | S | CH | 0 | 0 | nC10H21-⟨N-pyrrole⟩ | nC10H21-⟨N-pyrrole⟩ | — | — |
| 264 | S | S | CH | 0 | 0 | ⌇⟨thiophene⟩ | ⌇⟨thiophene⟩ | — | — |
| 265 | S | S | CH | 0 | 0 | ⌇⟨thiophene⟩ | ⌇⟨thiophene⟩ | — | — |
| 266 | S | S | CH | 0 | 0 | ⌇⟨thiophene⟩-nC5H11 | ⌇⟨thiophene⟩-nC5H11 | — | — |
| 267 | S | S | CH | 0 | 0 | ⌇⟨thiophene⟩-nC6H13 | ⌇⟨thiophene⟩-nC6H13 | — | — |
| 268 | S | S | CH | 0 | 0 | ⌇⟨thiophene⟩-nC8H17 | ⌇⟨thiophene⟩-nC8H17 | — | — |
| 269 | S | S | CH | 0 | 0 | ⌇⟨thiophene⟩-nC10H21 | ⌇⟨thiophene⟩-nC10H21 | — | — |

TABLE 14-continued

| # | | | | | | Ar1 | Ar2 | | |
|---|---|---|---|---|---|---|---|---|---|
| 270 | S | S | CH | 0 | 0 | 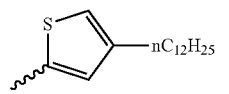 thiophene-nC$_{12}$H$_{25}$ | 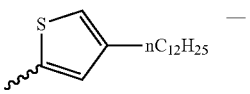 thiophene-nC$_{12}$H$_{25}$ | — | — |
| 271 | S | S | CH | 0 | 0 | 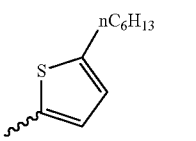 thiophene-nC$_6$H$_{13}$ | 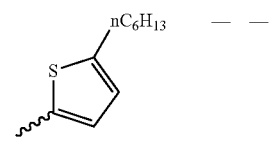 thiophene-nC$_6$H$_{13}$ | — | — |
| 272 | S | S | CH | 0 | 0 | 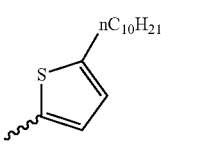 thiophene-nC$_{10}$H$_{21}$ | 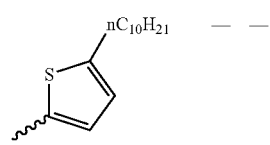 thiophene-nC$_{10}$H$_{21}$ | — | — |
| 273 | S | S | CH | 0 | 0 | 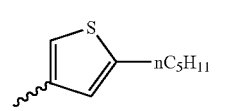 thiophene-nC$_5$H$_{11}$ | 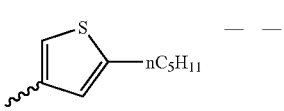 thiophene-nC$_5$H$_{11}$ | — | — |
| 274 | S | S | CH | 0 | 0 | 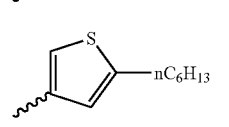 thiophene-nC$_6$H$_{13}$ | 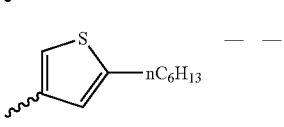 thiophene-nC$_6$H$_{13}$ | — | — |
| 275 | S | S | CH | 0 | 0 | 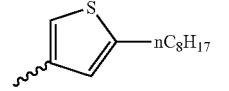 thiophene-nC$_8$H$_{17}$ | 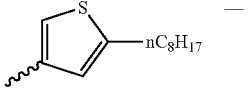 thiophene-nC$_8$H$_{17}$ | — | — |
| 276 | S | S | CH | 0 | 0 | 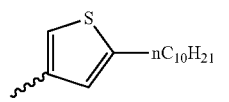 thiophene-nC$_{10}$H$_{21}$ | 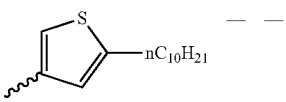 thiophene-nC$_{10}$H$_{21}$ | — | — |
| 277 | S | S | CH | 0 | 0 | 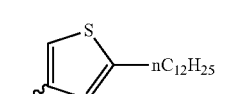 thiophene-nC$_{12}$H$_{25}$ | 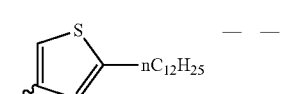 thiophene-nC$_{12}$H$_{25}$ | — | — |
| 278 | S | S | CH | 0 | 0 | 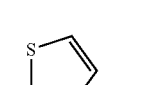 thiazole | 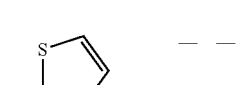 thiazole | — | — |
| 279 | S | S | CH | 0 | 0 | 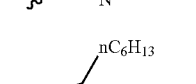 thiazole-nC$_6$H$_{13}$ | 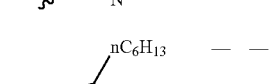 thiazole-nC$_6$H$_{13}$ | — | — |
| 280 | S | S | CH | 0 | 0 | 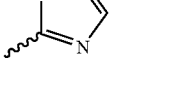 thiazole-nC$_{10}$H$_{21}$ | 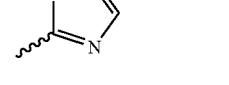 thiazole-nC$_{10}$H$_{21}$ | — | — |

TABLE 15

| # | | | | | | Ar1 | Ar2 | | |
|---|---|---|---|---|---|---|---|---|---|
| 281 | S | S | CH | 0 | 0 | 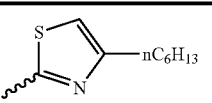 thiazole-nC$_6$H$_{13}$ | 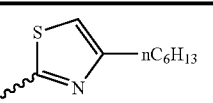 thiazole-nC$_6$H$_{13}$ | — | — |
| 282 | S | S | CH | 0 | 0 | 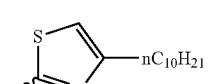 thiazole-nC$_{10}$H$_{21}$ | 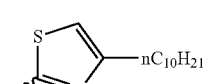 thiazole-nC$_{10}$H$_{21}$ | — | — |

TABLE 15-continued

| | | | | | | Structure 1 | Structure 2 | | |
|---|---|---|---|---|---|---|---|---|---|
| 283 | S | S | CH | 0 | 0 | thieno[3,2-b]thiophene | thieno[3,2-b]thiophene | — | — |
| 284 | S | S | CH | 0 | 0 | thieno[3,2-b]thiophene-nC₆H₁₃ | thieno[3,2-b]thiophene-nC₆H₁₃ | — | — |
| 285 | S | S | CH | 0 | 0 | thieno[3,2-b]thiophene-nC₁₀H₂₁ | thieno[3,2-b]thiophene-nC₁₀H₂₁ | — | — |
| 286 | S | S | CH | 0 | 0 | benzothiophene | benzothiophene | — | — |
| 287 | S | S | CH | 0 | 0 | benzothiophene-nC₆H₁₃ | benzothiophene-nC₆H₁₃ | — | — |
| 288 | S | S | CH | 0 | 0 | benzothiophene-nC₁₀H₂₁ | benzothiophene-nC₁₀H₂₁ | — | — |
| 289 | S | S | CH | 0 | 0 | benzothiophene-nC₆H₁₃ | benzothiophene-nC₆H₁₃ | — | — |
| 290 | S | S | CH | 0 | 0 | benzothiophene-nC₁₀H₂₁ | benzothiophene-nC₁₀H₂₁ | — | — |
| 291 | S | S | CH | 0 | 0 | benzothiophene | benzothiophene | — | — |
| 292 | S | S | CH | 0 | 0 | benzothiophene-nC₆H₁₃ | benzothiophene-nC₆H₁₃ | — | — |

TABLE 15-continued
| 293 | S | S | CH | 0 | 0 | 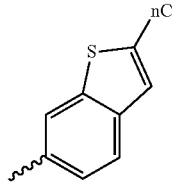 | 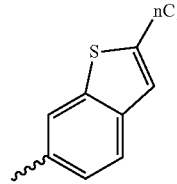 | — | — |
| 294 | S | S | CH | 0 | 0 | 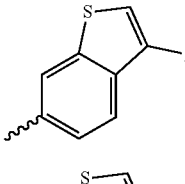 | 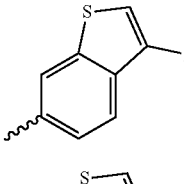 | — | — |
| 295 | S | S | CH | 0 | 0 | 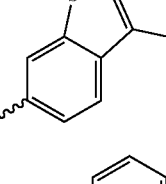 | 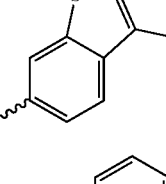 | — | — |
| 296 | S | S | CH | 0 | 0 | 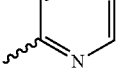 | 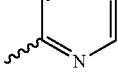 | — | — |
| 297 | S | S | CH | 0 | 0 | 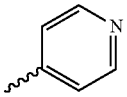 | 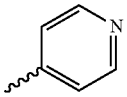 | — | — |
| 298 | S | S | CH | 0 | 0 | 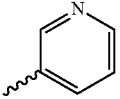 | 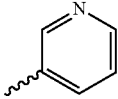 | — | — |
| 299 | S | S | CH | 0 | 0 | 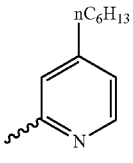 | 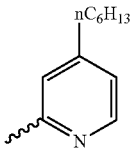 | — | — |
| 300 | S | S | CH | 0 | 0 | 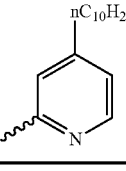 | 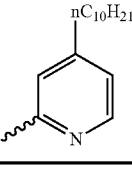 | — | — |
TABLE 16
| 301 | S | S | CH | 0 | 0 | 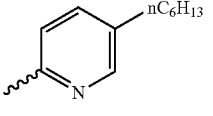 | 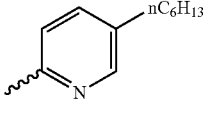 | — | — |
| 302 | S | S | CH | 0 | 0 | 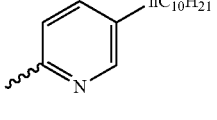 | 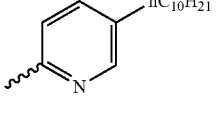 | — | — |
| 303 | S | S | CH | 0 | 0 | 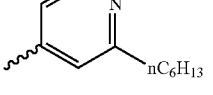 | 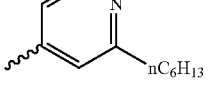 | — | — |

TABLE 16-continued
| | | | | | | | | | |
|---|---|---|---|---|---|---|---|---|---|
| 304 | S | S | CH | 0 | 0 | 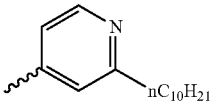 | 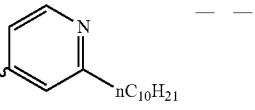 | — | — |
| 305 | S | S | CH | 0 | 0 | 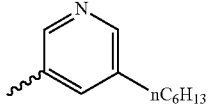 | 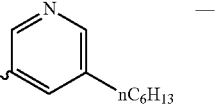 | — | — |
| 306 | S | S | CH | 0 | 0 | 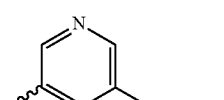 | 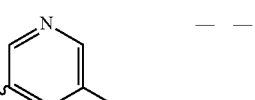 | — | — |
| 307 | S | S | CH | 0 | 0 | $CH_3$ | $CH_3$ | — | — |
| 308 | S | O | CH | 0 | 0 | $n\text{-}C_4H_9$ | $n\text{-}C_4H_9$ | — | — |
| 309 | S | O | CH | 0 | 0 | $n\text{-}C_5H_{11}$ | $n\text{-}C_5H_{11}$ | — | — |
| 310 | S | O | CH | 0 | 0 | $n\text{-}C_6H_{13}$ | $n\text{-}C_6H_{13}$ | — | — |
| 311 | S | O | CH | 0 | 0 | $n\text{-}C_7H_{15}$ | $n\text{-}C_7H_{15}$ | — | — |
| 312 | S | O | CH | 0 | 0 | $n\text{-}C_8H_{17}$ | $n\text{-}C_8H_{17}$ | — | — |
| 313 | S | O | CH | 0 | 0 | $n\text{-}C_9H_{19}$ | $n\text{-}C_9H_{19}$ | — | — |
| 314 | S | O | CH | 0 | 0 | $n\text{-}C_{10}H_{21}$ | $n\text{-}C_{10}H_{21}$ | — | — |
| 315 | S | O | CH | 0 | 0 | $n\text{-}C_{11}H_{23}$ | $n\text{-}C_{11}H_{23}$ | — | — |
| 316 | S | O | CH | 0 | 0 | $n\text{-}C_{12}H_{25}$ | $n\text{-}C_{12}H_{25}$ | — | — |
| 317 | S | O | CH | 0 | 0 | 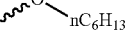 | 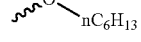 | — | — |
| 318 | S | O | CH | 0 | 0 | 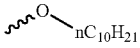 | 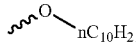 | — | — |
| 319 | S | O | CH | 0 | 0 | 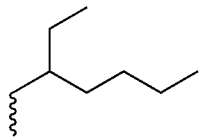 | 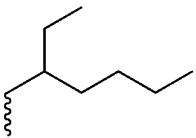 | — | — |
| 320 | S | O | CH | 0 | 0 | 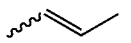 | 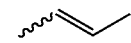 | — | — |
TABLE 17
| | | | | | | | | | |
|---|---|---|---|---|---|---|---|---|---|
| 321 | S | O | CH | 0 | 0 |  |  | — | — |
| 322 | S | O | CH | 0 | 0 | 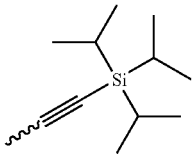 | 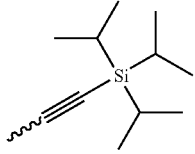 | — | — |
| 323 | S | O | CH | 0 | 0 | 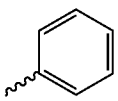 | 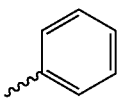 | — | — |
| 324 | S | O | CH | 0 | 0 | 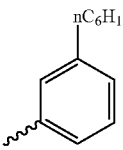 | 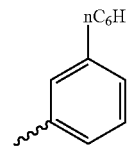 | — | — |

TABLE 17-continued

| 325 | S | O | CH | 0 | 0 | 3-(nC₁₀H₂₁)-phenyl | 3-(nC₁₀H₂₁)-phenyl | — | — |
| 326 | S | O | CH | 0 | 0 | 3-(2-ethylhexyl)-phenyl | 3-(2-ethylhexyl)-phenyl | — | — |
| 327 | S | O | CH | 0 | 0 | 4-(nC₆H₁₃)-phenyl | 4-(nC₆H₁₃)-phenyl | — | — |
| 328 | S | O | CH | 0 | 0 | 4-(nC₁₀H₂₁)-phenyl | 4-(nC₁₀H₂₁)-phenyl | — | — |
| 329 | S | O | CH | 0 | 0 | 3,5-di(nC₆H₁₃)-phenyl | 3,5-di(nC₆H₁₃)-phenyl | — | — |
| 330 | S | O | CH | 0 | 0 | 3,5-di(nC₁₀H₂₁)-phenyl | 3,5-di(nC₁₀H₂₁)-phenyl | — | — |
| 331 | S | O | CH | 0 | 0 | furan-2-yl | furan-2-yl | — | — |
| 332 | S | O | CH | 0 | 0 | 5-(nC₆H₁₃)-furan-2-yl | 5-(nC₆H₁₃)-furan-2-yl | — | — |
| 333 | S | O | CH | 0 | 0 | 5-(nC₁₀H₂₁)-furan-2-yl | 5-(nC₁₀H₂₁)-furan-2-yl | — | — |
| 334 | S | O | CH | 0 | 0 | 4-(nC₆H₁₃)-furan-2-yl | 4-(nC₆H₁₃)-furan-2-yl | — | — |
| 335 | S | O | CH | 0 | 0 | 4-(nC₁₀H₂₁)-furan-2-yl | 4-(nC₁₀H₂₁)-furan-2-yl | — | — |

TABLE 17-continued

| | | | | | Ar1 | Ar2 | | |
|---|---|---|---|---|---|---|---|---|
| 336 | S | O | CH | 0 | 0 | pyrrole (NH, 2-yl) | pyrrole (NH, 2-yl) | — — |
| 337 | S | O | CH | 0 | 0 | 1-methyl-5-(nC6H13)-pyrrol-2-yl | 1-methyl-5-(nC6H13)-pyrrol-2-yl | — — |
| 338 | S | O | CH | 0 | 0 | 1-(nC6H13)-pyrrol-2-yl | 1-(nC6H13)-pyrrol-2-yl | — — |
| 339 | S | O | CH | 0 | 0 | 1-(nC10H21)-pyrrol-2-yl | 1-(nC10H21)-pyrrol-2-yl | — — |
| 340 | S | O | CH | 0 | 0 | thiophen-2-yl | thiophen-2-yl | — — |

TABLE 18

| | | | | | Ar1 | Ar2 | | |
|---|---|---|---|---|---|---|---|---|
| 341 | S | O | CH | 0 | 0 | thiophen-3-yl | thiophen-3-yl | — — |
| 342 | S | O | CH | 0 | 0 | 4-(nC5H11)-thiophen-2-yl | 4-(nC5H11)-thiophen-2-yl | — — |
| 343 | S | O | CH | 0 | 0 | 4-(nC6H13)-thiophen-2-yl | 4-(nC6H13)-thiophen-2-yl | — — |
| 344 | S | O | CH | 0 | 0 | 4-(nC8H17)-thiophen-2-yl | 4-(nC8H17)-thiophen-2-yl | — — |
| 345 | S | O | CH | 0 | 0 | 4-(nC10H21)-thiophen-2-yl | 4-(nC10H21)-thiophen-2-yl | — — |
| 346 | S | O | CH | 0 | 0 | 4-(nC12H25)-thiophen-2-yl | 4-(nC12H25)-thiophen-2-yl | — — |
| 347 | S | O | CH | 0 | 0 | 5-(nC6H13)-thiophen-2-yl | 5-(nC6H13)-thiophen-2-yl | — — |
| 348 | S | O | CH | 0 | 0 | 5-(nC10H21)-thiophen-2-yl | 5-(nC10H21)-thiophen-2-yl | — — |

TABLE 18-continued
| | | | | | | | | | |
|---|---|---|---|---|---|---|---|---|---|
| 349 | S | O | CH | 0 | 0 | 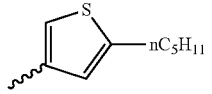 | 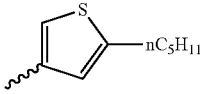 | — | — |
| 350 | S | O | CH | 0 | 0 | 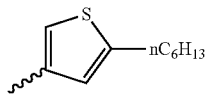 | 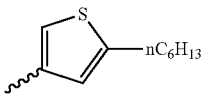 | — | — |
| 351 | S | O | CH | 0 | 0 | 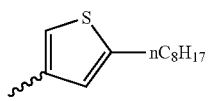 | 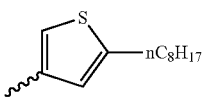 | — | — |
| 352 | S | O | CH | 0 | 0 | 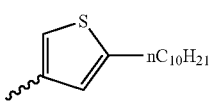 | 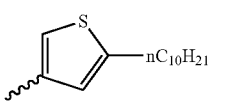 | — | — |
| 353 | S | O | CH | 0 | 0 | 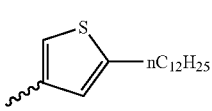 | 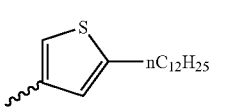 | — | — |
| 354 | S | O | CH | 0 | 0 | 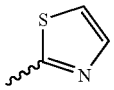 | 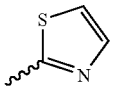 | — | — |
| 355 | S | O | CH | 0 | 0 | 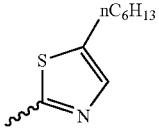 | 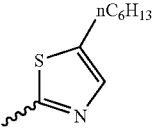 | — | — |
| 356 | S | O | CH | 0 | 0 | 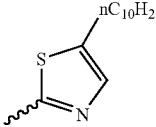 | 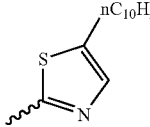 | — | — |
| 357 | S | O | CH | 0 | 0 | 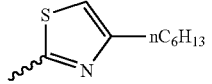 | 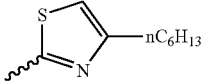 | — | — |
| 358 | S | O | CH | 0 | 0 | 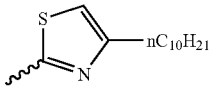 | 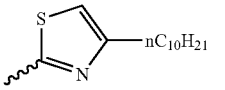 | — | — |
| 359 | S | O | CH | 0 | 0 | 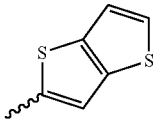 | 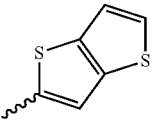 | — | — |
| 360 | S | O | CH | 0 | 0 | 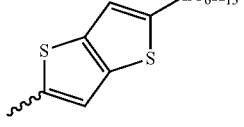 | 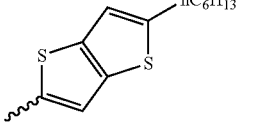 | — | — |

TABLE 19
| 361 | S | O | CH | 0 | 0 | 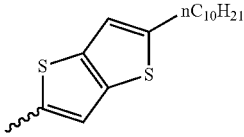 | 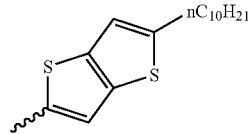 | — | — |
| 362 | S | O | CH | 0 | 0 | 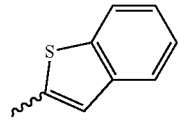 | 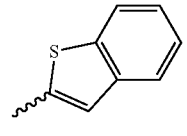 | — | — |
| 363 | S | O | CH | 0 | 0 | 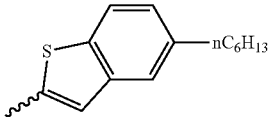 | 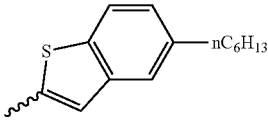 | — | — |
| 364 | S | O | CH | 0 | 0 | 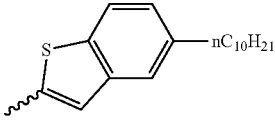 | 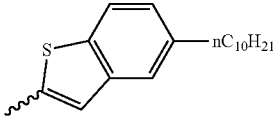 | — | — |
| 365 | S | O | CH | 0 | 0 | 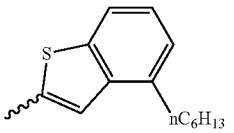 | 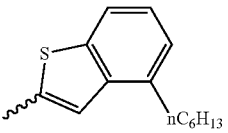 | — | — |
| 366 | S | O | CH | 0 | 0 | 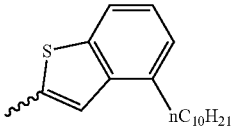 | 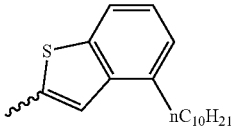 | — | — |
| 367 | S | O | CH | 0 | 0 | 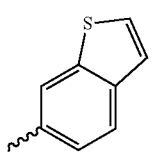 | 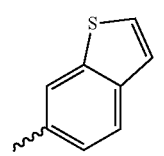 | — | — |
| 368 | S | O | CH | 0 | 0 | 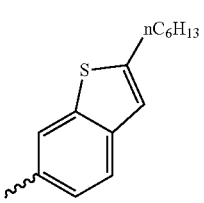 | 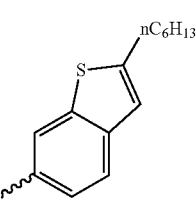 | — | — |
| 369 | S | O | CH | 0 | 0 | 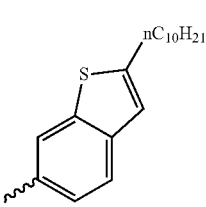 | 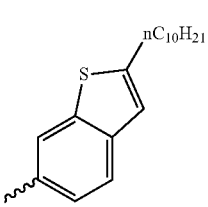 | — | — |
| 370 | S | O | CH | 0 | 0 | 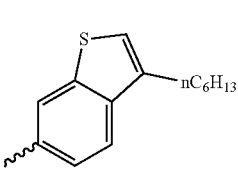 | 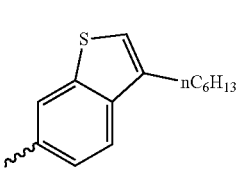 | — | — |

TABLE 19-continued
| # | | | | | | Structure 1 | Structure 2 | | |
|---|---|---|---|---|---|---|---|---|---|
| 371 | S | O | CH | 0 | 0 | 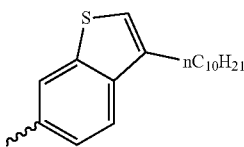 | 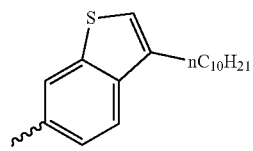 | — | — |
| 372 | S | O | CH | 0 | 0 | 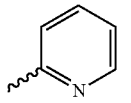 | 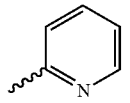 | — | — |
| 373 | S | O | CH | 0 | 0 | 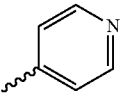 | 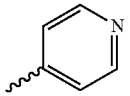 | — | — |
| 374 | S | O | CH | 0 | 0 | 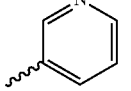 | 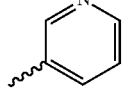 | — | — |
| 375 | S | O | CH | 0 | 0 | 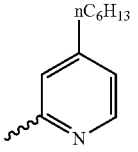 | 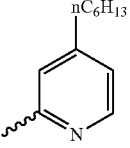 | — | — |
| 376 | S | O | CH | 0 | 0 | 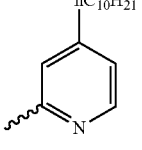 | 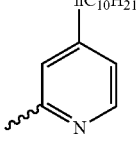 | — | — |
| 377 | S | O | CH | 0 | 0 | 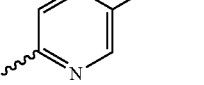 | 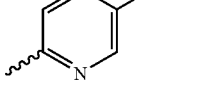 | — | — |
| 378 | S | O | CH | 0 | 0 | 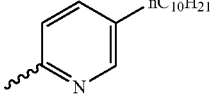 | 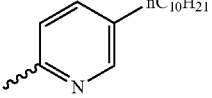 | — | — |
| 379 | S | O | CH | 0 | 0 | 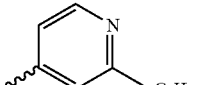 | 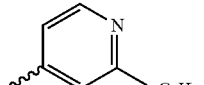 | — | — |
| 380 | S | O | CH | 0 | 0 | 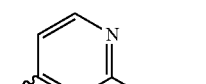 | 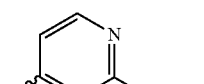 | — | — |
TABLE 20
| # | | | | | | Structure 1 | Structure 2 | | |
|---|---|---|---|---|---|---|---|---|---|
| 381 | S | S | CH | 0 | 0 | 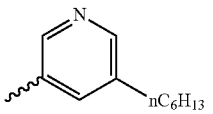 | 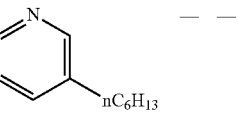 | — | — |
| 382 | S | S | CH | 0 | 0 | 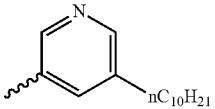 | 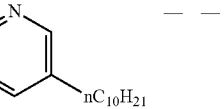 | — | — |

TABLE 20-continued
| | | | | | | | | | |
|---|---|---|---|---|---|---|---|---|---|
| 383 | S | S | N | 0 | 0 | CH$_3$ | CH$_3$ | — | — |
| 384 | S | S | N | 0 | 0 | n-C$_4$H$_9$ | n-C$_4$H$_9$ | — | — |
| 385 | S | S | N | 0 | 0 | n-C$_5$H$_{11}$ | n-C$_5$H$_{11}$ | — | — |
| 386 | S | S | N | 0 | 0 | n-C$_6$H$_{13}$ | n-C$_6$H$_{13}$ | — | — |
| 387 | S | S | N | 0 | 0 | n-C$_7$H$_{15}$ | n-C$_7$H$_{15}$ | — | — |
| 388 | S | S | N | 0 | 0 | n-C$_8$H$_{17}$ | n-C$_8$H$_{17}$ | — | — |
| 389 | S | S | N | 0 | 0 | n-C$_9$H$_{19}$ | n-C$_9$H$_{19}$ | — | — |
| 390 | S | S | N | 0 | 0 | n-C$_{10}$H$_{21}$ | n-C$_{10}$H$_{21}$ | — | — |
| 391 | S | S | N | 0 | 0 | n-C$_{11}$H$_{23}$ | n-C$_{11}$H$_{23}$ | — | — |
| 392 | S | S | N | 0 | 0 | n-C$_{12}$H$_{25}$ | n-C$_{12}$H$_{25}$ | — | — |
| 393 | S | S | N | 0 | 0 | 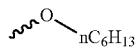 | 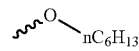 | — | — |
| 394 | S | S | N | 0 | 0 | 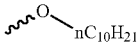 | 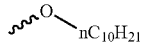 | — | — |
| 395 | S | S | N | 0 | 0 | 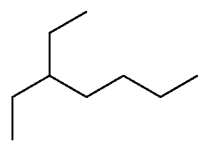 | 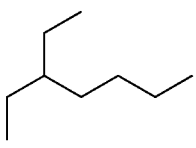 | — | — |
| 396 | S | S | N | 0 | 0 | 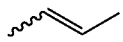 | 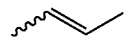 | — | — |
| 397 | S | S | N | 0 | 0 |  |  | — | — |
| 398 | S | S | N | 0 | 0 | 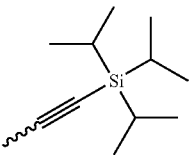 | 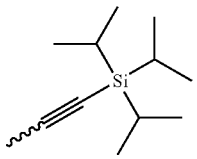 | — | — |
| 399 | S | S | N | 0 | 0 | 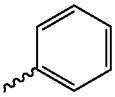 | 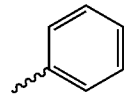 | — | — |
| 400 | S | S | N | 0 | 0 | 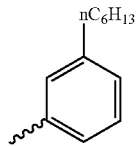 | 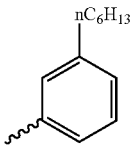 | — | — |
TABLE 21
| | | | | | | | | | |
|---|---|---|---|---|---|---|---|---|---|
| 401 | S | S | CH | 0 | 0 | 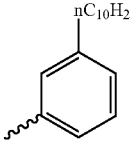 | 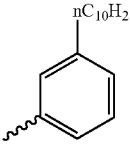 | — | — |
| 402 | S | S | CH | 0 | 0 | 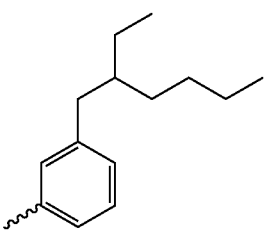 | 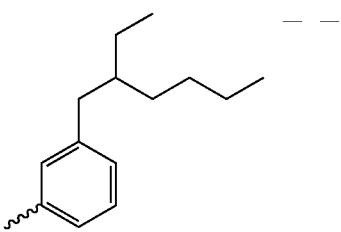 | — | — |

TABLE 21-continued

| # | | | | | | Ar1 | Ar2 | | |
|---|---|---|---|---|---|---|---|---|---|
| 403 | S | S | N | 0 | 0 | 4-(nC$_6$H$_{13}$NH)-phenyl | 4-(nC$_6$H$_{13}$NH)-phenyl | — | — |
| 404 | S | S | N | 0 | 0 | 4-(nC$_{10}$H$_{21}$NH)-phenyl | 4-(nC$_{10}$H$_{21}$NH)-phenyl | — | — |
| 405 | S | S | N | 0 | 0 | 3,5-bis(nC$_6$H$_{13}$)-phenyl | 3,5-bis(nC$_6$H$_{13}$)-phenyl | — | — |
| 406 | S | S | N | 0 | 0 | 3,5-bis(nC$_{10}$H$_{21}$)-phenyl | 3,5-bis(nC$_{10}$H$_{21}$)-phenyl | — | — |
| 407 | S | S | N | 0 | 0 | furan-2-yl | furan-2-yl | — | — |
| 408 | S | S | N | 0 | 0 | 5-(nC$_6$H$_{13}$)-furan-2-yl | 5-(nC$_6$H$_{13}$)-furan-2-yl | — | — |
| 409 | S | S | N | 0 | 0 | 5-(nC$_{10}$H$_{21}$)-furan-2-yl | 5-(nC$_{10}$H$_{21}$)-furan-2-yl | — | — |
| 410 | S | S | N | 0 | 0 | 4-(nC$_6$H$_{13}$)-furan-2-yl | 4-(nC$_6$H$_{13}$)-furan-2-yl | — | — |
| 411 | S | S | N | 0 | 0 | 4-(nC$_{10}$H$_{21}$)-furan-2-yl | 4-(nC$_{10}$H$_{21}$)-furan-2-yl | — | — |
| 412 | S | S | N | 0 | 0 | 1H-pyrrol-2-yl | 1H-pyrrol-2-yl | — | — |
| 413 | S | S | N | 0 | 0 | 1-methyl-5-(nC$_6$H$_{13}$)-pyrrol-2-yl | 1-methyl-5-(nC$_6$H$_{13}$)-pyrrol-2-yl | — | — |
| 414 | S | S | N | 0 | 0 | 1-(nC$_6$H$_{13}$)-pyrrol-2-yl | 1-(nC$_6$H$_{13}$)-pyrrol-2-yl | — | — |

TABLE 21-continued
| | | | | | | | | | |
|---|---|---|---|---|---|---|---|---|---|
| 415 | S | S | N | 0 | 0 | 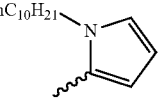 | 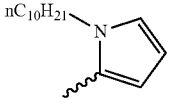 | — | — |
| 416 | S | S | N | 0 | 0 | 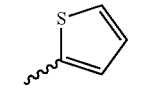 | 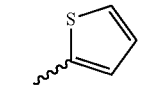 | — | — |
| 417 | S | S | N | 0 | 0 | 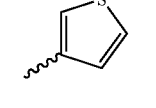 | 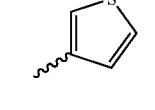 | — | — |
| 418 | S | S | N | 0 | 0 | 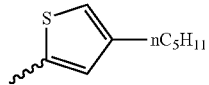 | 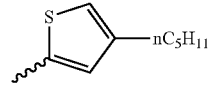 | — | — |
| 419 | S | S | N | 0 | 0 | 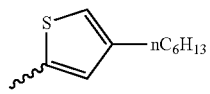 | 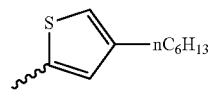 | — | — |
| 420 | S | S | N | 0 | 0 | 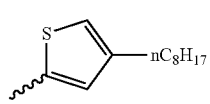 | 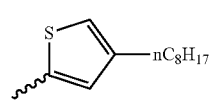 | — | — |
TABLE 22
| | | | | | | | | | |
|---|---|---|---|---|---|---|---|---|---|
| 421 | S | S | CH | 0 | 0 | 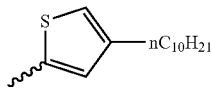 | 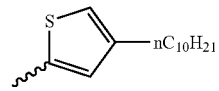 | — | — |
| 422 | S | S | CH | 0 | 0 | 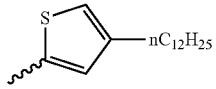 | 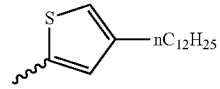 | — | — |
| 423 | S | S | N | 0 | 0 | 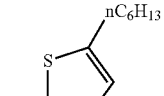 | 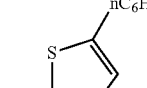 | — | — |
| 424 | S | S | N | 0 | 0 | 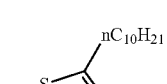 | 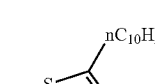 | — | — |
| 425 | S | S | N | 0 | 0 | 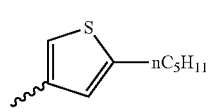 | 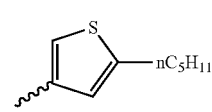 | — | — |
| 426 | S | S | N | 0 | 0 | 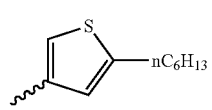 | 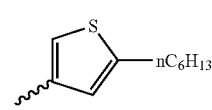 | — | — |
| 427 | S | S | N | 0 | 0 | 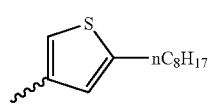 | 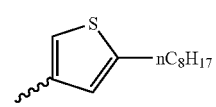 | — | — |

TABLE 22-continued
| 428 | S | S | N | 0 | 0 | 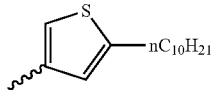 | 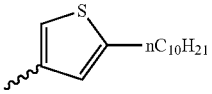 | — | — |
| 429 | S | S | N | 0 | 0 | 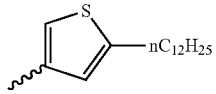 | 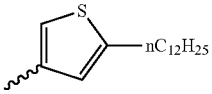 | — | — |
| 430 | S | S | N | 0 | 0 | 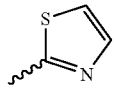 | 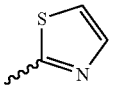 | — | — |
| 431 | S | S | N | 0 | 0 | 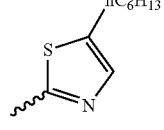 | 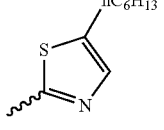 | — | — |
| 432 | S | S | N | 0 | 0 | 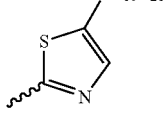 | 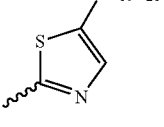 | — | — |
| 433 | S | S | N | 0 | 0 | 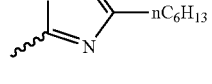 | 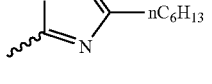 | — | — |
| 434 | S | S | N | 0 | 0 | 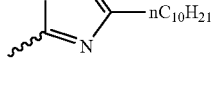 | 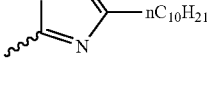 | — | — |
| 435 | S | S | N | 0 | 0 | 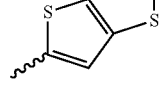 | 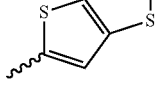 | — | — |
| 436 | S | S | N | 0 | 0 | 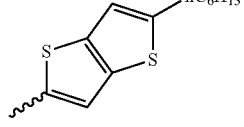 | 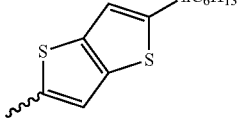 | — | — |
| 437 | S | S | N | 0 | 0 | 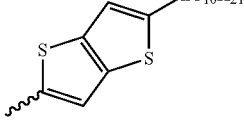 | 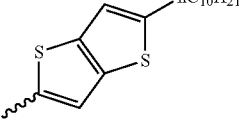 | — | — |
| 438 | S | S | N | 0 | 0 | 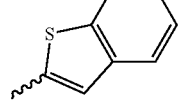 | 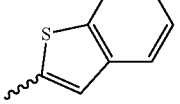 | — | — |
| 439 | S | S | N | 0 | 0 | 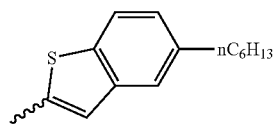 | 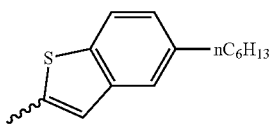 | — | — |

TABLE 22-continued

| 440 | S | S | N | 0 | 0 | [benzothiophene-nC10H21] | [benzothiophene-nC10H21] | — | — |

TABLE 23

| 441 | S | S | N | 0 | 0 | [benzothiophene-nC6H13] | [benzothiophene-nC6H13] | — | — |
| 442 | S | S | N | 0 | 0 | [benzothiophene-nC10H21] | [benzothiophene-nC10H21] | — | — |
| 443 | S | S | N | 0 | 0 | [benzothiophene] | [benzothiophene] | — | — |
| 444 | S | S | N | 0 | 0 | [benzothiophene-nC6H13] | [benzothiophene-nC6H13] | — | — |
| 445 | S | S | N | 0 | 0 | [benzothiophene-nC10H21] | [benzothiophene-nC10H21] | — | — |
| 446 | S | S | N | 0 | 0 | [benzothiophene-nC6H13] | [benzothiophene-nC6H13] | — | — |
| 447 | S | S | N | 0 | 0 | [benzothiophene-nC10H21] | [benzothiophene-nC10H21] | — | — |
| 448 | S | S | N | 0 | 0 | [pyridine] | [pyridine] | — | — |
| 449 | S | S | N | 0 | 0 | [pyridine] | [pyridine] | — | — |

TABLE 23-continued
| | | | | | | | | | |
|---|---|---|---|---|---|---|---|---|---|
| 450 | S | S | N | 0 | 0 | 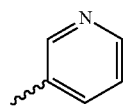 | 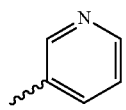 | — | — |
| 451 | S | S | N | 0 | 0 | 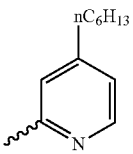 | 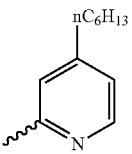 | — | — |
| 452 | S | S | N | 0 | 0 | 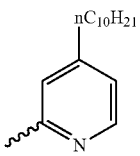 | 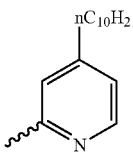 | — | — |
| 453 | S | S | N | 0 | 0 | 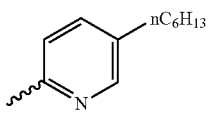 | 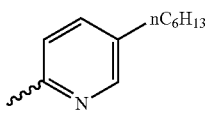 | — | — |
| 454 | S | S | N | 0 | 0 | 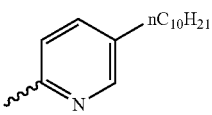 | 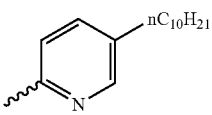 | — | — |
| 455 | S | S | N | 0 | 0 | 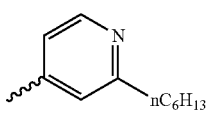 | 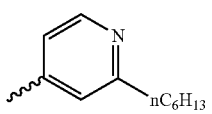 | — | — |
| 456 | S | S | N | 0 | 0 | 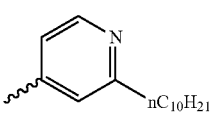 | 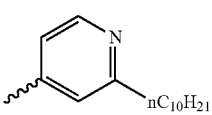 | — | — |
| 457 | S | S | N | 0 | 0 | 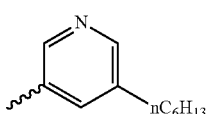 | 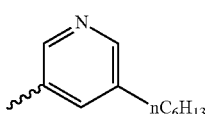 | — | — |
| 458 | S | S | N | 0 | 0 | 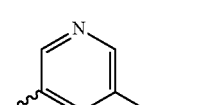 | 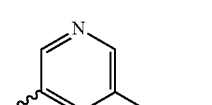 | — | — |
| 459 | S | O | S | 0 | 0 | CH$_3$ | CH$_3$ | — | — |
| 460 | S | O | S | 0 | 0 | n-C$_4$H$_9$ | n-C$_4$H$_9$ | — | — |
TABLE 24
| | | | | | | | | | |
|---|---|---|---|---|---|---|---|---|---|
| 461 | S | O | S | 0 | 0 | n-C$_5$H$_{11}$ | n-C$_5$H$_{11}$ | — | — |
| 462 | S | O | S | 0 | 0 | n-C$_6$H$_{13}$ | n-C$_6$H$_{13}$ | — | — |
| 463 | S | O | S | 0 | 0 | n-C$_7$H$_{15}$ | n-C$_7$H$_{15}$ | — | — |
| 464 | S | O | S | 0 | 0 | n-C$_8$H$_{17}$ | n-C$_8$H$_{17}$ | — | — |
| 465 | S | O | S | 0 | 0 | n-C$_9$H$_{19}$ | n-C$_9$H$_{19}$ | — | — |
| 466 | S | O | S | 0 | 0 | n-C$_{10}$H$_{21}$ | n-C$_{10}$H$_{21}$ | — | — |
| 467 | S | O | S | 0 | 0 | n-C$_{11}$H$_{23}$ | n-C$_{11}$H$_{23}$ | — | — |
| 468 | S | O | S | 0 | 0 | n-C$_{12}$H$_{25}$ | n-C$_{12}$H$_{25}$ | — | — |
| 469 | S | O | S | 0 | 0 |  |  | — | — |
| 470 | S | O | S | 0 | 0 |  | 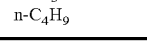 | — | — |

TABLE 24-continued
| | | | | | | | | | |
|---|---|---|---|---|---|---|---|---|---|
| 471 | S | O | S | 0 | 0 | 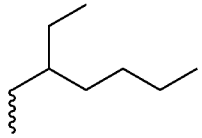 | 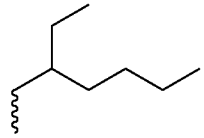 | — | — |
| 472 | S | O | S | 0 | 0 | 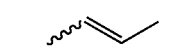 | 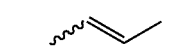 | — | — |
| 473 | S | O | S | 0 | 0 | 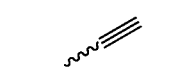 |  | — | — |
| 474 | S | O | S | 0 | 0 |  |  | — | — |
| 475 | S | O | S | 0 | 0 | 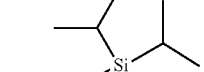 | 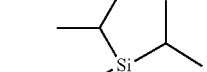 | — | — |
| 476 | S | O | S | 0 | 0 |  |  | — | — |
| 477 | S | O | S | 0 | 0 | 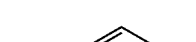 |  | — | — |
| 478 | S | O | S | 0 | 0 | 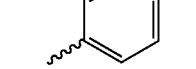 | 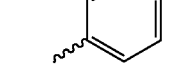 | — | — |
| 479 | S | O | S | 0 | 0 | 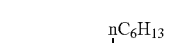 | 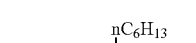 | — | — |
| 480 | S | O | S | 0 | 0 | 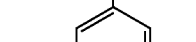 | 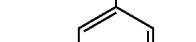 | — | — |
TABLE 25
| | | | | | | | | | |
|---|---|---|---|---|---|---|---|---|---|
| 481 | S | O | S | 0 | 0 | 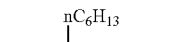 | 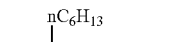 | — | — |

TABLE 25-continued
| 482 | S | O | S | 0 | 0 | 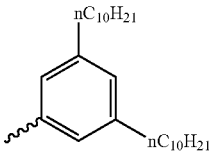 | 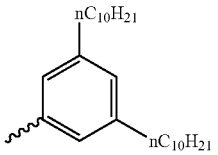 | — | — |
| 483 | S | O | S | 0 | 0 | 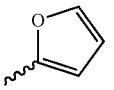 | 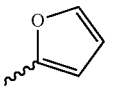 | — | — |
| 484 | S | O | S | 0 | 0 | 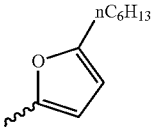 | 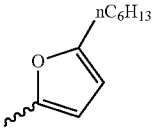 | — | — |
| 485 | S | O | S | 0 | 0 | 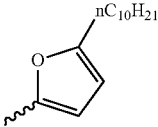 | 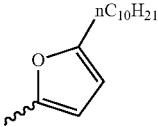 | — | — |
| 486 | S | O | S | 0 | 0 | 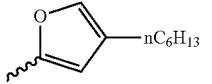 | 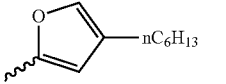 | — | — |
| 487 | S | O | S | 0 | 0 | 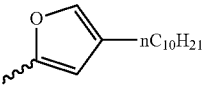 | 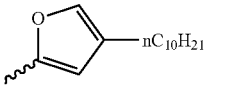 | — | — |
| 488 | S | O | S | 0 | 0 | 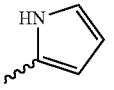 | 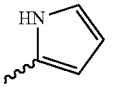 | — | — |
| 489 | S | O | S | 0 | 0 | 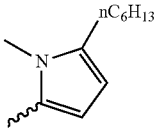 | 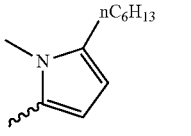 | — | — |
| 490 | S | O | S | 0 | 0 | 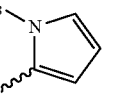 | 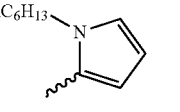 | — | — |
| 491 | S | O | S | 0 | 0 | 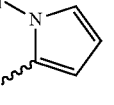 | 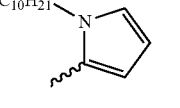 | — | — |
| 492 | S | O | S | 0 | 0 | 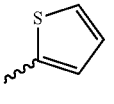 | 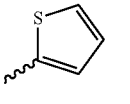 | — | — |
| 493 | S | O | S | 0 | 0 | 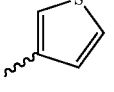 | 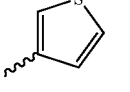 | — | — |
| 494 | S | O | S | 0 | 0 | 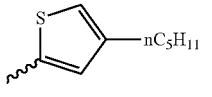 | 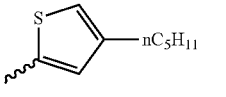 | — | — |

TABLE 25-continued
| | | | | | | | | | |
|---|---|---|---|---|---|---|---|---|---|
| 495 | S | O | S | 0 | 0 | 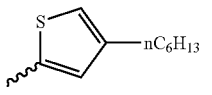 | 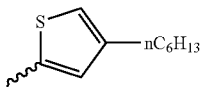 | — | — |
| 496 | S | O | S | 0 | 0 | 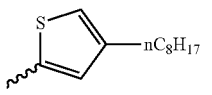 | 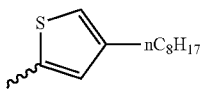 | — | — |
| 497 | S | O | S | 0 | 0 | 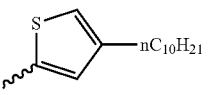 | 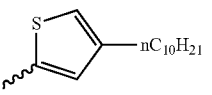 | — | — |
| 498 | S | O | S | 0 | 0 | 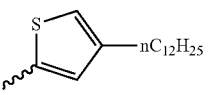 | 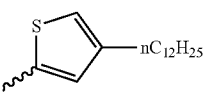 | — | — |
| 499 | S | O | S | 0 | 0 | 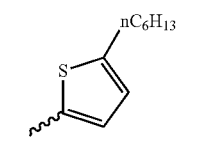 | 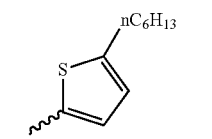 | — | — |
| 500 | S | O | S | 0 | 0 | 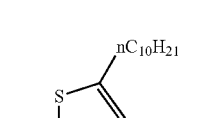 | 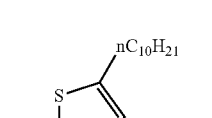 | — | — |
TABLE 26
| | | | | | | | | | |
|---|---|---|---|---|---|---|---|---|---|
| 501 | S | O | S | 0 | 0 | 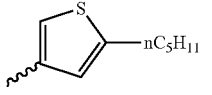 | 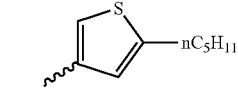 | — | — |
| 502 | S | O | S | 0 | 0 | 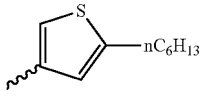 | 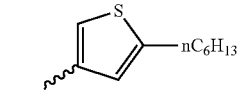 | — | — |
| 503 | S | O | S | 0 | 0 | 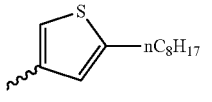 | 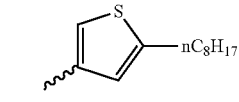 | — | — |
| 504 | S | O | S | 0 | 0 | 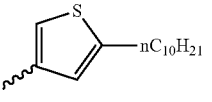 | 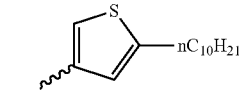 | — | — |
| 505 | S | O | S | 0 | 0 | 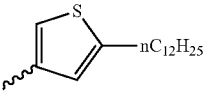 | 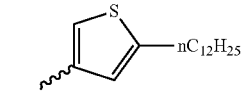 | — | — |
| 506 | S | O | S | 0 | 0 | 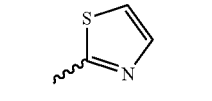 | 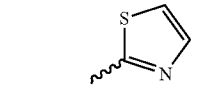 | — | — |
| 507 | S | O | S | 0 | 0 | 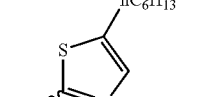 | 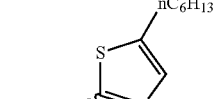 | — | — |

TABLE 26-continued

| | | | | | | | | |
|---|---|---|---|---|---|---|---|---|
| 508 | S | O | S | 0 | 0 | thiazole-nC10H21 | thiazole-nC10H21 | — — |
| 509 | S | O | S | 0 | 0 | thiazole-nC6H13 | thiazole-nC6H13 | — — |
| 510 | S | O | S | 0 | 0 | thiazole-nC10H21 | thiazole-nC10H21 | — — |
| 511 | S | O | S | 0 | 0 | thienothiophene | thienothiophene | — — |
| 512 | S | O | S | 0 | 0 | thienothiophene-nC6H13 | thienothiophene-nC6H13 | — — |
| 513 | S | O | S | 0 | 0 | thienothiophene-nC10H21 | thienothiophene-nC10H21 | — — |
| 514 | S | O | S | 0 | 0 | benzothiophene | benzothiophene | — — |
| 515 | S | O | S | 0 | 0 | benzothiophene-nC6H13 | benzothiophene-nC6H13 | — — |
| 516 | S | O | S | 0 | 0 | benzothiophene-nC10H21 | benzothiophene-nC10H21 | — — |
| 517 | S | O | S | 0 | 0 | benzothiophene-nC6H13 | benzothiophene-nC6H13 | — — |
| 518 | S | O | S | 0 | 0 | benzothiophene-nC10H21 | benzothiophene-nC10H21 | — — |

TABLE 26-continued
| 519 | S | O | S | 0 | 0 | 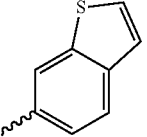 | 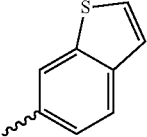 | — | — |
| 520 | S | O | S | 0 | 0 | 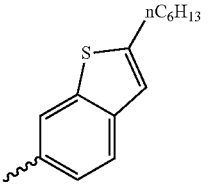 | 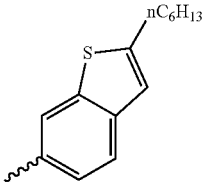 | — | — |
TABLE 27
| 521 | S | O | S | 0 | 0 | 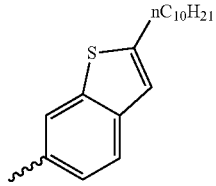 | 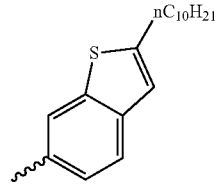 | — | — |
| 522 | S | O | S | 0 | 0 | 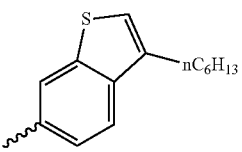 | 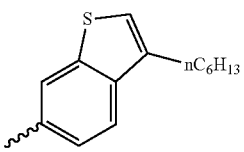 | — | — |
| 523 | S | O | S | 0 | 0 | 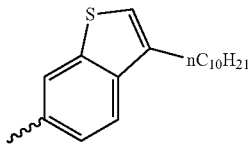 | 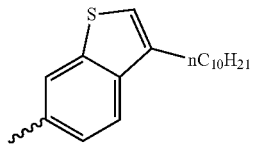 | — | — |
| 524 | S | O | S | 0 | 0 | 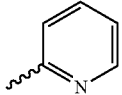 | 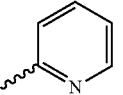 | — | — |
| 525 | S | O | S | 0 | 0 | 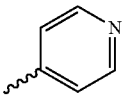 | 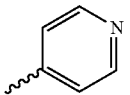 | — | — |
| 526 | S | O | S | 0 | 0 | 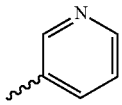 | 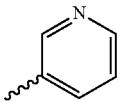 | — | — |
| 527 | S | O | S | 0 | 0 | 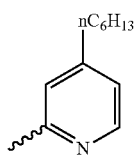 | 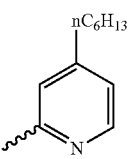 | — | — |
| 528 | S | O | S | 0 | 0 | 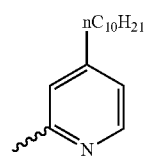 | 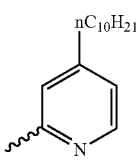 | — | — |

TABLE 27-continued
| 529 | S | O | S | 0 | 0 | 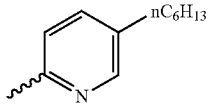 | 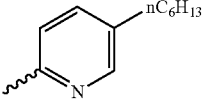 | — | — |
| 530 | S | O | S | 0 | 0 | 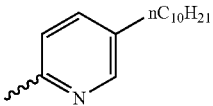 | 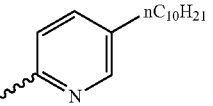 | — | — |
| 531 | S | O | S | 0 | 0 | 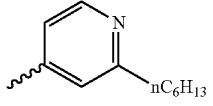 | 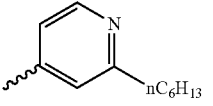 | — | — |
| 532 | S | O | S | 0 | 0 | 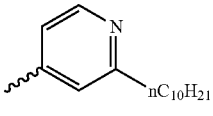 | 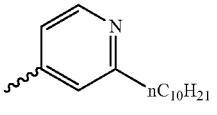 | — | — |
| 533 | S | O | S | 0 | 0 | 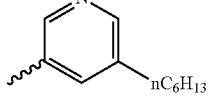 | 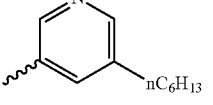 | — | — |
| 534 | S | O | S | 0 | 0 | 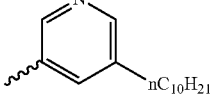 | 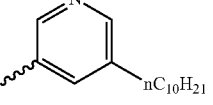 | — | — |
| 535 | Se | CH | S | 0 | 0 | $CH_3$ | $CH_3$ | — | — |
| 536 | Se | CH | S | 0 | 0 | n-$C_4H_9$ | n-$C_4H_9$ | — | — |
| 537 | Se | CH | S | 0 | 0 | n-$C_5H_{11}$ | n-$C_5H_{11}$ | — | — |
| 538 | Se | CH | S | 0 | 0 | n-$C_6H_{13}$ | n-$C_6H_{13}$ | — | — |
| 539 | Se | CH | S | 0 | 0 | n-$C_7H_{15}$ | n-$C_7H_{15}$ | — | — |
| 540 | Se | CH | S | 0 | 0 | n-$C_8H_{17}$ | n-$C_8H_{17}$ | — | — |
TABLE 28
| 541 | Se | CH | S | 0 | 0 | n-$C_9H_{19}$ | n-$C_9H_{19}$ | — | — |
| 542 | Se | CH | S | 0 | 0 | n-$C_{10}H_{21}$ | n-$C_{10}H_{21}$ | — | — |
| 543 | Se | CH | S | 0 | 0 | n-$C_{11}H_{23}$ | n-$C_{11}H_{23}$ | — | — |
| 544 | Se | CH | S | 0 | 0 | n-$C_{12}H_{25}$ | n-$C_{12}H_{25}$ | — | — |
| 545 | Se | CH | S | 0 | 0 | 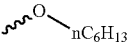 | 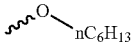 | — | — |
| 546 | Se | CH | S | 0 | 0 | 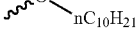 | 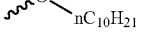 | — | — |
| 547 | Se | CH | S | 0 | 0 | 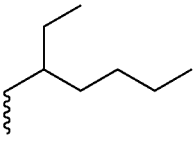 | 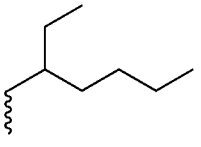 | — | — |
| 548 | Se | CH | S | 0 | 0 | 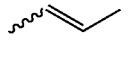 | 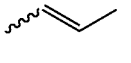 | — | — |
| 549 | Se | CH | S | 0 | 0 |  |  | — | — |

TABLE 28-continued
| 550 | Se | CH | S | 0 | 0 | 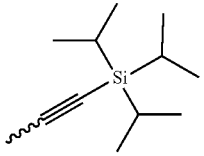 | 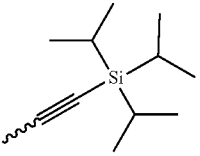 | — | — |
| 551 | Se | CH | S | 0 | 0 | 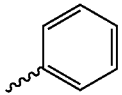 | 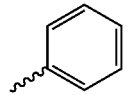 | — | — |
| 552 | Se | CH | S | 0 | 0 | 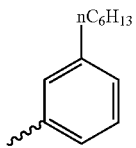 | 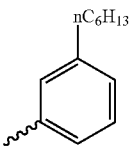 | — | — |
| 553 | Se | CH | S | 0 | 0 | 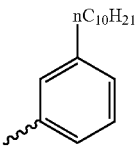 | 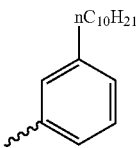 | — | — |
| 554 | Se | CH | S | 0 | 0 | 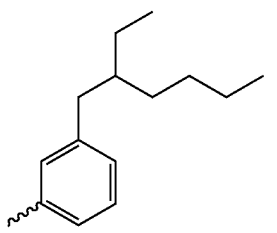 | 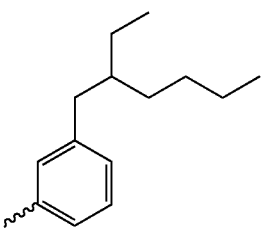 | — | — |
| 555 | Se | CH | S | 0 | 0 | 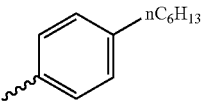 | 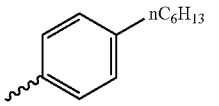 | — | — |
| 556 | Se | CH | S | 0 | 0 | 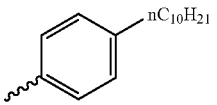 | 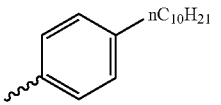 | — | — |
| 557 | Se | CH | S | 0 | 0 | 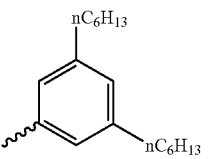 | 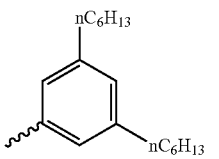 | — | — |
| 558 | Se | CH | S | 0 | 0 | 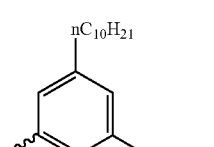 | 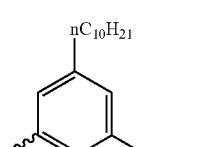 | — | — |
| 559 | Se | CH | S | 0 | 0 | 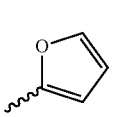 | 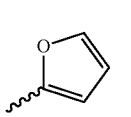 | — | — |

TABLE 28-continued
| 560 | Se | CH | S | 0 | 0 | 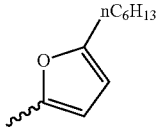 | 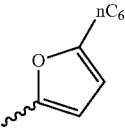 | — | — |
TABLE 29
| 561 | Se | CH | S | 0 | 0 | 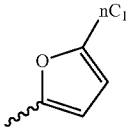 | 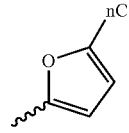 | — | — |
| 562 | Se | CH | S | 0 | 0 | 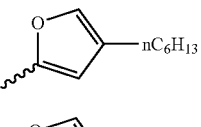 | 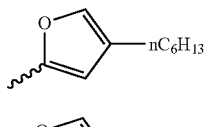 | — | — |
| 563 | Se | CH | S | 0 | 0 | 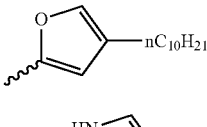 | 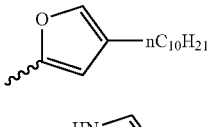 | — | — |
| 564 | Se | CH | S | 0 | 0 | 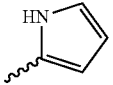 | 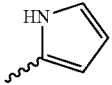 | — | — |
| 565 | Se | CH | S | 0 | 0 | 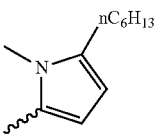 | 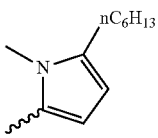 | — | — |
| 566 | Se | CH | S | 0 | 0 | 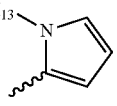 | 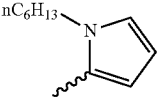 | — | — |
| 567 | Se | CH | S | 0 | 0 | 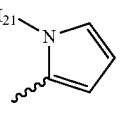 | 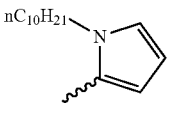 | — | — |
| 568 | Se | CH | S | 0 | 0 | 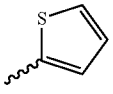 | 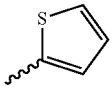 | — | — |
| 569 | Se | CH | S | 0 | 0 | 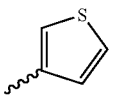 | 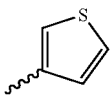 | — | — |
| 570 | Se | CH | S | 0 | 0 | 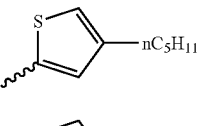 | 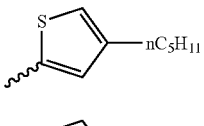 | — | — |
| 571 | Se | CH | S | 0 | 0 | 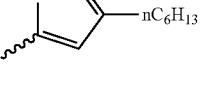 | 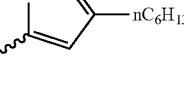 | — | — |
| 572 | Se | CH | S | 0 | 0 | 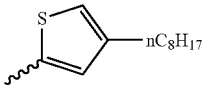 | 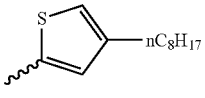 | — | — |

TABLE 29-continued
| | | | | | | | | |
|---|---|---|---|---|---|---|---|---|
| 573 | Se | CH | S | 0 | 0 | 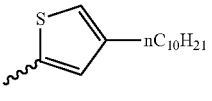 | 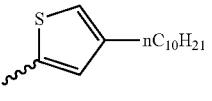 | — — |
| 574 | Se | CH | S | 0 | 0 | 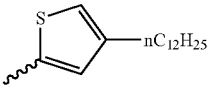 | 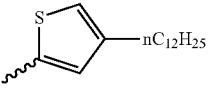 | — — |
| 575 | Se | CH | S | 0 | 0 | 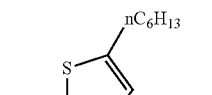 | 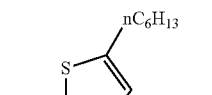 | — — |
| 576 | Se | CH | S | 0 | 0 | 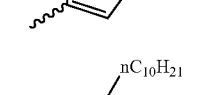 | 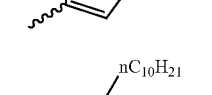 | — — |
| 577 | Se | CH | S | 0 | 0 | 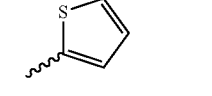 | 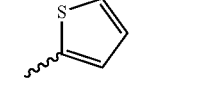 | — — |
| 578 | Se | CH | S | 0 | 0 | 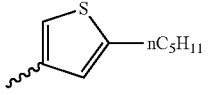 | 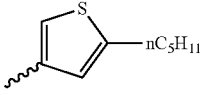 | — — |
| 579 | Se | CH | S | 0 | 0 | 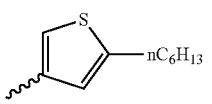 | 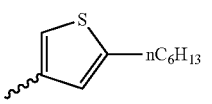 | — — |
| 580 | Se | CH | S | 0 | 0 | 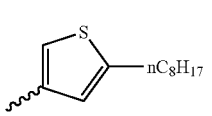 | 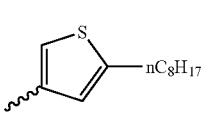 | — — |
TABLE 30
| | | | | | | | | |
|---|---|---|---|---|---|---|---|---|
| 581 | Se | CH | S | 0 | 0 | 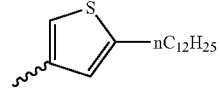 | 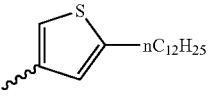 | — — |
| 582 | Se | CH | S | 0 | 0 | 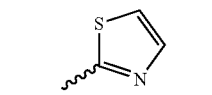 | 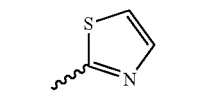 | — — |
| 583 | Se | CH | S | 0 | 0 | 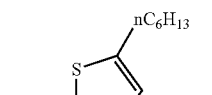 | 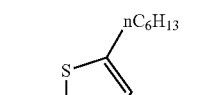 | — — |
| 584 | Se | CH | S | 0 | 0 | 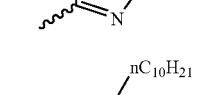 | 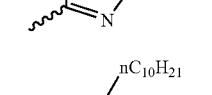 | — — |
| 585 | Se | CH | S | 0 | 0 | 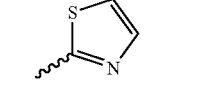 | 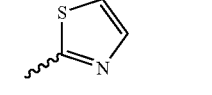 | — — |

TABLE 30-continued

| | | | | | | | | | |
|---|---|---|---|---|---|---|---|---|---|
| 586 | Se | CH | S | 0 | 0 | thiazole-nC₁₀H₂₁ | thiazole-nC₁₀H₂₁ | — | — |
| 587 | Se | CH | S | 0 | 0 | thienothiophene | thienothiophene | — | — |
| 588 | Se | CH | S | 0 | 0 | thienothiophene-nC₆H₁₃ | thienothiophene-nC₆H₁₃ | — | — |
| 589 | Se | CH | S | 0 | 0 | thienothiophene-nC₁₀H₂₁ | thienothiophene-nC₁₀H₂₁ | — | — |
| 590 | Se | CH | S | 0 | 0 | benzothiophene | benzothiophene | — | — |
| 591 | Se | CH | S | 0 | 0 | benzothiophene-nC₆H₁₃ | benzothiophene-nC₆H₁₃ | — | — |
| 592 | Se | CH | S | 0 | 0 | benzothiophene-nC₁₀H₂₁ | benzothiophene-nC₁₀H₂₁ | — | — |
| 593 | Se | CH | S | 0 | 0 | benzothiophene-nC₆H₁₃ | benzothiophene-nC₆H₁₃ | — | — |
| 594 | Se | CH | S | 0 | 0 | benzothiophene-nC₁₀H₂₁ | benzothiophene-nC₁₀H₂₁ | — | — |
| 595 | Se | CH | S | 0 | 0 | benzothiophene | benzothiophene | — | — |
| 596 | Se | CH | S | 0 | 0 | benzothiophene-nC₆H₁₃ | benzothiophene-nC₆H₁₃ | — | — |

TABLE 30-continued

| 597 | Se | CH | S | 0 | 0 | benzothiophene-nC₁₀H₂₁ | benzothiophene-nC₁₀H₂₁ | — | — |
| 598 | Se | CH | S | 0 | 0 | benzothiophene-nC₆H₁₃ | benzothiophene-nC₆H₁₃ | — | — |
| 599 | Se | CH | S | 0 | 0 | benzothiophene-nC₁₀H₂₁ | benzothiophene-nC₁₀H₂₁ | — | — |
| 600 | Se | CH | S | 0 | 0 | pyridine | pyridine | — | — |

TABLE 31

| 601 | Se | CH | S | 0 | 0 | pyridine (4-) | pyridine (4-) | — | — |
| 602 | Se | CH | S | 0 | 0 | pyridine (3-) | pyridine (3-) | — | — |
| 603 | Se | CH | S | 0 | 0 | pyridine-nC₆H₁₃ | pyridine-nC₆H₁₃ | — | — |
| 604 | Se | CH | S | 0 | 0 | pyridine-nC₁₀H₂₁ | pyridine-nC₁₀H₂₁ | — | — |
| 605 | Se | CH | S | 0 | 0 | pyridine-nC₆H₁₃ | pyridine-nC₆H₁₃ | — | — |
| 606 | Se | CH | S | 0 | 0 | pyridine-nC₁₀H₂₁ | pyridine-nC₁₀H₂₁ | — | — |
| 607 | Se | CH | S | 0 | 0 | pyridine-nC₆H₁₃ | pyridine-nC₆H₁₃ | — | — |

TABLE 31-continued

| | | | | | | | | | |
|---|---|---|---|---|---|---|---|---|---|
| 608 | Se | CH | S | 0 | 0 | 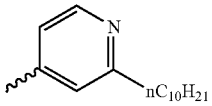 | 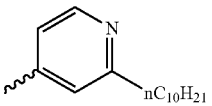 | — | — |
| 609 | Se | CH | S | 0 | 0 | 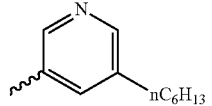 | 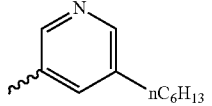 | — | — |
| 610 | Se | CH | S | 0 | 0 | 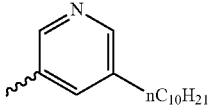 | 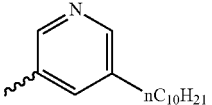 | — | — |
| 611 | S | CH | N(n-C10H21) | 0 | 0 | $CH_3$ | $CH_3$ | — | — |
| 612 | S | CH | N(n-C10H21) | 0 | 0 | $n\text{-}C_4H_9$ | $n\text{-}C_4H_9$ | — | — |
| 613 | S | CH | N(n-C10H21) | 0 | 0 | $n\text{-}C_5H_{11}$ | $n\text{-}C_5H_{11}$ | — | — |
| 614 | S | CH | N(n-C10H21) | 0 | 0 | $n\text{-}C_6H_{13}$ | $n\text{-}C_6H_{13}$ | — | — |
| 615 | S | CH | N(n-C10H21) | 0 | 0 | $n\text{-}C_7H_{15}$ | $n\text{-}C_7H_{15}$ | — | — |
| 616 | S | CH | N(n-C10H21) | 0 | 0 | $n\text{-}C_8H_{17}$ | $n\text{-}C_8H_{17}$ | — | — |
| 617 | S | CH | N(n-C10H21) | 0 | 0 | $n\text{-}C_9H_{19}$ | $n\text{-}C_9H_{19}$ | — | — |
| 618 | S | CH | N(n-C10H21) | 0 | 0 | $n\text{-}C_{10}H_{21}$ | $n\text{-}C_{10}H_{21}$ | — | — |
| 619 | S | CH | N(n-C10H21) | 0 | 0 | $n\text{-}C_{11}H_{23}$ | $n\text{-}C_{11}H_{23}$ | — | — |
| 620 | S | CH | N(n-C10H21) | 0 | 0 | $n\text{-}C_{12}H_{25}$ | $n\text{-}C_{12}H_{25}$ | — | — |

TABLE 32

| | | | | | | | | | |
|---|---|---|---|---|---|---|---|---|---|
| 601 | Se | CH | S | 0 | 0 | 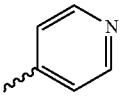 | 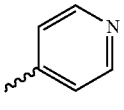 | — | — |
| 602 | Se | CH | S | 0 | 0 | 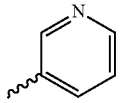 | 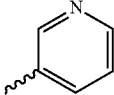 | — | — |
| 603 | Se | CH | S | 0 | 0 | 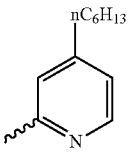 | 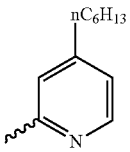 | — | — |
| 604 | Se | CH | S | 0 | 0 | 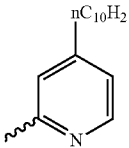 | 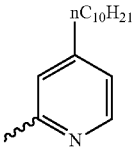 | — | — |
| 605 | Se | CH | S | 0 | 0 | 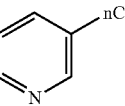 | 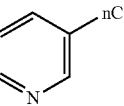 | — | — |
| 606 | Se | CH | S | 0 | 0 | 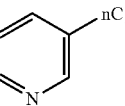 | 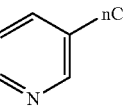 | — | — |
| 607 | Se | CH | S | 0 | 0 | 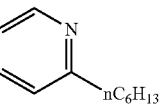 | 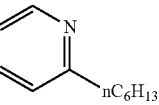 | — | — |

TABLE 32-continued

| | | | | | | | | | |
|---|---|---|---|---|---|---|---|---|---|
| 608 | Se | CH | S | 0 | 0 | 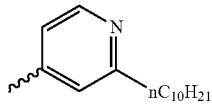 nC$_{10}$H$_{21}$ | 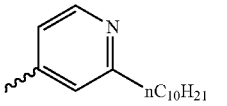 nC$_{10}$H$_{21}$ | — | — |
| 609 | Se | CH | S | 0 | 0 | 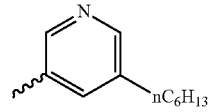 nC$_6$H$_{13}$ | 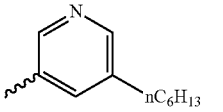 nC$_6$H$_{13}$ | — | — |
| 610 | Se | CH | S | 0 | 0 | 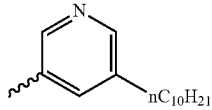 nC$_{10}$H$_{21}$ | 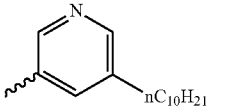 nC$_{10}$H$_{21}$ | — | — |
| 611 | S | CH | N(n-C10H21) | 0 | 0 | CH$_3$ | CH$_3$ | — | — |
| 612 | S | CH | N(n-C10H21) | 0 | 0 | n-C$_4$H$_9$ | n-C$_4$H$_9$ | — | — |
| 613 | S | CH | N(n-C10H21) | 0 | 0 | n-C$_5$H$_{11}$ | n-C$_5$H$_{11}$ | — | — |
| 614 | S | CH | N(n-C10H21) | 0 | 0 | n-C$_6$H$_{13}$ | n-C$_6$H$_{13}$ | — | — |
| 615 | S | CH | N(n-C10H21) | 0 | 0 | n-C$_7$H$_{15}$ | n-C$_7$H$_{15}$ | — | — |
| 616 | S | CH | N(n-C10H21) | 0 | 0 | n-C$_8$H$_{17}$ | n-C8H17 | — | — |
| 617 | S | CH | N(n-C10H21) | 0 | 0 | n-C$_9$H$_{19}$ | n-C$_9$H$_{19}$ | — | — |
| 618 | S | CH | N(n-C10H21) | 0 | 0 | n-C$_{10}$H$_{21}$ | n-C$_{10}$H$_{21}$ | — | — |
| 619 | S | CH | N(n-C10H21) | 0 | 0 | n-C$_{11}$H$_{23}$ | n-C$_{11}$H$_{23}$ | — | — |
| 620 | S | CH | N(n-C10H21) | 0 | 0 | n-C$_{12}$H$_{25}$ | n-C$_{12}$H$_{25}$ | — | — |

TABLE 33

| | | | | | | | | | |
|---|---|---|---|---|---|---|---|---|---|
| 641 | S | CH | N(n-C10H21) | 0 | 0 | 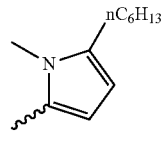 | 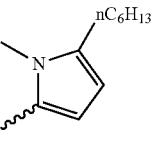 | — | — |
| 642 | S | CH | N(n-C10H21) | 0 | 0 | 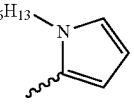 | 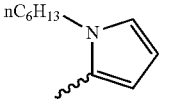 | — | — |
| 643 | S | CH | N(n-C10H21) | 0 | 0 | 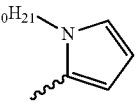 | 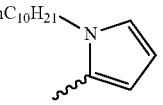 | — | — |
| 644 | S | CH | N(n-C10H21) | 0 | 0 |  |  | — | — |
| 645 | S | CH | N(n-C10H21) | 0 | 0 |  |  | — | — |
| 646 | S | CH | N(n-C10H21) | 0 | 0 | 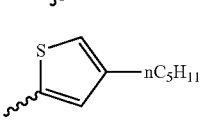 | 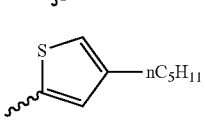 | — | — |
| 647 | S | CH | N(n-C10H21) | 0 | 0 | 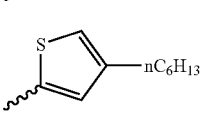 | 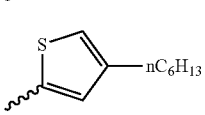 | — | — |
| 648 | S | CH | N(n-C10H21) | 0 | 0 | 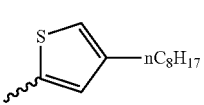 | 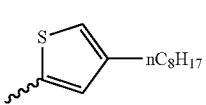 | — | — |

TABLE 33-continued
| | | | | | | | | | |
|---|---|---|---|---|---|---|---|---|---|
| 649 | S | CH | N(n-C10H21) | 0 | 0 | 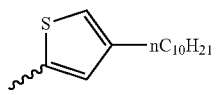 | 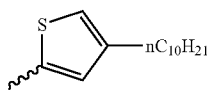 | — | — |
| 650 | S | CH | N(n-C10H21) | 0 | 0 | 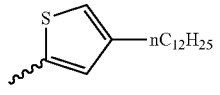 | 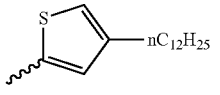 | — | — |
| 651 | S | CH | N(n-C10H21) | 0 | 0 | 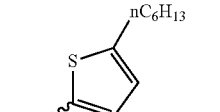 | 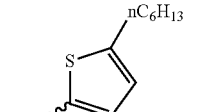 | — | — |
| 652 | S | CH | N(n-C10H21) | 0 | 0 | 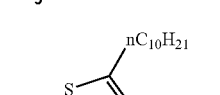 | 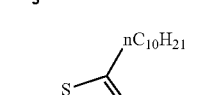 | — | — |
| 653 | S | CH | N(n-C10H21) | 0 | 0 | 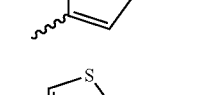 | 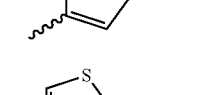 | — | — |
| 654 | S | CH | N(n-C10H21) | 0 | 0 | 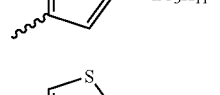 | 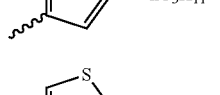 | — | — |
| 655 | S | CH | N(n-C10H21) | 0 | 0 | 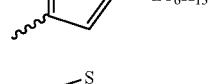 | 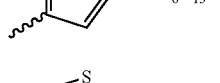 | — | — |
| 656 | S | CH | N(n-C10H21) | 0 | 0 | 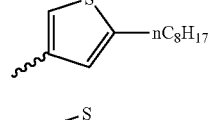 | 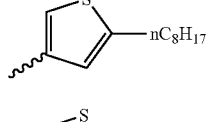 | — | — |
| 657 | S | CH | N(n-C10H21) | 0 | 0 | 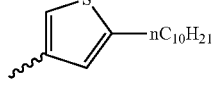 | 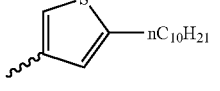 | — | — |
| 658 | S | CH | N(n-C10H21) | 0 | 0 | 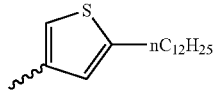 | 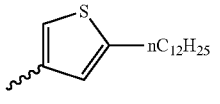 | — | — |
| 659 | S | CH | N(n-C10H21) | 0 | 0 | 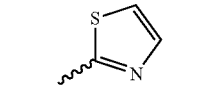 | 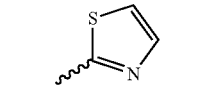 | — | — |
| 660 | S | CH | N(n-C10H21) | 0 | 0 | 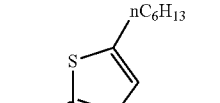 | 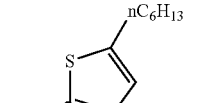 | — | — |
TABLE 34
| | | | | | | | | | |
|---|---|---|---|---|---|---|---|---|---|
| 661 | S | CH | N(n-C10H21) | 0 | 0 | 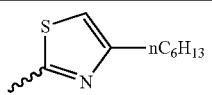 | 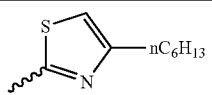 | — | — |

TABLE 34-continued
| 662 | S | CH | N(n-C10H21) | 0 | 0 | 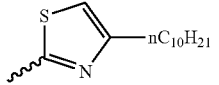 | 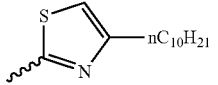 | — | — |
| 663 | S | CH | N(n-C10H21) | 0 | 0 | 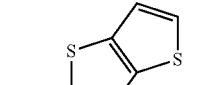 | 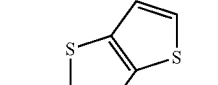 | — | — |
| 664 | S | CH | N(n-C10H21) | 0 | 0 | 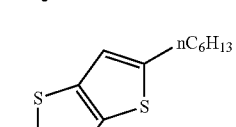 | 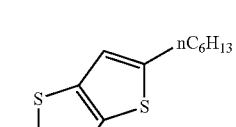 | — | — |
| 665 | S | CH | N(n-C10H21) | 0 | 0 | 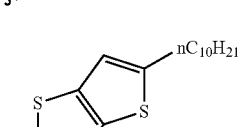 | 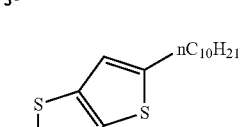 | — | — |
| 666 | S | CH | N(n-C10H21) | 0 | 0 | 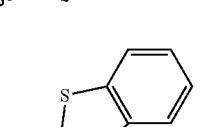 | 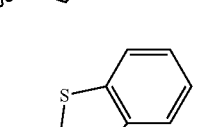 | — | — |
| 667 | S | CH | N(n-C10H21) | 0 | 0 | 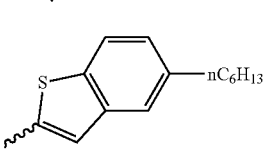 | 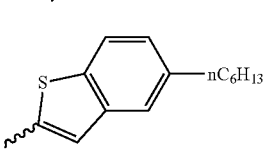 | — | — |
| 668 | S | CH | N(n-C10H21) | 0 | 0 | 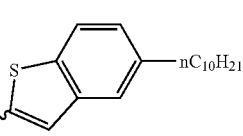 | 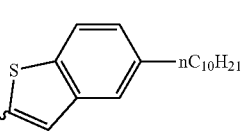 | — | — |
| 669 | S | CH | N(n-C10H21) | 0 | 0 | 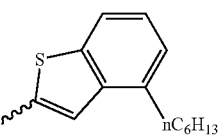 | 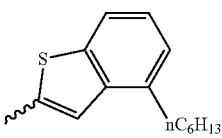 | — | — |
| 670 | S | CH | N(n-C10H21) | 0 | 0 | 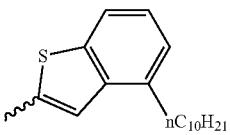 | 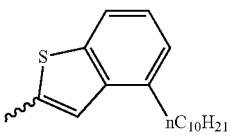 | — | — |
| 671 | S | CH | N(n-C10H21) | 0 | 0 | 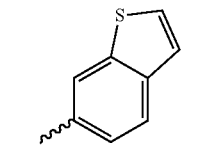 | 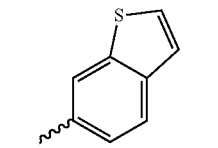 | — | — |
| 672 | S | CH | N(n-C10H21) | 0 | 0 | 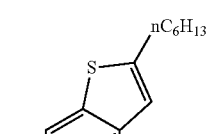 | 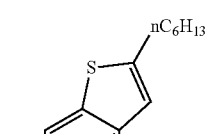 | — | — |

TABLE 34-continued
| | | | | | | | | | |
|---|---|---|---|---|---|---|---|---|---|
| 673 | S | CH | N(n-C10H21) | 0 | 0 |  |  | — | — |
| 674 | S | CH | N(n-C10H21) | 0 | 0 | 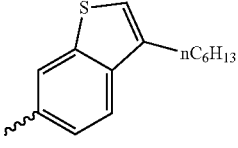 | 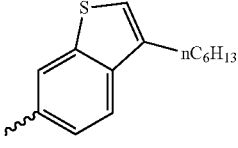 | — | — |
| 675 | S | CH | N(n-C10H21) | 0 | 0 | 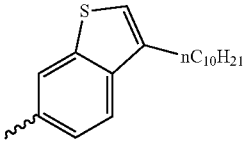 | 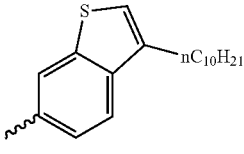 | — | — |
| 676 | S | CH | N(n-C10H21) | 0 | 0 | 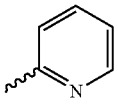 | 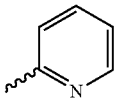 | — | — |
| 677 | S | CH | N(n-C10H21) | 0 | 0 | 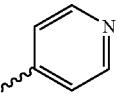 | 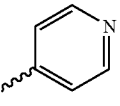 | — | — |
| 678 | S | CH | N(n-C10H21) | 0 | 0 | 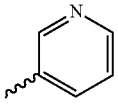 | 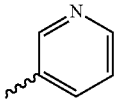 | — | — |
| 679 | S | CH | N(n-C10H21) | 0 | 0 | 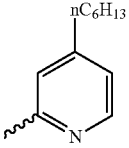 | 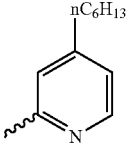 | — | — |
| 680 | S | CH | N(n-C10H21) | 0 | 0 | 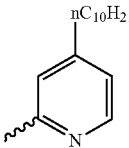 | 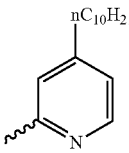 | — | — |
TABLE 35
| | | | | | | | | | |
|---|---|---|---|---|---|---|---|---|---|
| 681 | S | CH | N(n-C10H21) | 0 | 0 | 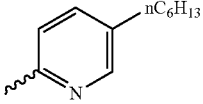 | 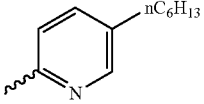 | — | — |
| 682 | S | CH | N(n-C10H21) | 0 | 0 | 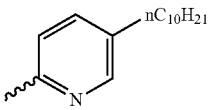 | 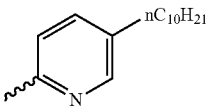 | — | — |
| 683 | S | CH | N(n-C10H21) | 0 | 0 | 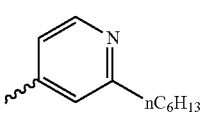 | 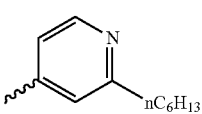 | — | — |

TABLE 35-continued

| 684 | S | CH | N(n-C10H21) | 0 | 0 | ![pyridine-nC10H21] | ![pyridine-nC10H21] | — | — |
| 685 | S | CH | N(n-C10H21) | 0 | 0 | ![pyridine-nC6H13] | ![pyridine-nC6H13] | — | — |
| 686 | S | CH | N(n-C10H21) | 0 | 0 | ![pyridine-nC10H21] | ![pyridine-nC10H21] | — | — |

The molecular weight of the compound, which is represented by Formula (1) and has a molecular weight of equal to or less than 3,000, is preferably equal to or less than 2,000, more preferably equal to or less than 1,000, and particularly preferably equal to or less than 850. It is preferable that the molecular weight is equal to or less than the above upper limit, because then the solubility of the compound in a solvent can be improved.

From the viewpoint of film quality stability of the film, the molecular weight is preferably equal to or greater than 250, more preferably equal to or greater than 300, and even more preferably equal to or greater than 350.

In the present invention, the compound which is represented by Formula (1) and has a molecular weight of equal to or less than 3,000 may be a compound (so-called oligomer) having a repeating unit. In the present invention, whether a compound has a molecular weight of equal to or less than 3,000 can be checked by the following molecular weight measurement method.

The molecular weight can be obtained through mass spectrometry using an ionization method such as matrix assisted laser desorption/ionization (MALDI), atmospheric pressure chemical ionization (APCI), or electrospray ionization (ESI) or obtained by determining a weight-average molecular weight (Mw), expressed in terms of polystyrene, of a compound dissolved in tetrahydrofuran by using gel permeation chromatography (GPC).

The compound which is represented by Formula (1) and has a molecular weight of equal to or less than 3,000 can be synthesized with reference to a method for synthesizing an organic semiconductor material of the present invention that will be described later.

Generally, for synthesizing the compound which is represented by Formula (1) and has a molecular weight of equal to or less than 3,000, any of reaction conditions may be used. As a reaction solvent, any of solvents may be used. Furthermore, in order to accelerate a ring-forming reaction, an acid or a base is preferably used, and an acid is particularly preferably used. Although optimal reaction conditions vary with the structure of the intended compound, they can be set with reference to the specific reaction conditions described in the aforementioned documents.

A synthetic intermediate having various substituents can be synthesized using known reactions in combination. Furthermore, various substituents may be introduced into the intermediate at any stage. After the intermediate is synthesized, it is preferable to purify the intermediate by column chromatography, recrystallization, or the like and then further purify it by sublimation. By the sublimation purification, it is possible to separate organic impurities and to effectively remove an inorganic salt, a residual solvent, and the like.

<Method for Synthesizing Organic Semiconductor Material of the Present Invention>

In a method for synthesizing an organic semiconductor material of the present invention, a compound represented by the following Formula (6) or (7) and a compound represented by the following Formula (8) are reacted by heating in the presence of a transition metal catalyst and an organic solvent, and as a result, the compound which is represented by Formula (1) and has a molecular weight of equal to or less than 3,000 is synthesized.

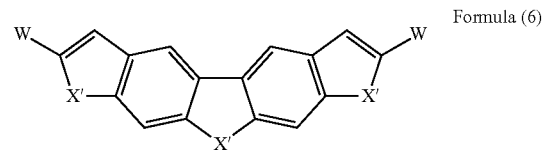

Formula (6)

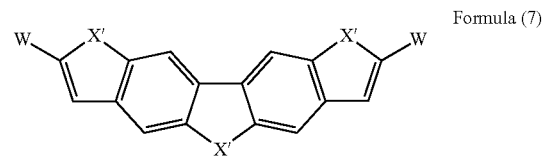

Formula (7)

In Formulae (6) and (7), each X' independently represents an oxygen atom, a sulfur atom, or a selenium atom; and each W independently represents a halogen atom or a perfluoroalkylsulfonyloxy group;

Formula (8)

$R^{11}$ represents an alkyl group, an alkenyl group, an alkynyl group, an aryl group, or a heteroaryl group and may further have a substituent;

M represents magnesium, silicon, boron, tin, or zinc;

each $R^{12}$ independently represents a halogen atom, an alkyl group, an alkenyl group, an alkynyl group, an alkoxy group, or a hydroxyl group, and $R^{12}$'s may be the same as or different from each other and may form a ring; and i represents an integer of 1 to 3 and equals a valency of M−1, here, in a case where M is boron, i may be 3.

First, Formulae (6) and (7) will be described.

In Formula (6), a preferred range of X' is the same as the preferred range of the combination of X and Z in Formula (1).

In Formula (7), a preferred range of X' is the same as the preferred range of the combination of X and Y in Formula (1).

In Formulae (6) and (7), each W independently represents a halogen atom or a perfluoroalkylsulfonyloxy group. W is preferably a halogen atom. In a case where W represents a halogen atom, the halogen atom is not particularly limited, and examples thereof include a fluorine atom, a chlorine atom, a bromine atom, an iodine atom, and the like. Among these, an iodine atom or a bromine atom is preferable, and a bromine atom is more preferable. In a case where W represents a perfluoroalkylsulfonyloxy group, the perfluoroalkylsulfonyloxy group is not particularly limited. The perfluoroalkylsulfonyloxy group is preferably a sulfonyloxy group substituted with a perfluoroalkyl group having 1 to 10 carbon atoms, and more preferably a trifluoromethylsulfonyloxy group.

Next, Formula (8) will be described.

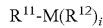

$$R^{11}\text{-}M(R^{12})_i \qquad \text{Formula (8)}$$

In Formula (8), $R^{11}$ represents an alkyl group, an alkenyl group, an alkynyl group, an aryl group, or a heteroaryl group and may further have a substituent. A preferred range of $R^{11}$ is the same as the preferred range of $R^1$ or $R^2$ in Formula (1).

In Formula (8), M represents magnesium, silicon, boron, tin, or zinc. M is preferably boron, zinc, or tin, and more preferably tin or zinc.

In Formula (8), each $R^{12}$ independently represents a halogen atom, an alkyl group, an alkenyl group, an alkynyl group, an alkoxy group, or a hydroxyl group. $R^{12}$'s may be the same as or different from each other and may form a ring with each other. $R^{12}$ is preferably a halogen atom, an alkyl group, or an alkoxy group.

In a case where M is boron, $R^{12}$ is preferably an alkoxy group, and more preferably an alkoxy group having 1 to 10 carbon atoms. Furthermore, $R^{12}$'s may form a ring having 4 to 10 carbon atoms by being bonded to each other.

In a case where M is tin, $R^{12}$ is preferably an alkyl group having 1 to 6 carbon atoms, and more preferably a methyl group.

In a case where M is zinc, $M^2$ is preferably a halogen atom.

In Formula (8), i represents an integer of 1 to 3 and equals a valency of M−1. Here, in a case where M is boron, i may be 3.

i is preferably 2 or 3.

In a case where M is boron and i is 3, —B($R^{12}$)$_3$ is accompanied by an arbitrary cation $(X^3)^+$ and represents a salt of —B⁻($R^{12}$)$_3$$(X^3)^+$.

Examples of the transition metal catalyst used in the method for synthesizing an organic semiconductor material of the present invention include a palladium catalyst such as tetrakis triphenylphosphine palladium (0), tris(dibenzylideneacetone)dipalladium (0), palladium (II) acetate, palladium (II) chloride, a [1,1'-bis(diphenylphosphino)ferrocene]dichloropalladium (II)/dichloroethane complex, [1,3-bis(diphenylphosphino)propane]palladium (II) dichloride, or bis(triphenylphosphine)palladium (II) dichloride, a copper catalyst such as copper (II) chloride, copper (I) chloride, copper (0), cuprous oxide, or copper (II) oxide, a nickel catalyst such as [1,3-bis(diphenylphosphino)propane] nickel (II) dichloride, or dibromobis(triphenylphosphine)nickel (II), bis(1,5-cyclooctadiene)nickel (0), and the like. Among these, a palladium catalyst is preferable. One kind of transition metal catalyst may be used singly, or two or more kinds thereof may be used in combination. Furthermore, these transition metal catalysts can be used in combination with an appropriate ligand.

As the ligand, for example, a phosphine ligand such as triphenylphosphine, tri-t-butylphosphine, tricyclohexylphosphine, 4,5-bis(diphenylphosphino)-9,9-dimethylxanthene, diphenylphosphinoferrocene, 2,2'-bis(diphenylphosphino)-1,1'-binaphthyl, diphenylphosphinopropane, 2-dicyclohexylphosphino-2',4',6'-triisopropylbiphenyl, or 2-dicyclohexylphosphino-2',6'-dimethoxybiphenyl is particularly preferable.

The organic solvent used in the method for synthesizing an organic semiconductor material of the present invention is not particularly limited. Examples thereof include organic solvents exemplified as organic solvents usable in a coating solution for a non-light-emitting organic semiconductor device which will be described later. Among these, N,N-dimethylformamide, toluene, tetrahydrofuran, dimethoxyethane, and the like are preferable.

As the heating conditions in the method for synthesizing an organic semiconductor material of the present invention, the heating temperature is preferably 20° C. to 120° C., and more preferably 40° C. to 100° C.

The heating time is preferably 1 hour to 48 hours, and more preferably 5 hours to 24 hours.

At the time of heating, it is preferable to perform stirring.

<Structure of Organic Transistor>

The organic transistor of the present invention has a semiconductor active layer containing the compound which is represented by the Formula (1) and has a molecular weight of equal to or less than 3,000.

The organic transistor of the present invention may further have layers other than the semiconductor active layer.

The organic transistor of the present invention is preferably used as an organic field effect transistor (FET), and is more preferably used as an insulated gate-type FET in which the gate is insulated from channels.

Hereinafter, preferred structural aspects of the organic transistor of the present invention will be specifically described by using drawings, but the present invention is not limited to the aspects.

(Lamination Structure)

The lamination structure of an organic field effect transistor is not particularly limited, and various known structures can be adopted.

For example, the organic transistor of the present invention can adopt a structure (bottom gate/top contact type) in which an electrode, an insulator layer, a semiconductor active layer (organic semiconductor layer), and two electrodes are arranged in this order on the upper surface of a substrate which is a lower most layer. In this structure, the electrode on the upper surface of the substrate as the lower most layer is provided in a portion of the substrate, and the insulator layer is so disposed that it comes into contact with the substrate in a portion other than the electrode. The two electrodes provided on the upper surface of the semiconductor active layer are arranged in a state of being separated from each other.

FIG. 1 shows the constitution of a bottom gate/top contact-type element. FIG. 1 is a schematic view showing a section of an exemplary structure of the organic transistor manufactured as a substrate for measuring FET characteristics in examples of the present invention. In the organic transistor shown in FIG. 1, a substrate 11 is disposed as a lower most layer, an electrode 12 is provided in a portion of the upper surface thereof, and an insulator layer 13 is provided such that it covers the electrode 12 and contacts the substrate 11 in a portion other than the electrode 12. On the upper surface of the insulator layer 13, a semiconductor active layer 14 is provided, and in a portion of the upper surface thereof, two electrodes 15a and 15b are arranged in a state of being separated from each other.

In the organic transistor shown in FIG. 1, the electrode 12 is a gate, and the electrode 15a and the electrode 15b are a drain and a source respectively. The organic transistor shown in FIG. 1 is an insulated gate-type FET in which a channel as a path of electric currents between the drain and the source is insulated from the gate.

As an example of the structure of the organic transistor of the present invention, a bottom gate/bottom contact-type element can be exemplified.

Figure 2:
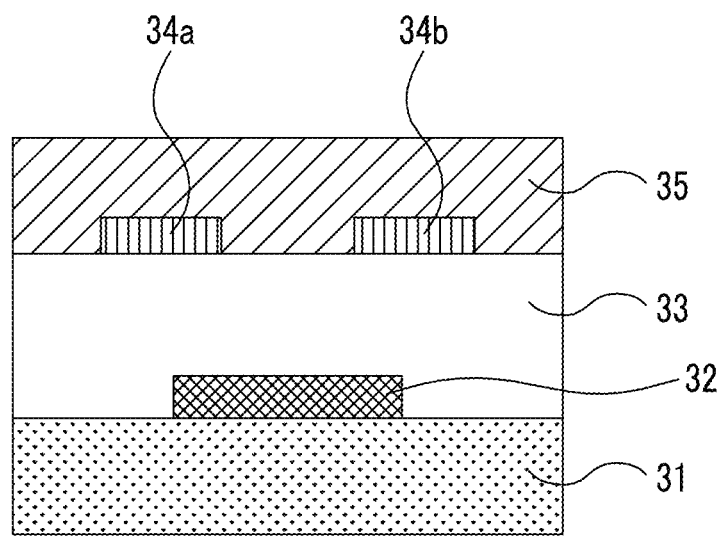
FIG. 2 is a schematic view showing a section of the structure of the organic transistor of the present invention.

FIG. 2 shows the constitution of the bottom gate/bottom contact-type element. FIG. 2 is a schematic view showing a section of the structure of an organic transistor manufactured as a substrate for measuring FET characteristics in examples of the present invention. In the organic transistor shown in FIG. 2, a substrate 31 is disposed as a lower most layer, an electrode 32 is provided in a portion of the upper surface thereof, and an insulator layer 33 is provided such that it covers the electrode 32 and comes into contact with the substrate 31 in a portion other than the electrode 32. Furthermore, a semiconductor active layer 35 is provided on the upper surface of the insulator layer 33, and electrodes 34a and 34b are in a lower portion of the semiconductor active layer 35.

In the organic transistor shown in FIG. 2, the electrode 32 is a gate, and the electrode 34a and the electrode 34b are a drain and a source respectively. The organic transistor shown in FIG. 2 is an insulated gate-type FET in which a channel as a path of electric currents between the drain and the source is insulated from the gate.

As the structure of the organic transistor of the present invention, a top gate/top contact-type element in which an insulator and a gate electrode are in the upper portion of a semiconductor active layer or a top gate/bottom contact-type element can also be preferably used.

(Thickness)

In a case where the organic transistor of the present invention needs to be a thinner transistor, the total thickness of the transistor is preferably, for example, 0.1 μm to 0.5 μm.

(Sealing)

In order to improve the preservation stability of the organic transistor element by blocking the organic transistor element from the atmosphere or moisture, the entirety of the organic transistor element may be sealed with a metal sealing can, glass, an inorganic material such as silicon nitride, a polymer material such as perylene, a low-molecular weight material, or the like.

Hereinafter, preferred aspects of the respective layers of the organic transistor of the present invention will be described, but the present invention is not limited to the aspects.

<Substrate>

(Material)

The organic transistor of the present invention preferably includes a substrate.

The material of the substrate is not particularly limited, and known materials can be used. Examples of the material include a polyester film such as polyethylene naphthalate (PEN) or polyethylene terephthalate (PET), a cycloolefin polymer film, a polycarbonate film, a triacetylcellulose (TAC) film, a polyimide film, a material obtained by bonding these polymer films to extremely thin glass, ceramics, silicon, quartz, glass, and the like. Among these, silicon is preferable.

<Electrode>

(Material)

The organic transistor of the present invention preferably includes an electrode.

As the material constituting the electrode, known conductive materials such as a metal material like Cr, Al, Ta, Mo, Nb, Cu, Ag, Au, Pt, Pd, In, Ni, or Nd, an alloy material of these, a carbon material, and a conductive polymer can be used without particular limitation.

(Thickness)

The thickness of the electrode is not particularly limited, but is preferably 10 nm to 50 nm.

A gate width (or a channel width) W and a gate length (or a channel length) L are not particularly limited. However, a ratio of W/L is preferably equal to or greater than 10, and more preferably equal to or greater than 20.

<Acceptor>

(Material)

The organic transistor of the present invention preferably includes an acceptor for accelerating injection of carriers. Preferred examples of the material include known 2,3,5,6-tetrafluoro-7,7,8,8-tetracyanoquinodimethane (F4-TCNQ) and the like.

(Thickness)

The thickness of the acceptor is not particularly limited and is preferably equal to or less than 5 nm.

<Insulating Layer>

(Material)

The material constituting the insulating layer is not particularly limited as long as a necessary insulating effect is obtained. Examples of the material include silicon dioxide, silicon nitride, a fluorine polymer-based insulating material such as polytetrafluoroethylene (PTFE) or CYTOP, a polyester insulating material, a polycarbonate insulating material, an acryl polymer-based insulating material, an epoxy resin-based insulating material, a polyimide insulating material, a polyvinyl phenol resin-based insulating material, a poly p-xylylene resin-based insulating material, and the like.

A surface treatment may be performed on the upper surface of the insulating layer. For example, it is possible to preferably use an insulating layer in which the silicon dioxide surface thereof is subjected to the surface treatment by being coated with hexamethyldisilazane (HMDS), octadecyltrichlorosilane (OTS), or β-phenethyltrimethoxysilane.

(Thickness)

The thickness of the insulating layer is not particularly limited. However, in a case where the film needs to be thinned, the thickness of the insulating layer is preferably 10 nm to 500 nm, more preferably 20 nm to 200 nm, and particularly preferably 50 nm to 200 nm.

<Semiconductor Active Layer>

(Material)

The organic transistor of the present invention is characterized by having a semiconductor active layer containing the compound which is represented by Formula (1) and has a molecular weight of equal to or less than 3,000.

The semiconductor active layer may be a layer composed of the compound which is represented by Formula (1) and has a molecular weight of equal to or less than 3,000 or a layer further containing a polymer binder (referred to as a polymer or a binder as well), which will be described later, in addition to the compound which is represented by Formula (1) and has a molecular weight of equal to or less than 3,000. Furthermore, the semiconductor active layer may contain a residual solvent used at the time of forming a film.

The content of the polymer binder in the semiconductor active layer is not particularly limited. The content of the polymer binder used is preferably within a range of 0% to 95% by mass, more preferably within a range of 10% to 90% by mass, even more preferably within a range of 20% to 80% by mass, and particularly preferably within a range of 30% to 70% by mass.

(Thickness)

The thickness of the semiconductor active layer is not particularly limited. In a case where the film needs to be thinned, the thickness of the semiconductor active layer is preferably 10 nm to 400 nm, more preferably 10 nm to 200 nm, and particularly preferably 10 nm to 100 nm.

[Method for Manufacturing Organic Transistor]

A method for manufacturing an organic transistor of the present invention is characterized by including a step of preparing a semiconductor active layer by coating a substrate with a coating solution for a non-light-emitting organic semiconductor device of the present invention and drying the coating solution.

The coating solution for a non-light-emitting organic semiconductor device of the present invention will be described later.

The method for manufacturing an organic transistor of the present invention may or may not include a method for manufacturing an organic semiconductor film of the present invention that will be described later.

First, general methods in the method for manufacturing an organic transistor of the present invention will be described.

(Film Forming Method)

In the method for manufacturing an organic transistor of the present invention, the compound of the present invention may be formed into a film on a substrate by any method.

At the time of forming the film, the substrate may be heated or cooled. By varying the temperature of the substrate, it is possible to control the film quality or the packing of molecules in the film. The temperature of the substrate is not particularly limited. The temperature is preferably between 0° C. to 200° C., more preferably between 15° C. to 100° C., and particularly preferably between 20° C. to 95° C.

The compound of the present invention can be formed into a film on a substrate by a vacuum process or a solution process, and both of the processes are preferable.

Specific examples of the film forming method by a vacuum process include a physical vapor deposition method such as a vacuum vapor deposition method, a sputtering method, an ion plating method, or a molecular beam epitaxy (MBE) method and a chemical vapor deposition (CVD) method such as plasma polymerization, and it is particularly preferable to use a vacuum vapor deposition method.

Herein, the film forming method by a solution process refers to a method of dissolving an organic compound in a solvent which can dissolve the compound and forming a film by using the solution. Specifically, it is possible to use general methods like a coating method such as a casting method, a dip coating method, a die coater method, a roll coater method, a bar coater method, or a spin coating method, various printing methods such as an ink jet method, a screen printing method, a gravure printing method, a flexographic printing method, an offset printing method, or a micro-contact printing method, and a Langmuir-Blodgett (LB) method. It is particularly preferable to use a casting method, a spin coating method, an ink jet method, a gravure printing method, a flexographic printing method, an offset printing method, or a micro-contact printing method.

The organic semiconductor film for a non-light-emitting organic semiconductor device of the present invention is preferably prepared by a solution coating method. In a case where the organic semiconductor film for a non-light-emitting organic semiconductor device of the present invention contains a polymer binder, it is preferable to prepare a coating solution by dissolving or dispersing a material, which will be formed into a layer, and a polymer binder in an appropriate solvent and to form the organic semiconductor film by various coating methods.

Next, more preferred aspects of the method for manufacturing an organic transistor of the present invention will be described.

[Method for Manufacturing Organic Semiconductor Film]

A preferred method for manufacturing an organic semiconductor film of the present invention is characterized in that in a state where a distance between a substrate A and a member B not being fixed to the substrate A is kept constant or in a state where the substrate A and the member B are caused to remain in contact with each other, a coating solution prepared by dissolving the compound, which is represented by Formula (1) described above and has a molecular weight of equal to or less than 3,000, in a solvent is dropped onto a portion within the surface of the substrate A such that the coating solution contacts both of the substrate A and the member B, and the dropped coating solution is slowly dried, such that crystals of the compound, which is represented by Formula (1) and has a molecular weight of equal to or less than 3,000, are precipitated and a semiconductor active layer is formed; here, as long as the distance between the substrate A and the member B is kept constant or as long as the substrate A and the member B are caused to remain in contact with each other, the positional relationship between the substrate A and the member B may be maintained or changed when the coating solution is dropped or dried.

The preferred method for manufacturing an organic semiconductor film of the present invention will be described based on drawings.

Figure 3A:
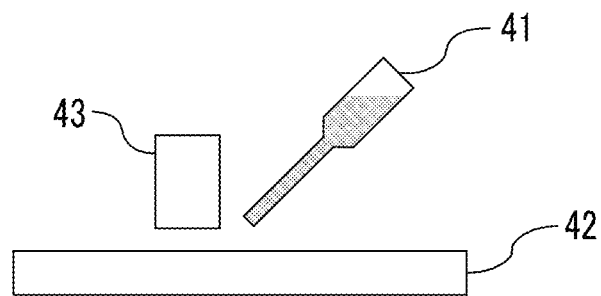
FIGS. 3A to 3C are schematic views showing an example of a method for manufacturing an organic semiconductor film of the present invention. Specifically.
Figure 3B:
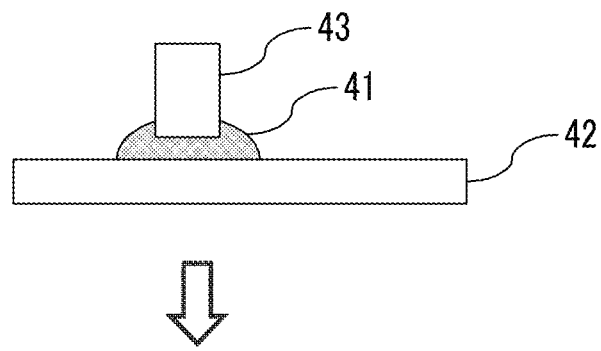
Figure 3C:
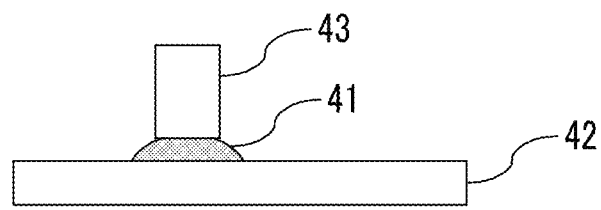

FIGS. 3A to 3C are schematic views showing an example of the method for manufacturing an organic semiconductor film of the present invention.

FIG. 3A shows a state where the coating solution (reference 41) has not yet been dropped onto the substrate A (reference 42). In this state, the distance between the substrate A (reference 42) and the member B (reference 43) not being fixed to the substrate A (reference 42) is kept constant.

FIG. 3B shows a state where the coating solution (reference 41) is then dropped onto a portion within the surface of the substrate A (reference 42) such that the coating solution contacts both of the substrate A (reference 42) and the member B (reference 43).

FIG. 3C is a schematic view showing an aspect in which the dropped coating solution (reference 41) is then slowly dried in a state where the positional relationship between the substrate A (reference 42) and the member B (reference 43) is maintained. The coating solution (reference 41) starts to be dried from both edges where the film thickness is small and is crystallized, and in this way, large-sized crystals can be obtained.

Figure 4A:
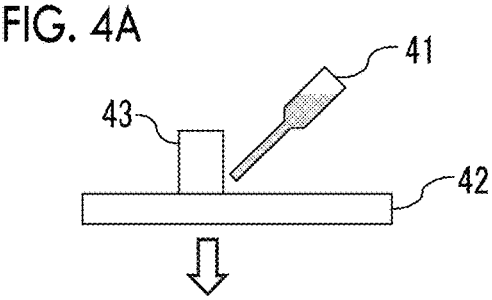
Figure 4A:
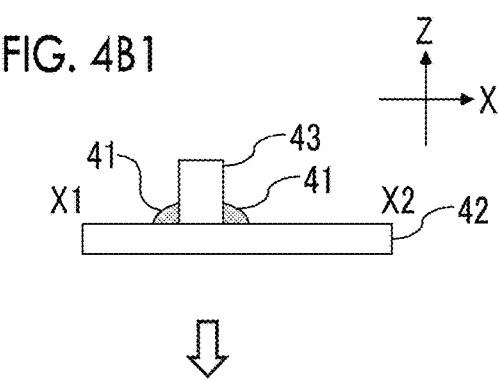
Figure 4A:
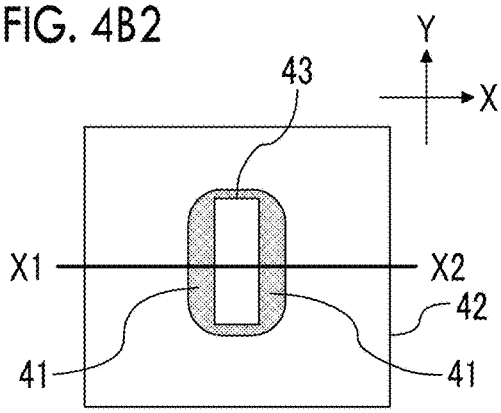
Figure 4C:
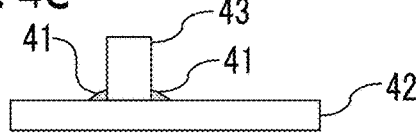

FIGS. 4A to 4C are schematic views showing another example of the method for manufacturing an organic semiconductor film of the present invention.

FIG. 4A shows a state where the coating solution (reference 41) has not yet been dropped onto the substrate A (reference 42). In this state, the substrate A (reference 42) and the member B (reference 43) are caused to remain in contact with each other.

FIG. 4B1 shows a state where the coating solution (reference 41) is then dropped onto a portion within the surface of the substrate A (reference 42) such that the coating solution contacts both of the substrate A (reference 42) and the member B (reference 43). It is FIG. 4B2 that is obtained when FIG. 4B1 is seen in a vertical direction (Y-axis direction). As is evident from FIG. 4B2, the coating solution (reference 41) is dropped on a portion within the surface of the substrate A (reference 42).

FIG. 4C is a schematic view showing an aspect in which the dropped coating solution (reference 41) is then slowly dried in a state where the positional relationship between the substrate A (reference 42) and the member B (reference 43) is maintained. The coating solution (reference 41) starts to be dried from both edges where the film thickness is small and is crystallized, and in this way, large-sized crystals can be obtained.

Comparing the aspect shown in FIGS. 3A to 3C with the aspect shown in FIGS. 4A to 4C, the aspect shown in FIGS. 4A to 4C in which the substrate A (reference 42) and the member B (reference 43) are caused to remain in contact with each other is preferable, because in this aspect, the film quality is excellent, a holding mechanism is not necessary, and the distance between the member B (reference 43) and the substrate A (reference 42) can be accurately maintained.

Figure 5A:
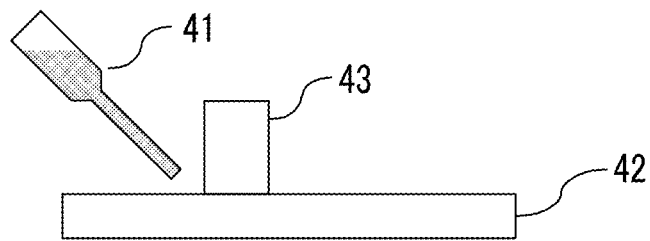
FIGS. 5A to 5C are schematic views showing another example of the method for manufacturing an organic semiconductor film of the present invention. Specifically.
Figure 5B:
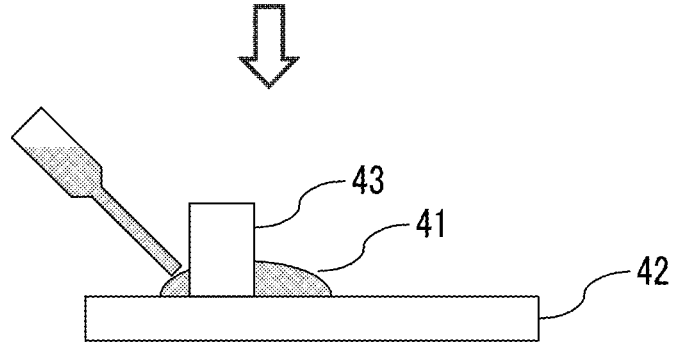
Figure 5C:
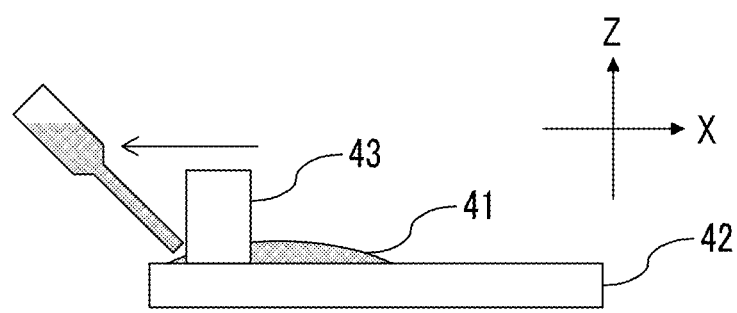

FIGS. 5A to 5C are schematic vies showing another example of the method for manufacturing an organic semiconductor film of the present invention.

FIG. 5A shows a state where the coating solution (reference 41) has not yet been dropped onto the substrate A (reference 42). In this state, the substrate A (reference 42) and the member B (reference 43) are caused to remain in contact with each other.

FIG. 5B shows a state where the coating solution (reference 41) is then dropped onto a portion within the surface of the substrate A (reference 42) such that the coating solution contacts both of the substrate A (reference 42) and the member B (reference 43).

FIG. 5C is a schematic view showing an aspect in which the dropped coating solution is then slowly dried by changing the positional relationship between the substrate A (reference 42) and the member B (reference 43).

In the method for manufacturing an organic semiconductor film of the present invention, as long as the state where the distance between the substrate A and the member B is kept constant or as long as the substrate A and the member B are caused to remain in contact with each other, at the time when the coating solution is dropped or dried, the positional relationship between the substrate A and the member B may be maintained or changed. As shown in FIG. 5C, by changing the the positional relationship between the substrate A (reference 42) and the member B (reference 43) in the −X direction on the coordinates, the coating solution (reference 41) starts to be dried from the edge (+X direction on the coordinates) far away from the member B (reference 43) and is crystallized, and in this way, large-sized crystals can be obtained.

Comparing the aspect shown in FIGS. 5A to 5C with the aspect shown in FIGS. 4A to 4C, the aspect shown in FIGS. 4A to 4C is preferable because in this aspect, the film quality is excellent, and large-sized crystals are easily obtained.

Examples of the substrate A used in the method for manufacturing an organic semiconductor film of the present invention include those used as a substrate of the organic transistor of the present invention. As the substrate A, a substrate in which an insulating layer is formed on the substrate of the organic transistor of the present invention is preferable.

The member B used in the method for manufacturing an organic semiconductor film of the present invention is not particularly limited. The material of the member B is preferably glass; quartz; silicon; Teflon (registered trademark); or plastic such as polyethylene or polypropylene, and more preferably glass.

The size of the member B (reference 43) (for example, the length of the member B (reference 43) in the X-axis direction and the Y-axis direction in FIG. 4B2) is not particularly limited. The lower limit of the length of one side of the member B (reference 43) is preferably equal to or greater than 0.1% of the length of one side of the substrate A (reference 42), more preferably equal to or greater than 1% of the length one side of the substrate A, particularly preferably equal to or greater than 10% of the length of one side of the substrate A, and more particularly preferably equal to or greater than 20% of the length of one side of the substrate A. The upper limit of the length of one side of the member B (reference 43) is preferably equal to or less than 80% of the length of one side of the substrate A (reference 42), more preferably equal to or less than 70% of the length of one side of the substrate A, and particularly preferably equal to or less than 50% of the length of one side of the substrate A.

The height of the member B (reference 43) (for example, the length of the member B (reference 43) in the Z-axis direction in FIG. 4B1) is not particularly limited. The height of the member B (reference 43) is preferably 1 mm to 50 mm, and more preferably 5 mm to 20 mm.

Figure 6:
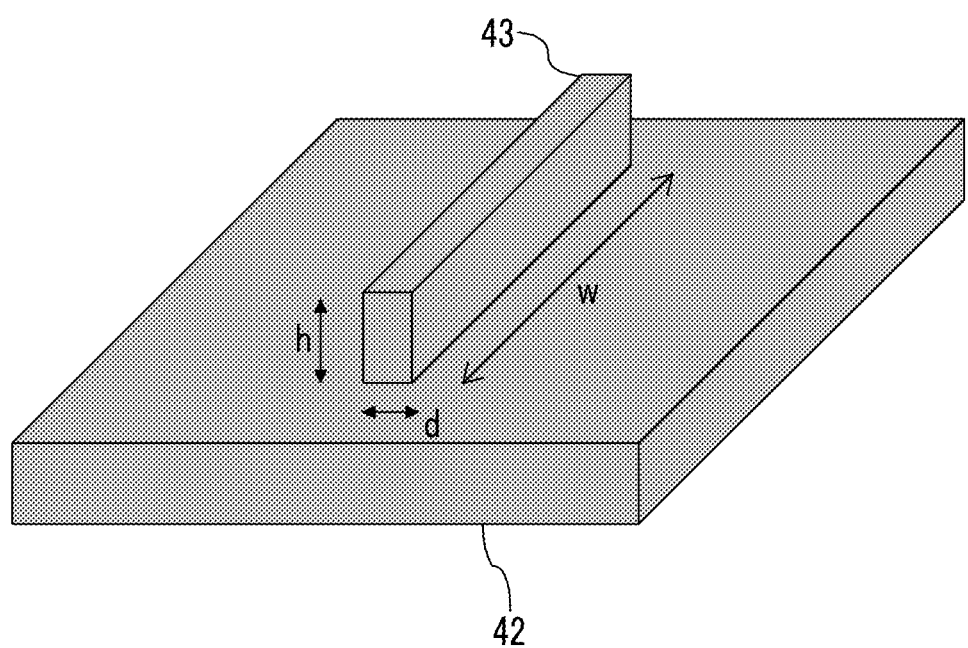
FIG. 6 is a schematic view showing an example of the substrate A and the member B used in the method for manufacturing an organic semiconductor film of the present invention.

FIG. 6 is a schematic view of the substrate A and the member B. In FIG. 6, d indicates the length of the member B in the x-axis direction in FIG. 4B2; w indicates the length of the member B in the y-axis direction in FIG. 4B2; and h indicates the length of the member B in the z-axis direction in FIG. 4B1. h/d in the member B shown in FIG. 6 is preferably 0.01 to 10, and more preferably 0.1 to 5, because then the member B does not collapse. w/d is preferably 1 to 1,000, and more preferably 5 to 100, because then the region in which crystals are formed widens.

(Film Forming Method)

In the method for manufacturing an organic semiconductor film of the present invention, at the time of forming a film, the substrate may be heated or cooled. By varying the temperature of the substrate, it is possible to control the film quality or the packing of molecules in the film. The temperature of the substrate is not particularly limited. However, it is preferably between 0° C. to 200° C., more preferably between 15° C. to 100° C., and particularly preferably between 20° C. to 95° C.

When the compound of the present invention is formed into a film on the substrate, a solution process is used for forming the film.

Herein, the film forming method by a solution process refers to a method of dissolving an organic compound in a solvent which can dissolve the compound and forming a film by using the solution. Specifically, it is possible to use general methods like various printing methods such as a drop casting method, an ink jet method, a screen printing method, a gravure printing method, a flexographic printing method, an offset printing method, and a micro-contact printing method. Among these, an ink jet method, a gravure printing method, a flexographic printing method, an offset printing method, and a micro-contact printing method are preferably used, and a flexographic printing method, a micro-contact printing method, and an ink jet method are particularly preferably used.

(Coating Solution/Coating Solution for Non-Light-Emitting Organic Semiconductor Device)

Hereinafter, a coating solution for a non-light-emitting organic semiconductor device of the present invention that can be used as a coating solution for the method for manufacturing an organic semiconductor film of the present invention will be described.

The present invention also relates to a coating solution for a non-light-emitting organic semiconductor device containing the compound which is represented by Formula (1) and has a molecular weight of equal to or less than 3,000.

In a case where a film is formed on a substrate by using a solution process, by using a coating solution, which is obtained by dissolving or dispersing a material for forming a layer in an appropriate organic solvent (for example, a hydrocarbon-based solvent such as hexane, octane, decane, toluene, xylene, mesitylene, ethylbenzene, amylbenzene, decalin, 1-methylnaphthalene, 1-ethylnaphthalene, 1,6-dimethylnaphthalene, or tetralin, a ketone-based solvent such as acetone, methyl ethyl ketone, methyl isobutyl ketone, cyclohexanone, acetophenone, propiophenone, or butyrophenone, a halogenated hydrocarbon-based solvent such as dichloroethane, chloroform, tetrachloromethane, dichloroethane, trichloroethane, tetrachloroethane, chlorobenzene, 1,2-dichlorobenzene, 1,2,4-trichlorobenzene, chlorotoluene, or 1-fluoronaphthalene, a heterocyclic solvent such as pyridine, picoline, quinoline, thiophene, 3-butylthiophene, or thieno[2,3-b]thiophene, a halogenated heterocyclic solvent such as 2-chlorothiophene, 3-chlorothiophene, 2,5-dichlorothiophene, 3,4-dichlorothiophene, 2-bromothiophene, 3-bromothiophene, 2,3-dibromothiophene, 2,4-dibromothiophene, 2,5-dibromothiophene, 3,4-dibromothiophene, or 3,4-dichloro-1,2,5-thiadiazole, an ester-based solvent such as ethyl acetate, butyl acetate, amyl acetate, 2-ethylhexyl acetate, γ-butyrolactone, or phenyl acetate, an alcohol-based solvent such as methanol, propanol, butanol, pentanol, hexanol, cyclohexanol, methyl cellosolve, ethyl cellosolve, or ethylene glycol, an ether-based solvent such as dibutyl ether, tetrahydrofuran, dioxane, dimethoxyethane, anisole, ethoxybenzene, propoxybenzene, isopropoxybenzene, butoxybenzene, 2-methylanisole, 3-methylanisole, 4-methylanisole, 4-ethylanisole, dimethylanisole (any of 2,3-, 2,4-, 2,5-, 2,6-, 3,4-, 3,5-, and 3,6-dimethylanisoles), or 1,4-benzodioxane, an amide/imide-based solvent such as N,N-dimethylformamide, N,N-dimethylacetamide, 1-methyl-2-pyrrolidone, 1-methyl-2-imidazolidinone, or 1,3-dimethyl-2-imidazolidinone, a sulfoxide-based solvent such as dimethylsulfoxide, a phosphoric acid ester-based solvent such as trimethyl phosphate, a nitrile-based solvent such as acetonitrile or benzonitrile, a nitro-based solvent such as nitromethane or nitrobenzene) and/or water, a film can be formed by various coating methods. One kind of solvent may be used singly, or plural kinds thereof may be used in combination. Among these, a hydrocarbon-based solvent, a halogenated hydrocarbon-based solvent, a heterocyclic solvent, a halogenated heterocyclic solvent, or an ether-based solvent is preferable, toluene, xylene, mesitylene, amylbenzene, tetralin, acetophenone, propiophenone, butyrophenone, dichlorobenzene, anisole, ethoxybenzene, propoxybenzene, isopropoxybenzene, butoxybenzene, 2-methylanisole, 3-methylanisole, 4-methylanisole, 1-fluoronaphthalene, 3-chlorothiophene, and 2,5-dibromothiophene are more preferable, and toluene, xylene, tetralin, acetophenone, propiophenone, butyrophenone, anisole, ethoxybenzene, propoxybenzene, butoxybenzene, 2-methylanisole, 3-methylanisole, 4-methylanisole, 1-fluoronaphthalene, 3-chlorothiophene, and 2,5-dibromothiophene are particularly preferable.

Among the above solvents, it is preferable to use solvents having a boiling point of equal to or higher than 100° C. for the coating solution for a non-light-emitting organic semiconductor device of the present invention, because then the film quality becomes excellent, and crystals with a large area are easily obtained. The solvent having a boiling point of equal to or higher than 100° C. is preferably used in the method for manufacturing an organic semiconductor film of the present invention.

Among the above solvents, examples of the solvents having a boiling point of equal to or higher than 100° C. include toluene, xylene, mesitylene, tetralin, acetophenone, propiophenone, butyrophenone, dichlorobenzene, anisole, ethoxybenzene, propoxybenzene, isopropoxybenzene, butoxybenzene, 2-methylanisole, 3-methylanisole, and 4-methylanisole. Among these, toluene, xylene, tetralin, acetophenone, propiophenone, butyrophenone, anisole, ethoxybenzene, propoxybenzene, butoxybenzene, 2-methylanisole, 3-methylanisole, and 4-methylanisole are more preferable.

From the viewpoint of environmental load and toxicity to human beings, the solvents having a boiling point of equal to or higher than 100° C. are preferably non-halogen-based solvents.

The concentration of the compound, which is represented by Formula (1) and has a molecular weight of equal to or less than 3,000, in the coating solution is preferably 0.005% to 5% by mass, more preferably 0.01% to 3% by mass, and particularly preferably 0.02% to 1% by mass. If the concentration is within the above range, it is easy to form a film at any thickness. In the coating solution for a non-light-emitting organic semiconductor device, the concentration of the compound represented by Formula (1) is particularly preferably equal to or greater than 0.4% by mass, because then a coating film composed of large-sized crystals is easily formed. In Tetrahedron 66 (2010) 8778-8784, a film for measuring oxidation-reduction potential is manufactured using a coating solution containing C6-TBBT or C12-TBBT at low concentration. For the same reason as described above, it is preferable that the concentration of the coating solution for a non-light-emitting organic semiconductor device is high.

In the method for manufacturing an organic semiconductor film of the present invention, the coating solution is dropped onto a portion within the surface of the substrate A such that the coating solution contacts both of the substrate A and the member B.

At the time of dropping the coating solution, it is preferable to drop a single drop of the coating solution or to drop the coating solution drop by drop in a case where two or more drops of the coating solution are dropped, because then a portion in which a film of the coating solution having a small thickness is easily formed on the substrate A, and it is easy to accelerate drying of the coating solution from edge.

In a case where the coating solution is dropped, the volume of a single drop of the coating solution is preferably 0.01 ml to 0.2 ml, and more preferably 0.02 ml to 0.1 ml.

By dropping the coating solution onto a portion within the surface of the substrate A such that the coating solution contacts both of the substrate A and the member B, it is possible to reduce the film thickness at the edge of the coating solution.

The contact angle between the coating solution and the substrate A is preferably 0° to 90°, and more preferably 10° to 80°.

The coating solution and the member B preferably form a meniscus, and more preferably form a concave meniscus from the viewpoint of the film quality.

Usually, in order to form a film by a solution process, the material needs to dissolve in the solvent exemplified above, but simply dissolving in a solvent is not good enough. Generally, even the material formed into a film by a vacuum process can dissolve in a solvent to some extent. The solution process includes a step of coating a substrate with a material by dissolving the material in a solvent and then forming a film by evaporating the solvent, and many of the materials not being suitable for being formed into a film by the solution process have high crystallinity. Therefore, the material is inappropriately crystallized (aggregated) in the aforementioned step, and hence it is difficult to form an excellent film. This problem has been considered in the related art. In contrast, according to the method for manufacturing an organic semiconductor film of the present invention, it is possible to form an organic semiconductor film in a state of causing the precipitation of crystals.

For the coating solution for a non-light-emitting organic semiconductor device of the present invention, an aspect is also preferable in which the coating solution contains the compound, which is represented by Formula (1) and has a molecular weight of equal to or less than 3,000, but does not contain a polymer binder.

Furthermore, the coating solution for a non-light-emitting organic semiconductor device of the present invention may contain the compound, which is represented by Formula (1) and has a molecular weight of equal to or less than 3,000, and a polymer binder. In this case, by using a coating solution obtained by dissolving or dispersing a material for forming a layer and the polymer binder in an appropriate solvent described above, a film can be formed by various coating methods. The polymer binder can be selected from those described above.

From the viewpoint of the uniformity of the film quality of the coating film to be formed, the coating solution for a non-light-emitting organic semiconductor device preferably contains a polymer.

The coating solution for a non-light-emitting organic semiconductor device may contain only one kind of compound represented by Formula (2) or contain two or more kinds thereof. From the viewpoint of the storage stability (inhibition of crystal precipitation during storage) of the coating solution, the coating solution preferably contains two or more kinds of compound represented by Formula (2).

From the viewpoint of the suitability for various printing methods, the coating solution for a non-light-emitting organic semiconductor device preferably has a viscosity of equal to or greater than 10 mPa·s.

The coating solution for a non-light-emitting organic semiconductor device may contain additives other than a polymer binder, such as a surfactant, an antioxidant, a crystallization control agent, and a crystal orientation control agent.

Examples of the surfactant are not particularly limited and include nonionic surfactants such as polyoxyethylene alkyl ethers, polyoxyethylene alkyl allyl ethers, polyoxyethylene-polyoxypropylene block copolymers, sorbitan fatty acid esters, and a polyoxyethylene sorbitan fatty acid ester; fluorine-based surfactants such as MEGAFACE F171 and F176 (manufactured by DIC Corporation), FLUORAD FC430 (manufactured by Sumitomo 3M Ltd.), SURFYNOL E1004 (manufactured by ASAHI GLASS CO., LTD.), and PF656 and PF6320 manufactured by OMNOVA Solutions Inc.; and organosiloxane polymers such as polysiloxane polymers KP-341 (manufactured by Shin-Etsu Chemical Co., Ltd.), KF-410 (manufactured by Shin-Etsu Chemical Co., Ltd.), KF-412 (manufactured by Shin-Etsu Chemical Co., Ltd.), KF-96-100cs (manufactured by Shin-Etsu Chemical Co., Ltd.), BYK-322 (manufactured by BYK Additives & Instruments), and BYK-323 (manufactured by BYK Additives & Instruments).

The content of the surfactant in the coating solution is preferably about 0.001% to about 1% by mass.

Examples of the antioxidant include a phenol-based antioxidant, a phosphorus-based antioxidant, a sulfur-based antioxidant, and the like.

Specific examples of the phenol-based antioxidant include 2,6-di-t-butyl-4-methylphenol, n-octadecyl-3-(3',5'-di-t-butyl-4'-hydroxyphenyl)propionate, tetrakis[methylene-3-(3,5-di-t-butyl-4-hydroxyphenyl)propionate]methane, tris(3,5-di-t-butyl-4-hydroxybenzyl)isocyanurate, 4,4'-butylidenebis-(3-methyl-6-t-butylphenol), triethylene glycol bis[3-(3-t-butyl-4-hydroxy-5-methylphenyl)propionate], and 3,9-bis{2-[3-(3-t-butyl-4-hydroxy-5-methylphenyl)propionyloxy]-1,1-dimethylethyl}-2,4,8,10-tetraoxaspiro[5,5] undecane.

Examples of commercially available products of the phenol-based antioxidant include IRGANOX 1010, IRGANOX 1035, IRGANOX 1076, IRGANOX 1135, IRGANOX 245, IRGANOX 259, IRGANOX 295, and IRGANOX 3114 (all manufactured by BASF SE), ADEKA STAB AO-20, ADEKA STAB AO-30, ADEKA STAB AO-40, ADEKA STAB AO-50, ADEKA STAB AO-60, ADEKA STAB AO-70, ADEKA STAB AO-80, ADEKA STAB AO-90, and ADEKA STAB AO-330 (all manufactured by ADEKA Corporation), SUMILIZER BHT, SUMILIZER BP-101, SUMILIZER GA-80, SUMILIZER MDP-S, SUMILIZER BBM-S, SUMILIZER GM, SUMILIZER GS(F), and SUMILIZER GP (all manufactured by Sumitomo Chemical Co., Ltd.), HOSTANOX O10, HOSTANOX O16, HOSTANOX O14, and HOSTANOX O3 (all manufactured by CLARIANT), ANTAGE BHT, ANTAGE W-300, ANTAGE W-400, and ANTAGE W-500 (all manufactured by Kawaguchi Chemical Industry Co., LTD.), SEENOX 224M and SEENOX 326 M (all manufactured by SHIPRO KASEI KAISHA, LTD.), YOSHINOX BHT, YOSHINOX BB, TOMINOX TT, and TOMINOX 917 (all manufactured by YOSHITOMI PHARMACEUTICAL INDUSTRIES, LTD.), TTHP (manufactured by TORAY INDUSTRIES, INC.), and the like.

Specific examples of the phosphorus-based antioxidant include trisnonylphenyl phosphite, tris(2,4-di-t-butylphenyl) phosphite, distearyl pentaerythritol diphosphite, bis(2,4-di-t-butylphenyl)pentaerythritol phosphite, bis(2,6-di-t-butyl-4-methylphenyl)pentaerythritol phosphite, 2,2-methylenebis(4,6-di-t-butylphenyl)octylphosphite, tetrakis (2,4-di-t-butylphenyl)-4,4-biphenylene-di-phosphonite, and the like. Examples of commercially available products of the phosphorus-based antioxidant include ADEKA STAB 1178 (manufactured by ADEKA Corporation), SUMILIZER TNP (manufactured by Sumitomo Chemical Co., Ltd.), JP-135 (manufactured by JOHOKU CHEMICAL CO., LTD), ADEKA STAB 2112 (manufactured by ADEKA Corporation), JPP-2000 (manufactured by JOHOKU CHEMICAL CO., LTD), WESTON 618 (manufactured by General Electric), ADEKA STAB PEP-24G (manufactured by ADEKA Corporation), ADEKA STAB PEP-36 (manufactured by ADEKA Corporation), ADEKA STAB HP-10 (manufactured by ADEKA Corporation), SANDSTAB P-EPQ (manufactured by Sandoz), PHOSPHITE 168 (manufactured by Ciba Specialty Chemicals, Inc.), and the like.

Specific examples of the sulfur-based antioxidant include dilauryl-3,3'-thiodipropionate, dimyristyl-3,3'-thiodipropionate, distearyl-3,3'-thiodipropionate, pentaerythritol tetrakis(3-laurylthiopropionate), and the like. Examples of commercially available products of the sulfur-based antioxidant include SUMILIZER TPL (manufactured by Sumitomo Chemical Co., Ltd.), YOSHINOX DLTP (manufactured by YOSHITOMI PHARMACEUTICAL INDUSTRIES, LTD.), ANTIOX L (manufactured by NOF CORPORATION), SUMILIZER TPM (manufactured by Sumitomo Chemical Co., Ltd.), YOSHINOX DMTP (manufactured by YOSHITOMI PHARMACEUTICAL INDUSTRIES, LTD.), ANTIOX M (manufactured by NOF CORPORATION), SUMILIZER TPS (manufactured by Sumitomo Chemical Co., Ltd.), YOSHINOX DSTP (manufactured by YOSHITOMI PHARMACEUTICAL INDUSTRIES, LTD.), ANTIOX S (manufactured by NOF CORPORATION), ADEKA STAB AO-4125 (manufactured by ADEKA Corporation), SEENOX 412S (manufactured by SHIPRO KASEI KAISHA, LTD.), SUMILIZER TDP (manufactured by Sumitomo Chemical Co., Ltd.), and the like.

The content of the antioxidant in the coating solution is preferably about 0.01% to 5% by mass.

(Drying)

In the method for manufacturing an organic semiconductor film of the present invention, the dropped coating solution is slowly dried so as to cause the precipitation of crystals of the compound which is represented by Formula (1) and has a molecular weight of equal to or less than 3,000, thereby forming a semiconductor active layer.

From the viewpoint of the film quality, it is preferable that the coating solution is air-dried on the heated substrate A and then dried under reduced pressure.

The temperature of the substrate A at the time of air drying is preferably 20° C. to 100° C., and more preferably 50° C. to 80° C.

The air drying is preferably performed for 0.5 hours to 20 hours, and more preferably performed for 1 hour to 10 hours.

The temperature at the time of drying under reduced pressure is preferably 20° C. to 100° C., and more preferably 40° C. to 80° C.

The drying under reduced pressure is preferably performed for 1 hour to 20 hours, and more preferably performed for 2 hours to 10 hours.

The pressure at the time of drying under reduced pressure is preferably $10^{-6}$ Pa to $10^{-2}$ Pa, and more preferably $10^{-5}$ Pa to $10^{-3}$ Pa.

In the method for manufacturing an organic semiconductor film of the present invention, crystals of the compound which is represented by Formula (1) and has a molecular weight of equal to or less than 3,000 are precipitated.

Whether or not the crystals have been precipitated can be checked by observation using a polarizing microscope.

[Organic Semiconductor Material for Non-Light-Emitting Organic Semiconductor Device]

The present invention also relates to an organic semiconductor material for a non-light-emitting organic semiconductor device containing the compound which is represented by Formula (1) and has a molecular weight of equal to or less than 3,000.

(Non-Light-Emitting Organic Semiconductor Device)

In the present specification, a "non-light-emitting organic semiconductor device" refers to a device which is not used for the purpose of emitting light. Particularly, a "non-light-emitting organic semiconductor device" refers to a device which is not used for the purpose of emitting visible light. The non-light-emitting organic semiconductor device preferably uses an electronic element having a layered structure consisting of films. The non-light-emitting organic semiconductor device includes an organic transistor, an organic photoelectric conversion element (a solid-state imaging element used for a photosensor, a solar cell used for energy conversion, or the like), a gas sensor, an organic rectifying element, an organic inverter, an information recording element, and the like. The organic photoelectric conversion element can be used for a photosensor (solid-state imaging element) and for energy conversion (a solar cell). Among these, an organic photoelectric conversion element and an organic transistor are preferable, and an organic transistor is more preferable. That is, the organic semiconductor material for a non-light-emitting organic semiconductor device of the present invention is preferably a material for an organic transistor as described above.

(Organic Semiconductor Material)

In the present specification, the "organic semiconductor material" is an organic material showing characteristics of a semiconductor. Just as a semiconductor composed of an inorganic material, the organic semiconductor is classified into a p-type (hole-transporting) organic semiconductor material conducting holes as carriers and an n-type (electron-transporting) organic semiconductor material conducting electrons as carriers.

The compound of the present invention may be used as any of the p-type organic semiconductor material and the n-type organic semiconductor material, but is preferably used as the p-type. The ease with which the carriers flow in the organic semiconductor is represented by a carrier mobility μ. The higher the carrier mobility μ, the better. The carrier mobility μ is preferably equal to or greater than $1 \times 10^{-1}$ cm$^2$/Vs, more preferably equal to or greater than $1 \times 10^{-1}$ cm$^2$/Vs, particularly preferably equal to or greater than $3 \times 10^{-1}$ cm$^2$/Vs, more particularly preferably equal to or greater than $5 \times 10^{-1}$ cm$^2$/Vs, and even more particularly preferably equal to or greater than 1 cm$^2$/Vs. The carrier mobility μ can be determined by the characteristics of the prepared field effect transistor (FET) element or by a time-of-flight (TOF) measurement method.

[Organic Semiconductor Film for Non-Light-Emitting Organic Semiconductor Device]

An organic semiconductor film for a non-light-emitting organic semiconductor device of the present invention contains the compound which is represented by Formula (1) and has a molecular weight of equal to or less than 3,000.

The organic semiconductor film for a non-light-emitting organic semiconductor device of the present invention is preferably manufactured by the method for manufacturing an organic semiconductor film of the present invention.

(Material)

The present invention also relates to the organic semiconductor film for a non-light-emitting organic semiconductor device containing the compound which is represented by Formula (1) and has a molecular weight of equal to or less than 3,000.

For the organic semiconductor film for a non-light-emitting organic semiconductor device of the present invention, an aspect is also preferable in which the film contains the compound, which is represented by Formula (1) and has a molecular weight of equal to or less than 3,000, and does not contains a polymer binder.

Furthermore, the organic semiconductor film for a non-light-emitting organic semiconductor device of the present invention may contain the compound, which is represented by Formula (1) and has a molecular weight of equal to or less than 3,000, and a polymer binder.

Examples of the polymer binder include an insulating polymer such as polystyrene, polycarbonate, polyarylate, polyester, polyamide, polyimide, polyurethane, polysiloxane, polysulfone, polymethyl methacrylate, polymethyl acrylate, cellulose, polyethylene, or polypropylene, a copolymer of these, rubber or a thermoplastic elastomer such as ethylene-propylene rubber, acrylonitrile-butadiene rubber, hydrogenated nitrile rubber, fluoro-rubber, a perfluoro elastomer, a tetrafluoroethylene-propylene copolymer, an ethylene-propylene-diene copolymer, styrene-butadiene rubber, polychloroprene, polyneoprene, butyl rubber, a methyl/phenyl silicone resin, a methyl/phenylvinyl/silicone resin, a methyl/vinyl/silicone resin, a fluorosilicone resin, acryl rubber, ethylene acryl rubber, chlorosulfonated polyethylene, chloropolyethylene, an epichlorohydrin copolymer, a polyisoprene-natural rubber copolymer, polyisoprene rubber, a styrene-isoprene block copolymer, a polyester-urethane copolymer, a polyether-urethane copolymer, a polyether ester thermoplastic elastomer, and polybutadiene rubber, a photoconductive polymer such as polyvinylcarbazole or polysilane, a conductive polymer such as polythiophene, polypyrrole, polyaniline, or poly p-phenylenevinylene, and a semiconductor polymer described in, for example, Chemistry of Materials, 2014, 26, 647.

One kind of polymer binder may be used singly, or plural kinds thereof may be used in combination.

The organic semiconductor material may be uniformly mixed with the polymer binder. Alternatively, the organic semiconductor material and the polymer binder may be totally or partially in a phase separation state. From the viewpoint of the charge mobility, a structure, in which the organic semiconductor and the binder are in a phase separation state along the film thickness direction in the film, is the most preferable because then the binder does not hinder the organic semiconductor from moving a charge.

Considering the mechanical strength of the film, a polymer binder having a high glass transition temperature is preferable. However, for the purpose of imparting flexibility to the film, a polymer binder having a low glass transition temperature is preferable. Considering the charge mobility, a polymer binder having a structure not containing a polar group and a conductive polymer are preferable.

The amount of the polymer binder used is not particularly limited. However, in the organic semiconductor film for a non-light-emitting organic semiconductor device of the present invention, the amount of the polymer binder used is preferably within a range of 0% to 95% by mass, more preferably within a range of 10% to 90% by mass, even more preferably within a range of 20% to 80% by mass, and particularly preferably within a range of 30% to 70% by mass.

In the present invention, because the compound which is represented by Formula (1) and has a molecular weight of equal to or less than 3,000 has the aforementioned structure, an organic film having excellent film quality can be obtained. Specifically, because the compound obtained in the present invention has excellent crystallinity, a sufficient film thickness can be obtained, and the obtained organic semiconductor film for a non-light-emitting organic semiconductor device of the present invention has excellent quality.

In addition, in a case where the organic semiconductor film for a non-light-emitting organic semiconductor device of the present invention is manufactured by the method for manufacturing an organic semiconductor film of the present invention, the organic semiconductor film becomes an organic film having excellent film quality.

EXAMPLES

Hereinafter, the characteristics of the present invention will be more specifically explained by describing examples and comparative examples. The materials, the amount thereof used, the proportion thereof, the content of treatment, the treatment procedure, and the like described in the following examples can be appropriately modified within a range that does not depart from the gist of the present invention. Accordingly, the scope of the present invention is not limited to the following specific examples.

Example 1 and Comparative Examples 1 to 5

<Synthesis Method>
A compound 1 of the present invention was synthesized according to the following scheme.
Synthesis of Intermediate 1

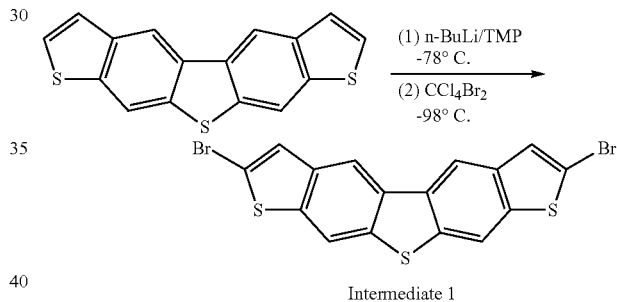

Intermediate 1

Synthesis of Intermediate 2

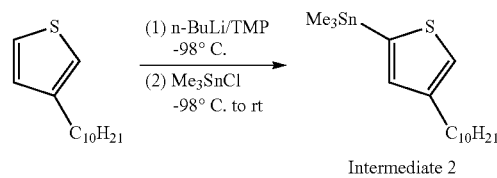

Intermediate 2

Synthesis of Compound 1

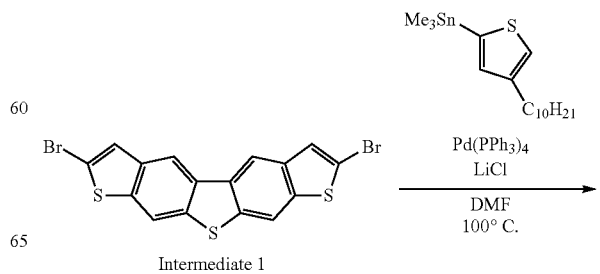

Intermediate 1

-continued

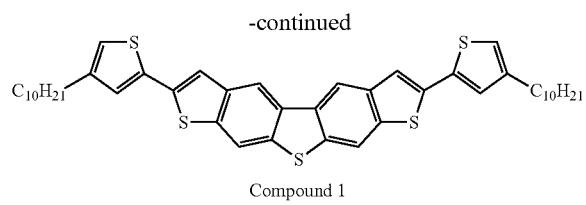

Compound 1

(Synthesis of Intermediate 1)

23.1 ml of tetrahydrofuran was added to 3.93 ml of tetramethylpiperidine (TMP), followed by stirring at −78° C., and 13.8 ml of n-butyllithium (1.6 M hexane solution) was added thereto. Then, the mixture was heated to 0° C. and stirred for 1 hour, thereby preparing a lithium reagent.

100 ml of tetrahydrofuran was added to 2.969 g (10 mmol) of thieno[3,2-f:4,5-f']bis[1]benzothiophene, followed by stirring at −78° C., and the aforementioned lithium reagent was added dropwise thereto at −78° C. by using a cannula. After 2 hours, the reaction solution was cooled to −98° C., and a solution obtained by dissolving 9.76 g (30 mmol) of dibromodichloroethane in 30 ml of tetrahydrofuran was added dropwise thereto by using a cannula. Then, the reaction solution was slowly heated to room temperature from −98° C. and stirred for 15 hours. After the reaction solution was cooled to 0° C., water was added thereto, and the precipitate was separated by filtration. The solid separated by filtration was recrystallized from 1,1,2,2-tetrachloroethane, thereby obtaining 3.95 g (8.70 mmol) of a target compound (intermediate 1). The obtained compound was identified by $^1$H-NMR. $^1$H-NMR (Tetrachloroethane-d$_2$, 400 MHz) δ: 7.46 (2H, s), 8.12 (2H, s), 8.45 (2H, s)

(Synthesis of Intermediate 2)

30 ml of tetrahydrofuran was added to 4.49 g (20 mmol) of 3-decylthiophene, followed by stirring at −98° C., and 21 mmol of a lithium reagent prepared in the same manner as descried above was added thereto, followed by stirring for 2 hours. Then, a solution obtained by dissolving 4.58 g (23.0 mmol) of trimethyltin chloride in 30 ml of tetrahydrofuran was added dropwise to the reaction solution, and the reaction solution was slowly heated to room temperature from −98° C., followed by stirring for 15 hours. Thereafter, water was added to the reaction solution, and extraction was performed using ethyl acetate, followed by purification through distillation, thereby obtaining 6.04 g (15.6 mmol) of a target compound (intermediate 2).

(Synthesis of compound 1)

7.5 ml of N,N-dimethylformamide was added to 341 mg (0.75 mmol) of the intermediate 1, 755 mg (1.95 mmol) of the intermediate 2, and 83 mg (1.95 mmol) of lithium chloride, followed by deaeration. Then, 43 mg (0.0375 mmol) of tetrakistriphenylphosphine palladium (0) was added thereto, followed by heating for 15 hours at 100° C. and stirring. After the reaction ended, the reaction solution was cooled to room temperature, and the precipitated solid was separated by filtration and washed with N,N-dimethylformamide. The solid was dissolved in o-dichlorobenzene at 120° C. and subjected to hot filtration through silica and celite, and the filtrate was concentrated, thereby obtaining a solid. The obtained solid was recrystallized from o-dichlorobenzene, thereby obtaining 476 mg (0.642 mmol) of a target compound (compound 1). The structure of the compound 1 was identified by $^1$H-NMR, and the results are as follows.

$^1$H-NMR (tetrachloroethane-d$_2$, 400 MHz) δ: 0.86 (6H, t), 1.25-1.32 (28H, m), 1.62-1.73 (4H, m), 2.60 (4H, t), 6.93 (2H, s), 7.16 (2H, s), 7.50 (2H, s), 8.18 (2H, s), 8.48 (2H, s).

Compounds 2 to 12 having the following structures were synthesized according to the synthesis methods which will be described later.

Compound 2

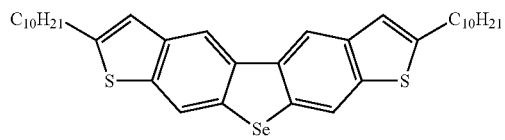

Compound 3

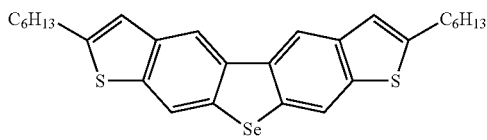

Compound 4

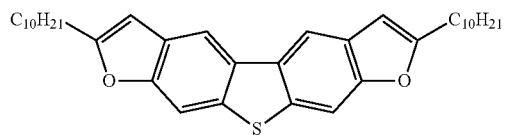

Compound 5

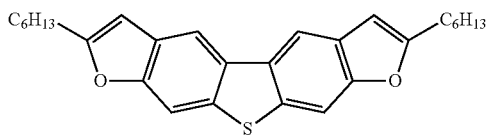

Compound 6

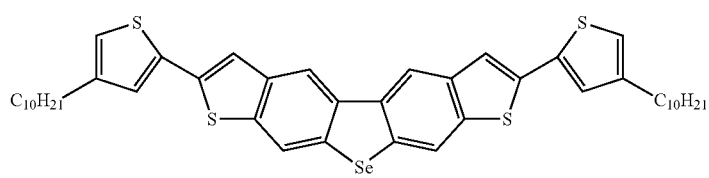

Compound 7

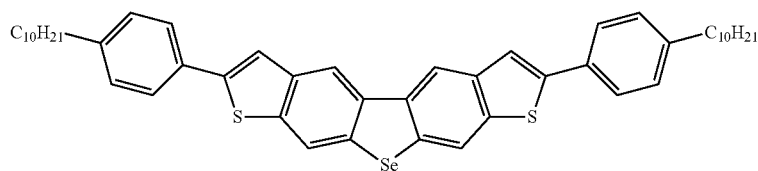

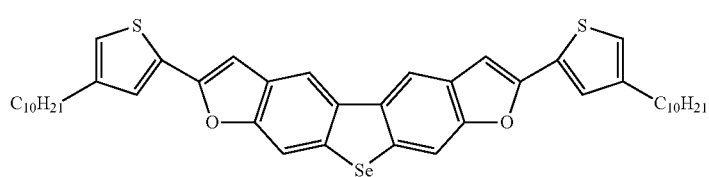

Compound 8

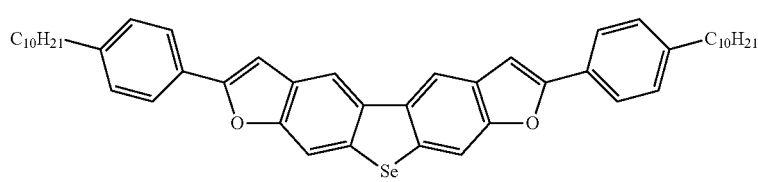

Compound 9

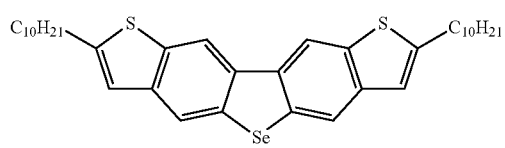

Compound 10

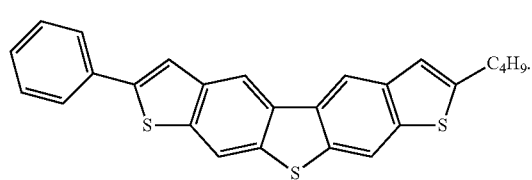

Compound 11

Compound 12

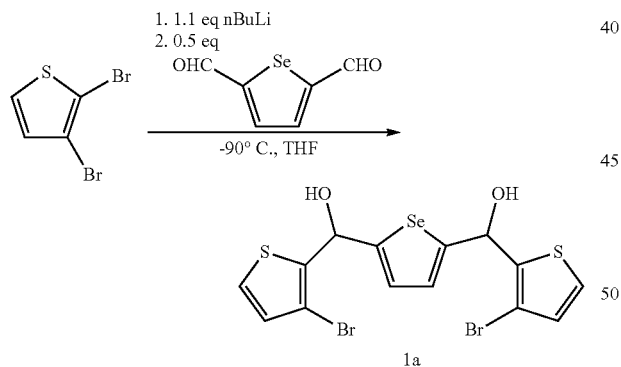

(Synthesis of Compound 2)

—Synthesis of Intermediate 1a—

A 2,3-dibromothiophene n-butyllithium solution (15.9 g, 65.8 mmol) was dissolved in 120 ml of diethylether. Then, n-butyllithium (1.6 M solution) was added dropwise to the solution that was being stirred at −90° C. After 30 minutes, a solution obtained by dissolving 2,5-selenophene dicarboxaldehyde (6.00 g, 32.1 mmol) in 50 ml tetrahydrofuran was added dropwise thereto, followed by stirring for 20 minutes at −78° C., and then the reaction solution was heated to room temperature. The reaction solution was quenched with water, and an organic layer was extracted using diethylether and dried over magnesium sulfate. The organic layer was concentrated using an evaporator, thereby obtaining an intermediate 1a (12.9 g) as a target substance in the form of brown oil. The obtained crude target substance was used for the next reaction without being further purified.

$^1$H-NMR (CDCl$_3$, 400 MHz) δ: 7.28 (d, J=5.2 Hz, 2H), 7.04 (d, J=5.2 Hz, 2H), 6.93 (d, J=5.2 Hz, 2H), 6.31 (s, 2H).

—Synthesis of Intermediate 2a—

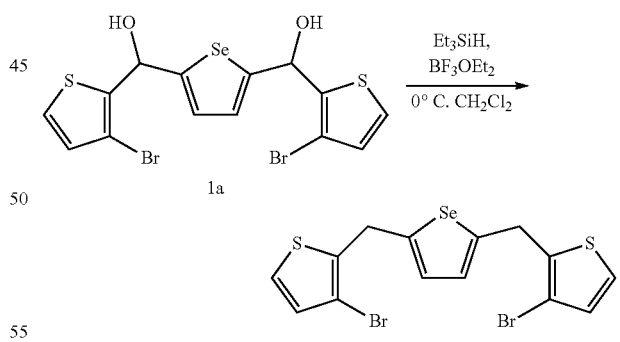

The intermediate 1a (12.9 g) and triethylsilane (15.4 ml, 96.2 mmol) were dissolved in 70 ml of dichloroethane and cooled to 0° C. To the obtained solution, boron trifluoride/etherate (11.9 ml, 96.2 mmol) was added dropwise, followed by stirring for 30 minutes. Then, the reaction solution was quenched with water, and an organic layer was extracted using ethyl acetate and dried over magnesium sulfate. The crude substance obtained after concentration was purified by column chromatography (hexane:ethyl acetate=95:5), thereby obtaining an intermediate 2a (9.20 g, 19.1 mmol, 60% yield for 2 steps) as a target substance in the form of yellow oil.

$^1$H-NMR (CDCl$_3$, 400 MHz) δ: 7.16 (d, J=5.2 Hz, 2H), 6.92 (d, J=5.2 Hz, 2H), 6.86 (s, 2H), 4.28 (s, 4H).

—Synthesis of Intermediate 3a—

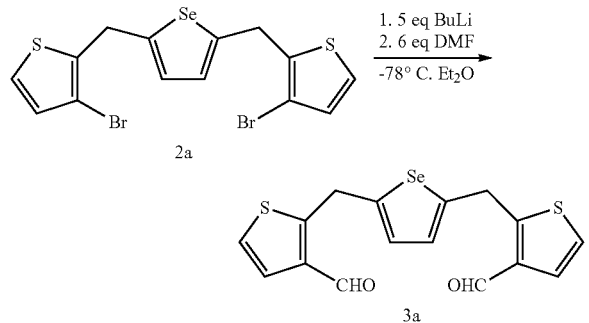

n-Butyllithium (1.6 M solution) (58.5 ml, 93.5 mmol) was cooled to −78° C. At this point in time, a solution obtained by dissolving the intermediate 2a (9.00 g, 18.7 mmol) in 240 ml of diethylether was added dropwise thereto, followed by stirring for 30 minutes. Then, N,N-dimethylformamide (8.7 ml, 112 mmol) was added dropwise thereto. After being stirred for 20 minutes at −78° C., the reaction solution was heated to room temperature, then quenched with water, and subjected to extraction using diethylether, and the extract was dried over magnesium sulfate. Through concentration, an intermediate 3a (6.50 g) as a target substance in the form of red oil was obtained. The obtained crude target substance was used for the next reaction without being further purified.

$^1$H-NMR (CDCl$_3$, 400 MHz) δ: 10.0 (s, 2H), 7.40 (d, J=4.8 Hz, 2H), 7.15 (d, J=4.8 Hz, 2H), 6.88 (s, 2H), 4.68 (s, 4H).

—Synthesis of Intermediate 4a—

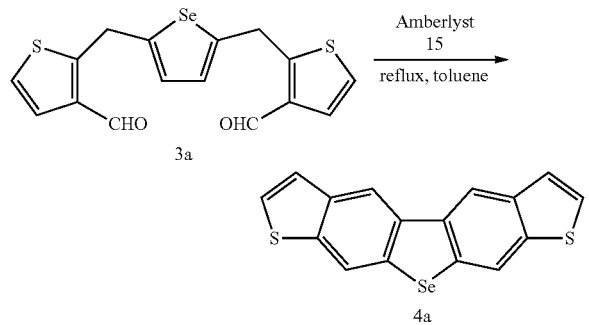

The intermediate 3a (6.50 g) was dissolved in 350 ml of toluene, and AMBERLYST (registered trademark) 15 hydrogen form dry (15.0 g) was added thereto, followed by reflux for 2 hours. The reaction solution was separated by filtration, and the filtrate was concentrated and then recrystallized from toluene/methanol, followed by purification by column chromatography (toluene), thereby obtaining an intermediate 4a (2.35 g, 6.84 mmol, 36% yield for 2 steps) as a target substance in the form of white solid.

$^1$H-NMR (CDCl$_3$, 400 MHz) δ: 8.63 (s, 2H), 8.31 (d, J=0.8 Hz, 2H), 7.46 (m, 4H).

—Synthesis of intermediate 5a—

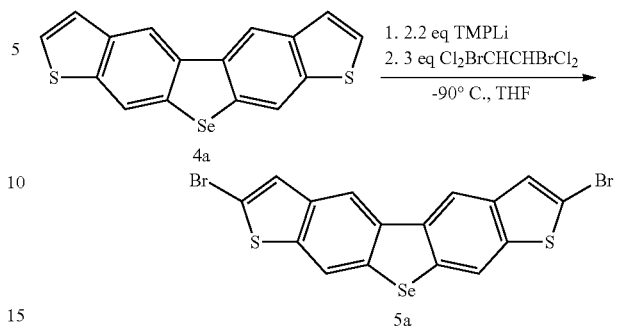

The intermediate 4a (2.00 g, 5.83 mmol) and 58 ml of tetrahydrofuran were stirred at −90° C. At this point in time, 20 ml of a tetrahydrofuran solution of lithium tetramethyl piperidine (12.8 mmol) was added dropwise thereto, followed by stirring for 30 minutes. A solution obtained by dissolving dibromotetrachloroethane (5.69 g, 17.5 mmol) in 20 ml of tetrahydrofuran was added dropwise thereto, followed by stirring for 20 minutes at −78° C., and then the reaction solution was heated to room temperature. The reaction solution was quenched with water and subjected to extraction using dichloroethane, and then the extract was dried over magnesium sulfate. After concentration, the extract was recrystallized from tetrahydrofuran/methanol, thereby obtaining an intermediate 5a (2.21 g, 4.41 mmol, 76% yield) as a target substance in the form of white solid.

$^1$H-NMR (CDCl$_3$, 400 MHz) δ: 8.46 (s, 2H), 8.16 (s, 2H), 7.45 (s, 2H).

—Synthesis of Compound 2—

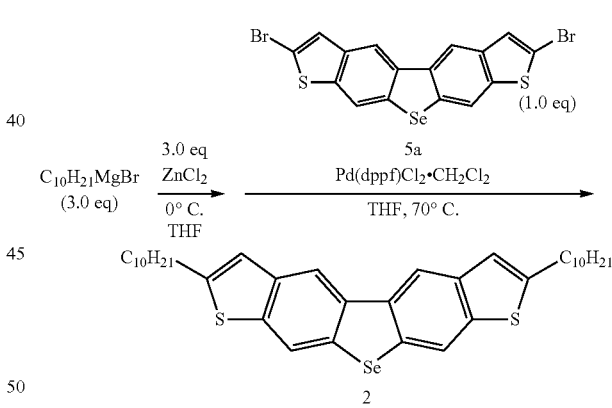

A zinc (II) chloride solution (1.0 mol/L tetrahydrofuran solution, 1.50 ml) was added to a n-decyl magnesium bromide solution (1.0 mol/L in diethylether, 1.50 ml, 1.50 mmol) used as a reactant at 0° C., followed by stirring for 15 minutes. Then, intermediate 5a (250 mg, 0.45 mmol) and a 1,1-bis(diphenylphosphino)ferrocene dichloropalladium (ID/dichloroethane adduct (20.2 mg, 0.025 mmol) were added thereto. The reaction solution was stirred for 1 hour at 70° C., followed by concentration and purification by column chromatography (hexane/chloroform=95/5), thereby obtaining a compound 2 (102 mg, 0.16 mmol, 33% yield) as a target substance in the form of white solid.

$^1$H NMR (CDCl$_3$, 400 MHz) δ: 8.43 (s, 2H), 8.17 (s, 2H), 7.10 (s, 2H), 2.93 (t, J=7.6 Hz, 4H), 1.78 (quint, J=6.4 Hz, 4H), 1.46-1.27 (m, 28H), 0.88 (t, J=6.8 Hz, 6H).

(Synthesis of Compound 3)

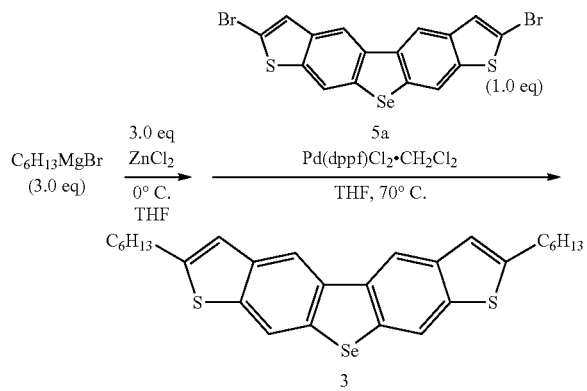

A compound 3 as a white solid was obtained in the same manner as used for synthesizing the compound 2, except that, as a reactant, a n-hexylmagnesium bromide solution was used instead of n-decylmagnesium bromide.

$^1$H-NMR (CDCl$_3$, 400 MHz) δ: 8.43 (s, 2H), 8.17 (s, 2H), 7.11 (s, 2H), 2.93 (t, J=7.2 Hz, 4H), 1.79 (quint, J=7.6 Hz, 4H), 1.43-1.40 (m, 4H), 1.40-1.26 (m, 4H), 0.91 (t, J=6.8 Hz, 6H).

(Synthesis of Compound 4)

—Synthesis of Intermediate 1b—

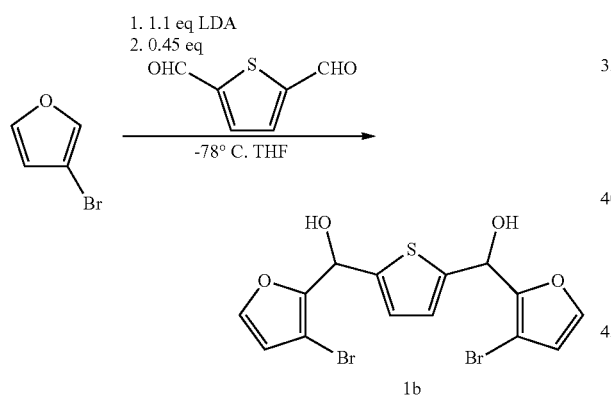

2-Bromofuran (14.0 g, 95.3 mmol) was dissolved in 30 ml of tetrahydrofuran and cooled to −78° C. Thereafter, a lithium diisopropylamide (1.5 mol/L tetrahydrofuran/ethylbenzene/heptane, 69.9 ml, 104.8 mmol) solution was added dropwise thereto, followed by stirring for 30 minutes, and then 70 ml of a tetrahydrofuran solution containing 2,5-thiophene dicarboxaldehyde (6.01 g, 42.9 mmol) was added dropwise thereto. After being stirred for 20 minutes, the reaction solution was heated to room temperature and quenched with water. Then, the reaction solution was subjected to extraction by using diethylether, and the extract was dried over magnesium sulfate and then concentrated, thereby obtaining an intermediate 1b (19.6 g) as a target substance in the form of brown oil. The obtained crude target substance was used for the next reaction without being further purified. $^1$H-NMR (CDCl$_3$, 400 MHz) δ: 7.39 (d, J=1.6 Hz, 2H), 6.82 (d, J=1.6 Hz, 2H), 6.44 (d, J=1.6 Hz, 2H), 6.11 (s, 2H).

—Synthesis of Intermediate 2b—

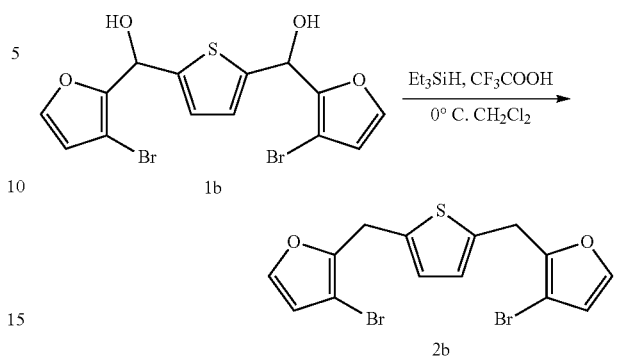

500 ml of a dichloroethane solution containing the intermediate 1b (19.6 g) and triethylsilane (32.0 ml, 200 mmol) was cooled to 0° C. At this point in time, trifluoroacetic acid (15.3 ml, 200 mmol) was added dropwise thereto, followed by stirring for 30 minutes. The reaction solution was quenched with water and subjected to extraction by using ethyl acetate, and the extract was dried over magnesium sulfate. After concentration, the extract was purified by column chromatography (hexane/chloroform=9/1), thereby obtaining an intermediate 2b (3.67 g, 9.13 mmol, 23% yield for 2 steps) as a target substance in the form of yellow oil.

$^1$H-NMR (CDCl$_3$, 400 MHz) δ: 7.28 (d, J=1.6 Hz, 2H), 6.66 (s, 2H), 6.36 (d, J=1.6 Hz, 2H), 4.08 (s, 4H).

—Synthesis of Intermediate 3b—

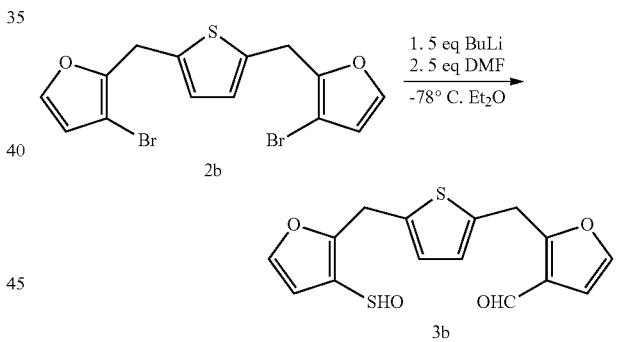

A n-butyllithium solution (1.6 mol/L heptane solution, 20.9 ml, 32.3 mmol) was diluted with 81.9 ml of diethylether and cooled to −78° C. At this point in time, a solution obtained by dissolving the intermediate 2b (2.60 g, 6.47 mmol) in 81.9 ml of diethylehter was added dropwise thereto, followed by stirring for 30 minutes. Thereafter, N,N-dimethylformamide (2.50 ml, 32.3 mmol) was added dropwise thereto, followed by stirring for 20 minutes, and then heated to room temperature. The reaction solution was quenched with water and subjected to extraction by using diethylether, and then the extract was dried over magnesium sulfate and concentrated, thereby obtaining the intermediate 3b (3.05 g) as a target substance in the form of red oil. The obtained crude target substance was used for the next reaction without being further purified.

$^1$H-NMR (CDCl$_3$, 400 MHz) δ: 9.94 (s, 2H), 7.34 (d, J=2.4 Hz, 2H), 6.72 (s, 2H), 6.71 (d, J=2.4 Hz, 2H), 4.40 (s, 4H).

—Synthesis of Intermediate 4b—

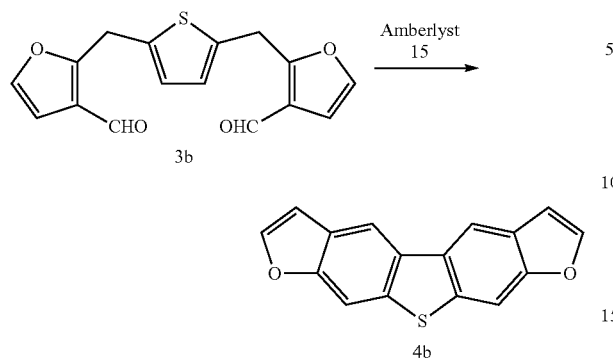

The intermediate 3b (3.05 g) was dissolved in 115 ml of toluene, and AMBERLYST (registered trademark) 15 hydrogen form dry (4.97 g) was added thereto, followed by reflux for 2 hours. The reaction solution was separated by filtration, and the filtrate was concentrated and then recrystallized from dichloroethane/acetonitrile, thereby obtaining an intermediate 4b (634 mg, 2.40 mmol, 37% yield for 2 steps) as a target substance in the form of white solid. $^1$H-NMR (CDCl$_3$, 400 MHz) δ: 8.33 (s, 2H), 7.90 (d, J=0.8 Hz, 2H), 6.67 (d, J=0.8 Hz, 2H), 6.90 (m, 2H).

—Synthesis of Intermediate 5b—

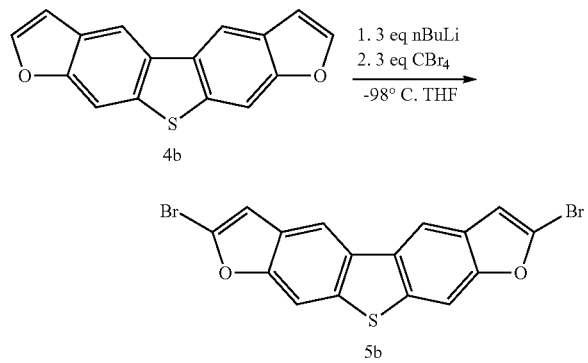

The intermediate 4b (450 mg, 1.7 mmol) and 25 ml of tetrahydrofuran were stirred at −90° C. At this point in time, n-butyllithium (1.6 mol/L heptane solution, 3.19 ml) was added dropwise thereto, followed by stirring for 30 minutes. 10 ml of a tetrahydrofuran solution containing carbon tetrabromide (2.26 g, 6.80 mmol) was added dropwise thereto, followed by stirring for 20 minutes at −78° C., and then heated to room temperature. The reaction solution was quenched with water and subjected to extraction by using dichloroethane, and the extract was dried over magnesium sulfate. After concentration, the extract was recrystallized from dichloroethane/ethyl acetate, thereby obtaining an intermediate 5b (558 mg, 1.32 mmol, 78% yield) as a target substance in the form of white solid.

$^1$H-NMR (CDCl$_3$, 400 MHz) δ: 8.23 (d, J=1.6 Hz, 2H), 7.87 (d, J=1.6 Hz, 2H), 6.87 (d, J=0.8 Hz, 2H).

—Synthesis of Compound 4—

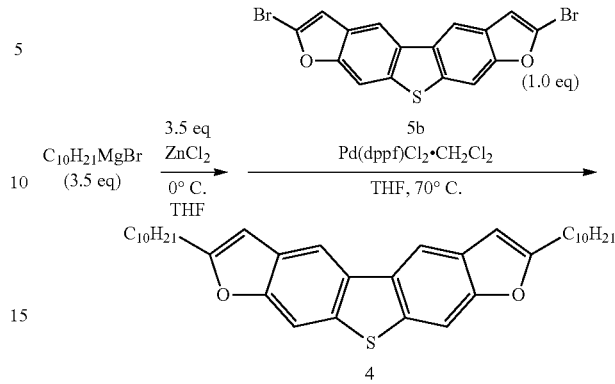

A compound 4 was obtained in the same manner as used for obtaining compound 2, except that the intermediate 5b was used as a raw material instead of the intermediate 5a. $^1$H-NMR (CDCl$_3$, 400 MHz) δ: 8.19 (s, 2H), 7.79 (s, 2H), 6.50 (s, 2H), 2.80 (t, J=7.2 Hz, 4H), 1.78 (quint, J=7.2 Hz, 4H), 1.45-1.20 (m, 28H), 0.87 (t, J=8.0 Hz, 6H).

(Synthesis of Compound 5)

A compound 5 was obtained in the same manner as used for obtaining the compound 4, except that n-hexyl magnesium bromide was used as a reactant instead of n-decyl magnesium bromide.

$^1$H-NMR (CDCl$_3$, 400 MHz) δ: 8.19 (s, 2H), 7.80 (s, 2H), 6.50 (s, 2H), 2.80 (t, J=7.4 Hz, 4H), 1.78 (quint, J=7.6 Hz, 4H), 1.45-1.25 (m, 12H), 0.90 (t, J=7.2 Hz, 6H).

(Synthesis of Compound 6)

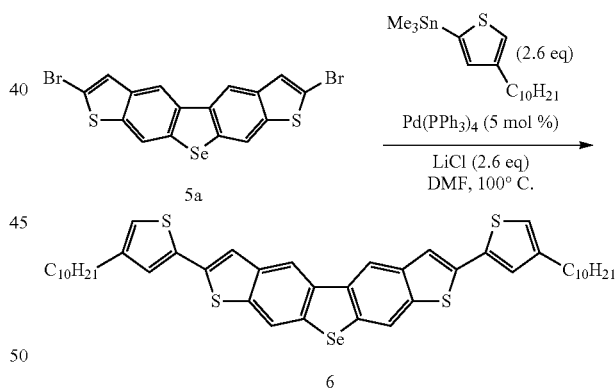

4 ml of N,N-dimethylformamide was added to the intermediate 5a (200 mg, 0.40 mmol), and a lithium chloride solution (0.5 mol/L tetrahydrofuran solution, 2.0 ml, 2.6 mmol) and tetrakistriphenylphosphine palladium (0) (23 mg, 0.020 mmol) were added thereto, followed by stirring for 3 hours at 100° C. Then, the reaction solution was concentrated and purified by column chromatography (chloroform) and recrystallization (toluene), thereby obtaining a compound 6 (205 mg, 0.26 mmol, 65% yield) as a target substance in the form of white solid. $^1$H-NMR (tetrachloroethane-d$_2$, 400 MHz) δ: 8.46 (s, 2H), 8.18 (s, 2H), 7.47 (s, 4H), 7.16 (s, 2H), 6.92 (s, 2H), 2.63 (t, J=7.2 Hz, 4H), 1.69-1.67 (m, 4H), 1.45-1.30 (m, 28H), 0.89 (t, J=6.0 Hz, 6H).

(Synthesis of Compound 7)

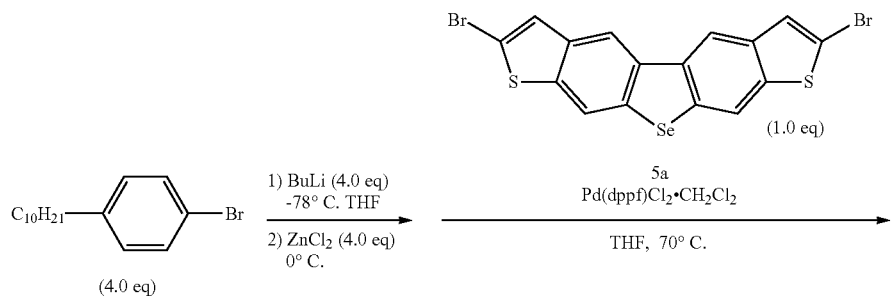

4-n-Decylphenyl bromide (475 mg, 1.6 mmol) and 1.0 ml of tetrahydrofuran were cooled to −78° C., and a n-butyllithium solution (2.6 mol/L hexane solution, 0.61 ml, 1.6 mmol) was added dropwise thereto, followed by stirring for 15 minutes. Then, a zinc (II) chloride solution (1.0 mol/L tetrahydrofuran solution, 1.60 ml) was added thereto, followed by stirring for 15 minutes at 0° C. To the reaction solution, the intermediate 5a (200 mg, 0.40 mmol), a 1,1-bis(diphenylphosphino)ferrocene dichloropalladium (II)/dichloroethane adduct (16.3 mg, 0.020 mmol) was added, followed by stirring for 1 hour at 70° C. After being concentrated, the reaction solution was subjected to column chromatography (chloroform) and then recrystallized (tetrahydrofuran), thereby obtaining a compound 7 (150 mg, 0.20 mmol, 50% yield) as a target substance in the form of white solid.

$^1$H-NMR (tetrachloroethane-d$_2$, 400 MHz) δ: 8.52 (s, 2H), 8.23 (s, 2H), 7.64 (d, J=8.4 Hz, 4H), 7.61 (s, 2H), 7.25 (d, J=8.0 Hz, 4H), 2.66 (t, J=7.4 Hz, 4H), 1.71-1.65 (m, 4H), 1.45-1.29 (m, 28H), 0.89 (t, J=6.0 Hz, 6H).

(Synthesis of Compound 8)

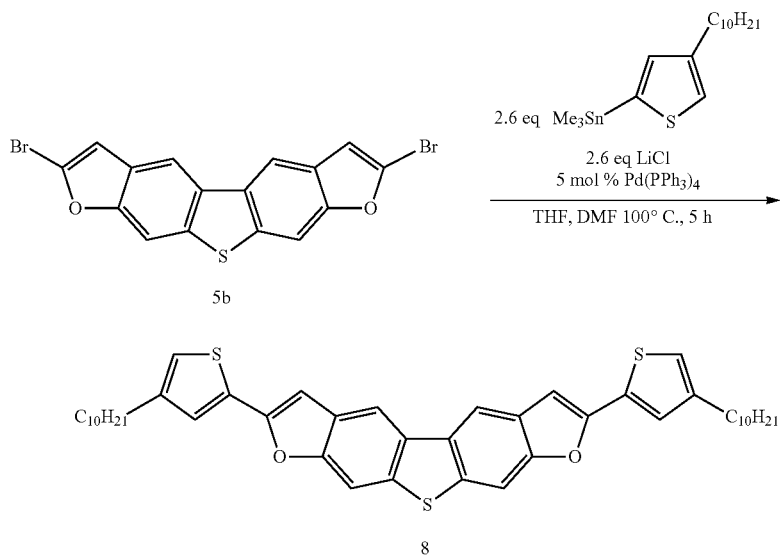

A compound 8 was obtained in the same manner as used for obtaining the compound 6, except that the intermediate 5b was used instead of the intermediate 5a.

$^1$H-NMR (tetrachloroethane-d$_2$, 400 MHz) δ: 8.24 (s, 2H), 7.87 (s, 2H), 7.75 (d, J=8.0 Hz, 4H), 7.22 (d, J=8.0 Hz, 4H), 7.04 (s, 2H), 2.59 (t, J=8.0 Hz, 4H), 1.59 (quint, J=6.5 Hz, 4H), 1.35-1.14 (m, 28H), 0.81 (t, J=7.2 Hz, 6H).

(Synthesis of Compound 9)

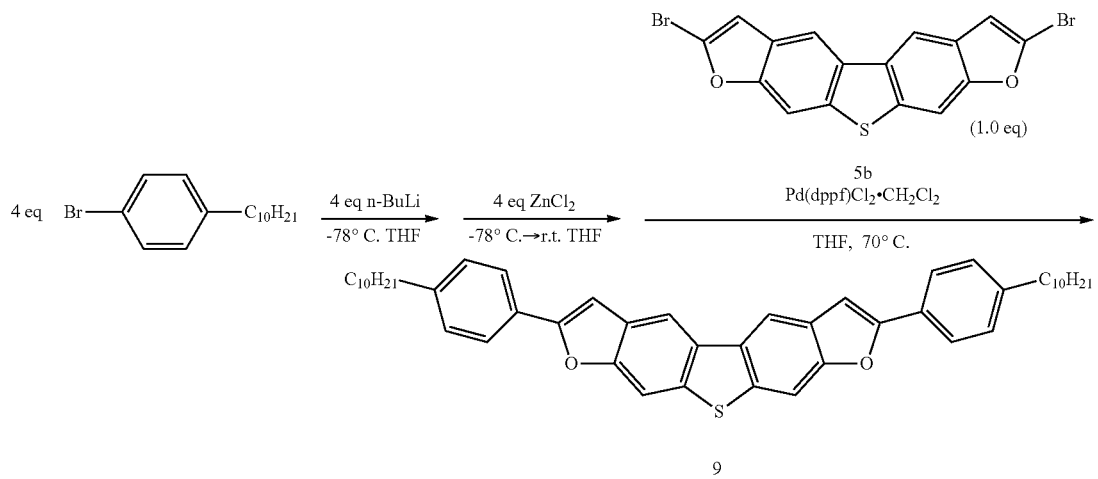

A compound 9 was obtained in the same manner as used for obtaining the compound 7, except that the intermediate 5b was used instead of the intermediate 5a.

$^1$H-NMR (tetrachloroethane-$d_2$, 400 MHz) δ: 8.26 (s, 2H), 7.87 (s, 2H), 7.38 (s, 2H), 6.96 (s, 4H), 2.65 (t, J=8.0 Hz, 4H), 1.68 (quint, J=7.4 Hz, 4H), 1.41-1.20 (m, 28H), 0.88 (t, J=7.2 Hz, 6H).

(Synthesis of Compound 10)
—Synthesis of Intermediate 1c—

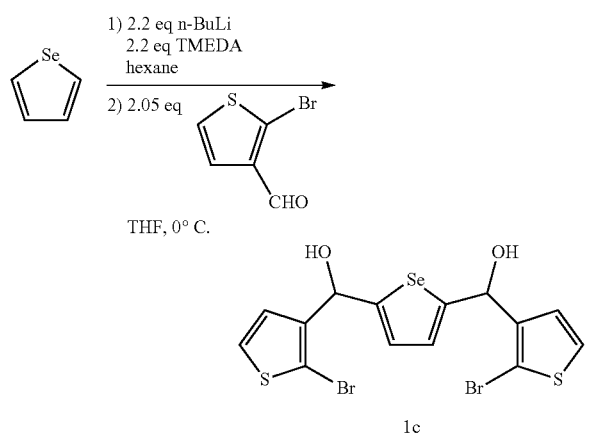

115 ml of a hexane solution containing tetramethyl piperidine (7.7 ml, 51.6 mmol) was cooled to 0° C. At this point in time, n-butyllithium (1.6 mol/L hexane solution, 32 ml, 51.6 mmol) was added dropwise thereto, followed by stirring for 30 minutes. Thereafter, selenophenone (3.30 g, 25.2 mmol) was added dropwise thereto, followed by stirring for 1 hour at 0° C. Then, 115 ml of a tetrahydrofuran solution containing 2-bromo-3-thiophene carboxaldehyde (10.1 g, 52.9 mmol) was added dropwise thereto, followed by stirring for 20 minutes, and the reaction solution was heated to room temperature. The reaction solution was quenched with water and then subjected to extraction by using ethyl acetate, and an organic layer was dried over magnesium sulfate and concentrated, thereby obtaining an intermediate 1c (12.0 g) as a target substance in the form of brown oil. The obtained crude target substance was used for the next reaction without being further purified.

—Synthesis of Intermediate 2c—

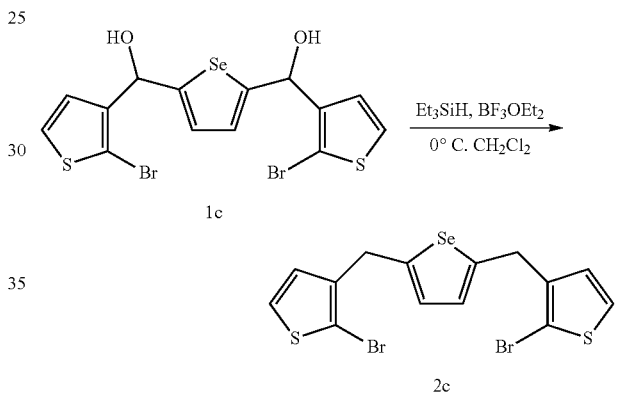

An intermediate 2c was obtained in the same manner as used for obtaining the intermediate 2a, except that the intermediate 1c was used instead of the intermediate 1a.
$^1$H-NMR (CDCl$_3$, 400 MHz) δ: 7.22 (d, J=4.8 Hz, 2H), 7.05 (d, J=5.2 Hz, 2H), 6.82 (d, J=5.2 Hz, 2H), 6.72-6.70 (m, 2H), 4.08 (s, 2H).

—Synthesis of Intermediate 3c—

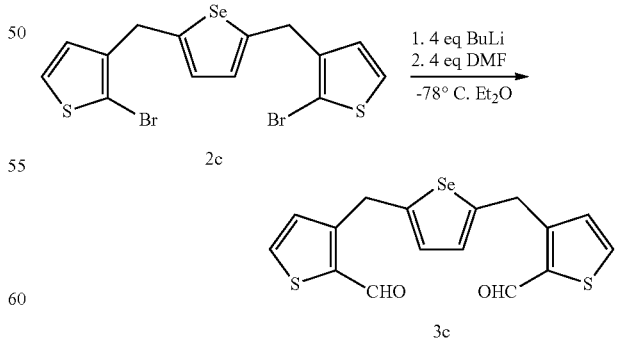

An intermediate 3c was obtained in the same manner as used for obtaining the intermediate 3a, except that the intermediate 2c was used instead of the intermediate 2a. The obtained crude target substance was used for the next reaction without being further purified.

—Synthesis of Intermediate 4c—

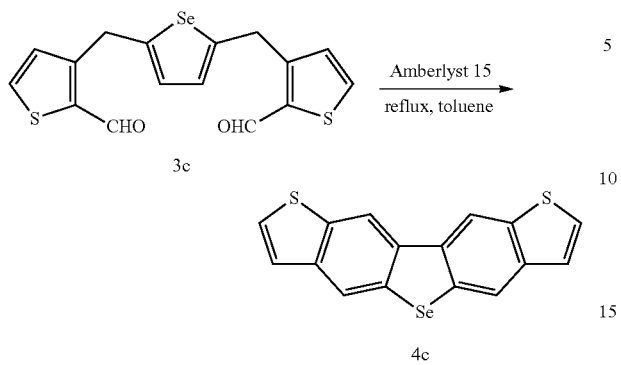

3c

4c

An intermediate 4c was obtained in the same manner as used for obtaining the intermediate 4a, except that the intermediate 3c was used instead of the intermediate 3a. $^1$H-NMR (CDCl$_3$, 400 MHz) δ: 8.67 (s, 2H), 8.26 (s, 2H), 7.53 (d, J=5.6 Hz, 2H), 7.37 (d, J=5.6 Hz, 2H).

—Synthesis of Intermediate 5c—

4c

5c

An intermediate 5c was obtained in the same manner as used for obtaining the intermediate 5a, except that the intermediate 4c was used instead of the intermediate 4a. $^1$H-NMR (CDCl$_3$, 400 MHz) δ: 8.47 (s, 2H), 8.13 (s, 2H), 7.36 (s, 2H).

—Synthesis of Compound 10—

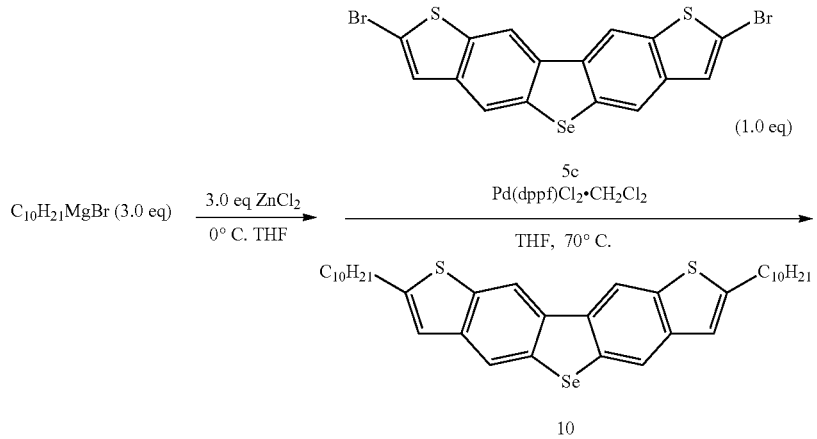

10

A compound 10 was obtained in the same manner as used for obtaining the compound 2, except that the intermediate 5c was used instead of the intermediate 5a.
$^1$H-NMR (CDCl$_3$, 400 MHz) δ: 8.50 (s, 2H), 8.07 (s, 2H), 7.01 (s, 2H), 2.94 (t, J=7.6 Hz, 4H), 1.82-1.74 (m, 4H), 1.42-1.27 (m, 28H), 0.88 (t, J=6.8 Hz, 6H).

(Synthesis of Compound 11)

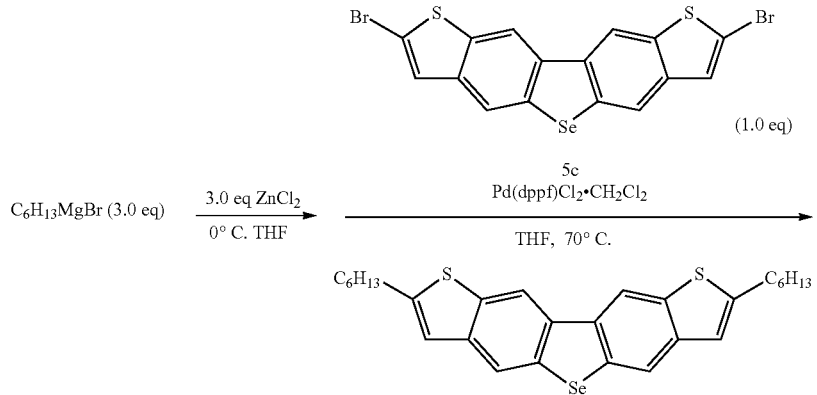

A compound 11 was obtained in the same manner as used for obtaining the compound 3, except that the intermediate 5c was used instead of the intermediate 5a. $^1$H-NMR (CDCl$_3$, 400 MHz) δ: 8.50 (s, 2H), 8.07 (s, 2H), 7.01 (s, 2H), 2.94 (t, J=7.6 Hz, 4H), 1.82-1.74 (m, 4H), 1.43-1.32 (m, 12H), 0.90 (t, J=6.4 Hz, 6H).

(Synthesis of Compound 12)

—Synthesis of Intermediate 5d—

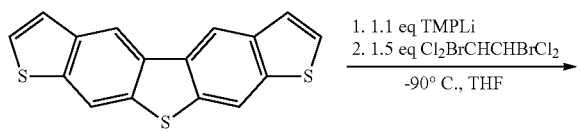

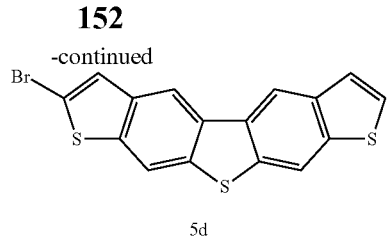

5d

An intermediate 5d was obtained in the same manner as used for obtaining the intermediate 1, except that the equivalents of an organic lithium reagent and the equivalents of dibromotetrachloroethane were reduced to 1.1 equivalents and 1.5 equivalents respectively.

—Synthesis of Intermediate 6d—

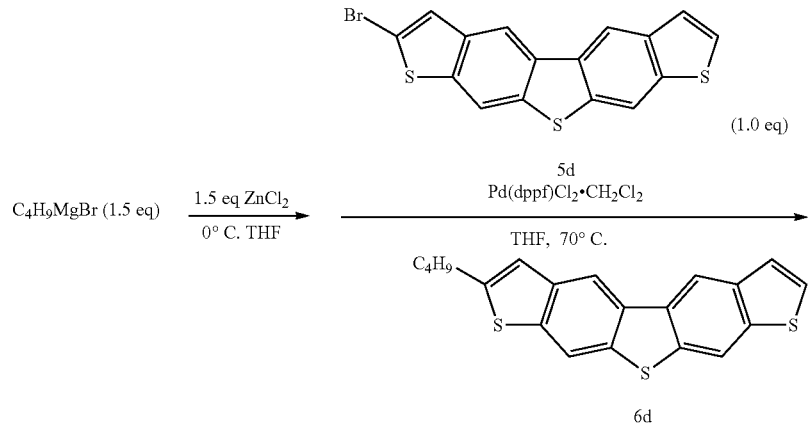

An intermediate 6d was obtained in the same manner as used for obtaining the compound 2, except that the intermediate 5d was used instead of the intermediate 5a such that the equivalents of an organic zinc reagent and a palladium catalyst halved.

—Synthesis of Intermediate 7d—

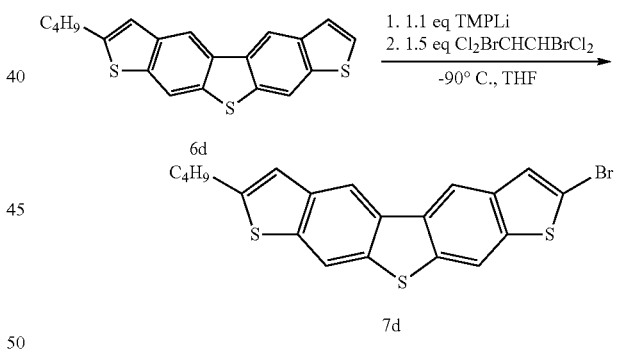

An intermediate 7d was obtained in the same manner as used for obtaining the intermediate 5d, except that the intermediate 6d was used instead of the material of the intermediate 5d.

—Synthesis of Compound 12—

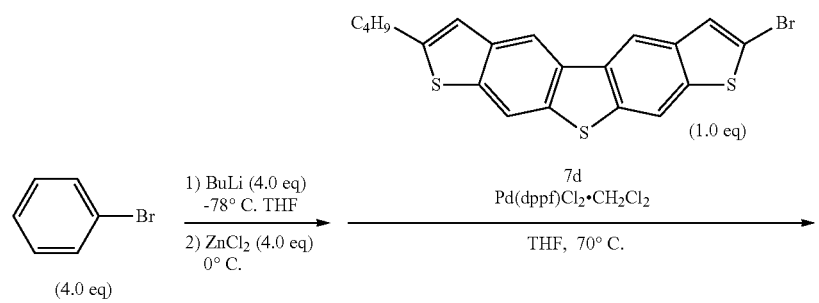

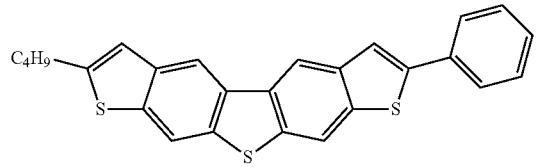

12

A compound 12 was obtained in the same manner as used for obtaining the compound 7, except that the intermediate 7d was used as a raw material instead of the intermediate 5a, and bromobenzene was used as a reactant instead of 4-n-decylphenyl bromide. Through mass spectrometry, it was confirmed that the obtained the compound 12 was a target compound. APCI-MS m/z; 429.0760 (M+1)

A comparative compound 1 having the following structure was synthesized according to the synthesis method described in J. Org. Chem. 2005, 70, 4502.

Comparative Compound 1

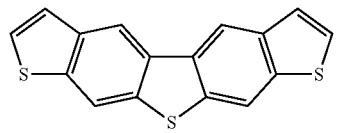 [SMILES: c1cc2cc3c(cc2s1)sc1cc2sccc2cc13]

The following comparative compounds 2 to 4 were synthesized with reference to JP2013-235903A, CN102206225A, and WO2011/126225A respectively. The comparative compounds 2 and 3 were measured by gel permeation chromatography (GPC), and as a result, it was confirmed that they have a weight-average molecular weight (Mw) of 40,000. The comparative compound 4 is a compound 49 described in WO2011/126225A.

The comparative compound 5 was synthesized with reference to Tetrahedron 66 (2010) 8778-8784.

Comparative compound 2

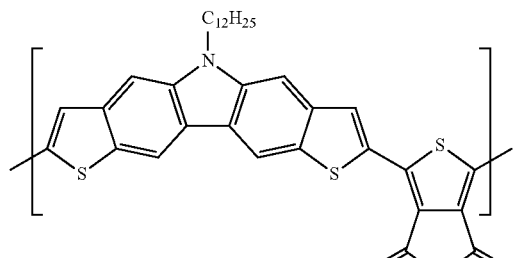

Comparative compound 3

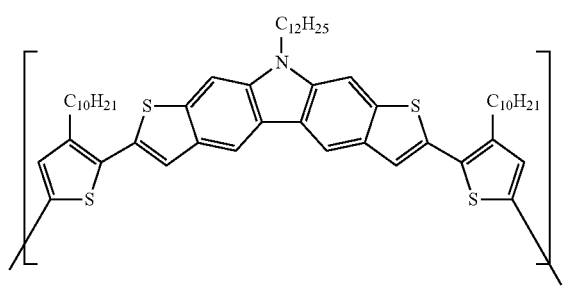

Comparative compound 4

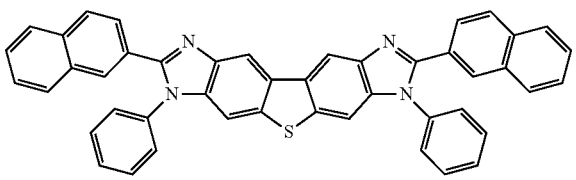

Comparative compound 5

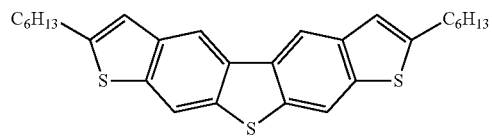

<Preparation/Evaluation of Element>

Through high-performance liquid chromatography, it was confirmed that the materials used for preparing elements had purity (area ratio for absorption intensity at 254 nm) of equal to or higher than 99.0%.

<Formation of Semiconductor Active Layer (Organic Semiconductor Layer) by Using Compound Alone>

Each of the aforementioned compounds 1 to 12 and comparative compounds 1 to 5 was prepared into a 0.1% by mass solution by using anisole as a solvent and then heated to 50° C. The solution was used as a coating solution for an organic semiconductor device.

In Examples 1 to 12 and Comparative Examples 1 to 5, an organic semiconductor film was formed by the method shown in FIGS. 4A to 4C. The details are as follows.

A 25 mm×25 mm substrate prepared by forming a thermally oxidized SiO$_2$ film having a thickness of 200 nm on the surface of an n-type silicon substrate (thickness: 0.4 mm) was used as a substrate A. The surface of the thermally oxidized film of the substrate A was cleaned with ultraviolet (UV)-ozone and then treated with β-phenethyltrimethoxysilane.

On the surface of the substrate A treated with β-phenethyltrimethoxysilane, a member B was placed on the central portion of the substrate A as shown in FIG. 4A such that the substrate A and the member B contacted each other. As the member B, a substance made of glass and having a size of 10 mm (length)×2 mm (width)×5 mm (height) was used. The transverse direction (X-axis direction) in FIG. 4A is the width direction of the member B; the vertical direction (Z-axis direction) in FIG. 4A is the height direction of the member B; and the vertical direction (Y-axis direction) in FIG. 4B2 is the longitudinal direction of the member B.

The substrate was heated to 50° C., and one drop (about 0.05 ml) of the coating solution prepared by the method described above was placed onto the substrate by using a pipette from the lateral side of the member B such that the drop contacted both of the substrate A and the member B as shown in FIG. 4A. As a result, as shown in FIGS. 4B1 and 4B2, the coating solution was dropped onto a portion within the surface of the substrate A. In the interface between the coating solution and the substrate B, a concave meniscus was formed.

As shown in FIG. 4C, in a state where the substrate A and the member B were caused to remain in contact with each other, and the positional relationship between the substrate A and the member B were maintained, the coating solution was air-dried. Then, the coating solution was dried under reduced pressure for 8 hours at 60° C. at a pressure of $10^{-3}$ MPa such that crystals of any one of the compounds 1 to 12 and the comparative compounds 1 to 5 were precipitated, thereby forming an organic semiconductor film. Whether or not crystals were precipitated was checked by observation using a polarizing microscope.

The obtained organic semiconductor film was used as a semiconductor active layer and covered with a mask. Then, F4-TCNQ with a thickness of 1 nm as a charge injection acceptor and a gold electrode with a thickness of 40 nm were vapor-deposited thereon, thereby obtaining an organic transistor element for measuring FET characteristics. The obtained organic transistor element was used as organic transistor elements (hereinafter, referred to as elements 1 to 12 and comparative elements 1 to 5 as well) of Examples 1 to 12 and Comparative Examples 1 to 5.

<Evaluation>

By using a semiconductor parameter analyzer (4156C manufactured by Agilent Technologies) connected to a semi-automatic prober (AX-2000 manufactured by Vector Semiconductor Co., Ltd.), the FET characteristics of the organic transistor elements of Examples 1 to 12 and Comparative Examples 1 to 5 were evaluated under a normal pressure/atmosphere.

The obtained results are shown in the following Table 36.

(a) Carrier Mobility

Between the source electrode and the drain electrode of each organic film transistor element (FET element), a voltage of −80 V was applied, and the gate voltage was varied within a range of 20 V to −100 V. In this way, a carrier mobility μ, was calculated using the following equation showing a drain current $I_d$.

$$I_d = (w/2L)\mu C_i (V_g - V_{th})^2$$

(In the equation, L represents a gate length, W represents a gate width, $C_i$ represents a capacity of the insulating layer per unit area, $V_g$ represents a gate voltage, and $V_{th}$ represents a threshold voltage.)

TABLE 36

| Element No. | Organic semiconductor material | Carrier mobility (cm$^2$/Vs) | Note |
|---|---|---|---|
| Element 1 | Compound 1 | 2.3 | Present invention |
| Element 2 | Compound 2 | 2.0 | Present invention |
| Element 3 | Compound 3 | 2.3 | Present invention |
| Element 4 | Compound 4 | 1.4 | Present invention |
| Element 5 | Compound 5 | 1.3 | Present invention |
| Element 6 | Compound 6 | 1.7 | Present invention |
| Element 7 | Compound 7 | 1.7 | Present invention |
| Element 8 | Compound 8 | 1.4 | Present invention |
| Element 9 | Compound 9 | 1.3 | Present invention |
| Element 10 | Compound 10 | 1.5 | Present invention |
| Element 11 | Compound 11 | 1.4 | Present invention |
| Element 12 | Compound 12 | 1.4 | Present invention |
| Comparative element 1 | Comparative compound 1 | 0.1 | Comparative Example |
| Comparative element 2 | Comparative compound 2 | 0.01 | Comparative Example |

TABLE 36-continued

| Element No. | Organic semiconductor material | Carrier mobility (cm$^2$/Vs) | Note |
|---|---|---|---|
| Comparative element 3 | Comparative compound 3 | 0.006 | Comparative Example |
| Comparative element 4 | Comparative compound 4 | 0.02 | Comparative Example |
| Comparative element 5 | Comparative compound 5 | 1.0 | Comparative Example |

From the above Table 36, it was understood that the organic transistor element of each of the examples using the compound of the present invention has high carrier mobility and can be preferably used as an organic semiconductor material.

In contrast, it was understood that the organic transistor elements in which the comparative compounds 1 to 5 not being included in the range of Formula (1) were used as organic semiconductor materials in the semiconductor active layer have low carrier mobility.

Examples 13 to 24 and Comparative Examples 6 to 8

<Preparation of Bottom Gate/Bottom Contact-Type Element>

In Examples 13 to 24 and Comparative Examples 6 to 8, a bottom gate/bottom contact-type organic transistor element was prepared. The details are described below.

An anisol solution containing 0.1% by mass of the compound 1 was heated to 100° C., and in a nitrogen atmosphere, the solution was cast onto a substrate for measuring FET characteristics heated to 90° C., thereby obtaining a non-light-emitting organic transistor element 2. As the substrate for measuring FET characteristics, a silicon substrate having a bottom gate/bottom contact structure was used which included chromium/gold (gate width W=100 mm, gate length L=100 μm) arranged to form a comb pattern as source and drain electrodes and included SiO$_2$ (film thickness: 200 nm) as an insulating layer. The obtained element 13 was taken as an organic transistor element of Example 13.

Elements 14 to 24 and comparative elements 6 to 8 were prepared in the same manner as used for preparing the element 13, except that any one of the compounds 2 to 12 or the comparative compounds 1, 2, or 5 was used instead of the compound 1. The obtained elements 14 to 24 and the comparative elements 6 to 8 were taken as organic transistor elements of Examples 14 to 24 and Comparative Examples 6 to 8.

<Evaluation>

For the elements 13 to 24 and the comparative elements 6 to 8, FET characteristics of an organic transistor element were evaluated in the same manner as in Example 1. The results are shown in the following Table 37.

TABLE 37

| Element No. | Organic semiconductor material | Carrier mobility (cm$^2$/Vs) | Note |
|---|---|---|---|
| Element 13 | Compound 1 | 0.56 | Present invention |
| Element 14 | Compound 2 | 0.50 | Present invention |
| Element 15 | Compound 3 | 0.50 | Present invention |
| Element 16 | Compound 4 | 0.45 | Present invention |
| Element 17 | Compound 5 | 0.45 | Present invention |
| Element 18 | Compound 6 | 0.55 | Present invention |
| Element 19 | Compound 7 | 0.50 | Present invention |
| Element 20 | Compound 8 | 0.48 | Present invention |

TABLE 37-continued

| Element No. | Organic semiconductor material | Carrier mobility (cm$^2$/Vs) | Note |
|---|---|---|---|
| Element 21 | Compound 9 | 0.42 | Present invention |
| Element 22 | Compound 10 | 0.48 | Present invention |
| Element 23 | Compound 11 | 0.45 | Present invention |
| Element 24 | Compound 12 | 0.50 | Present invention |
| Comparative element 6 | Comparative compound 1 | 0.03 | Comparative Example |
| Comparative element 7 | Comparative compound 2 | <0.001 | Comparative Example |
| Comparative element 8 | Comparative compound 5 | 0.3 | Comparative Example |

Examples 25 to 36 and Comparative Examples 9 to 11

<Preparation of Bottom Gate/Bottom Contact-Type Element Using Polymer Binder>

A bottom gate/bottom contact-type element 25 was prepared in the same manner as in Example 13, except that, in Example 13, a material (material 1') containing the compound 1 and poly α-methylstyrene at a mass ratio of 1:1 was used instead of the compound 1. The obtained element 25 was taken as an organic transistor element of Example 25.

Elements 26 to 36 and comparative elements 9 to 11 were prepared in the same manner as used for preparing the element 25, except that, in preparing the element 25, any one of the compounds 2 to 12 or the comparative compounds 1, 2, and 5 was used instead of the compound 1. The obtained elements 26 to 36 and comparative elements 9 to 11 were taken as organic transistor elements of Examples 26 to 36 and Comparative Examples 9 to 11. The materials containing each of the compounds 2 to 12 and poly α-methylstyrene at a mass ratio 1:1 were named to materials 2' to 12' respectively.

<Evaluation>

For the elements 25 to 36 and the comparative elements 9 to 11, FET characteristics of an organic transistor element were evaluated in the same manner as in Example 1. The results are shown in the following Table 38.

TABLE 38

| Element No. | Organic semiconductor material | Carrier mobility (cm$^2$/Vs) | Note |
|---|---|---|---|
| Element 25 | Material 1' | 0.90 | Present invention |
| Element 26 | Material 2' | 0.88 | Present invention |
| Element 27 | Material 3' | 0.90 | Present invention |
| Element 28 | Material 4' | 0.58 | Present invention |
| Element 29 | Material 5' | 0.52 | Present invention |
| Element 30 | Material 6' | 0.75 | Present invention |
| Element 31 | Material 7' | 0.70 | Present invention |
| Element 32 | Material 8' | 0.48 | Present invention |
| Element 33 | Material 9' | 0.45 | Present invention |
| Element 34 | Material 10' | 0.50 | Present invention |
| Element 35 | Material 11' | 0.45 | Present invention |
| Element 36 | Material 12' | 0.58 | Present invention |
| Comparative element 9 | Comparative compound 1 and poly α-methylsytrene | 0.02 | Comparative Example |
| Comparative element 10 | Comparative compound 2 and poly α-methylsytrene | <0.001 | Comparative Example |
| Comparative element 11 | Comparative compound 5 and poly α-methylsytrene | 0.21 | Comparative Example |

From the above Tables 37 and 38, it was understood that the organic transistor element of each example using the compound of the present invention exhibits high carrier mobility even in a case where the element is used in a bottom gate/bottom contact-type element and even in a case where a polymer binder is used, and that the organic transistor element can be preferably used as an organic semiconductor material.

In contrast, it was understood that the organic transistor element, in which the comparative compound 1, 2, or 5 not being included in the range of Formula (1) is used as an organic semiconductor material in a semiconductor active layer, exhibits low carrier mobility.

EXPLANATION OF REFERENCES

11: substrate
12: electrode
13: insulator layer
14: semiconductor active layer (organic substance layer, organic semiconductor layer)
15a, 15b: electrode
31: substrate
32: electrode
33: insulator layer
34a, 34b: electrode
35: semiconductor active layer (organic substance layer, organic semiconductor layer)
41: coating solution
42: substrate A
43: member B

What is claimed is:

1. An organic transistor comprising a semiconductor active layer containing a compound represented by the following Formula (2) and has a molecular weight of equal to or less than 3,000;

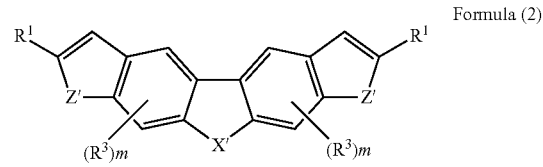

Formula (2)

in Formula (2),
each X' independently represents an oxygen atom, a sulfur atom, or a selenium atom;
each Z' is independently selected from NR$^7$, an oxygen atom, a sulfur atom, and a selenium atom;
a ring containing Z' is an aromatic heterocycle;
R$^1$ and the aromatic heterocycle containing Z' are optionally bonded to each other through the following group A of divalent linking groups;
R$^3$ and a benzene ring are optionally bonded to each other through the following group A of divalent linking groups;
the group A of divalent linking groups represents any one of divalent linking groups —O—, —S—, —NR$^8$—, —CO—, —SO—, and —SO$_2$— or represents a divalent linking group in which two or more of these divalent linking groups are bonded to each other;
R$^1$, R$^7$, and R$^8$ each independently represent a hydrogen atom, an alkyl group, an alkenyl group, an alkynyl group, an aryl group, or a heteroaryl group and optionally further have a substituent, and two or more $R^1$s are the same as or different from each other;

each $R^3$ independently represents an alkyl group, an alkenyl group, an alkynyl group, an aryl group, or a heteroaryl group and optionally further have a substituent, and in a case where m is 2, $R^3$s are the same as or different from each other;

each m is independently an integer of 0 to 2;

here, a case where both Z' are $NR^7$ is excluded;

in a case where X', Z', and $R^1$ in Formula (2) are a sulfur atom, a sulfur atom, and an alkyl group respectively, $R^1$ and the aromatic heterocycle containing Z' are bonded to each other through the group A of divalent linking groups; and a case where $R^1$ is a hydrogen atom and each m is 0 is excluded.

2. The organic transistor according to claim 1, wherein in Formula (2), each of the aromatic heterocycles containing Z' is independently any one of a thiophene ring, a furan ring, and a pyrrole ring.

3. The organic transistor according to claim 1, wherein in Formula (2), the number of carbon atoms contained in $R^1$, and $R^3$ is equal to or less than 30.

4. The organic transistor according to claim 1, wherein in Formula (2), both m are 0.

5. The organic transistor according to claim 1, wherein in Formula (2), each of $R^1$ independently an alkyl group having 20 or less carbon atoms, an aryl group having 20 or less carbon atoms, or a heteroaryl group having 20 or less carbon atoms.

6. The organic transistor according to claim 1, wherein in Formula (2), $R^1$ are the same as each other, $R^3$ are the same as each other, and m are the same as each other.

7. The organic transistor according to claim 1, wherein the compound which is represented by Formula (2) is a compound which is represented by the following Formula (4);

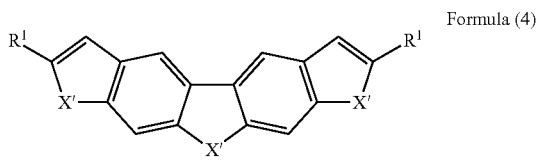

in Formula (4), each X' independently represents an oxygen atom, a sulfur atom, or a selenium atom;

$R^1$ and an aromatic heterocycle containing X' are optionally bonded to each other through the following group A of divalent linking groups;

the group A of divalent linking groups represents any one of divalent linking groups —O—, —S—, —$NR^8$—, —CO—, —SO—, and —$SO_2$— or represents a divalent linking group in which two or more of these divalent linking groups are bonded to each other; and each $R^1$ independently represents an alkyl group, an alkenyl group, an alkynyl group, an aryl group, or a heteroaryl group and optionally further have a substituent, each $R^8$ independently represents a hydrogen atom, an alkyl group, an alkenyl group, an alkynyl group, an aryl group, or a heteroaryl group and optionally further have a substituent, and two or more $R^1$s are the same as or different from each other.

8. The organic transistor according to claim 7, wherein in Formula (4), $R^1$ is an aryl group optionally substituted with a linear aliphatic hydrocarbon group or a heteroaryl group optionally substituted with a linear aliphatic hydrocarbon group.

9. A compound which is represented by the following Formula (2) and has a molecular weight of equal to or less than 3,000;

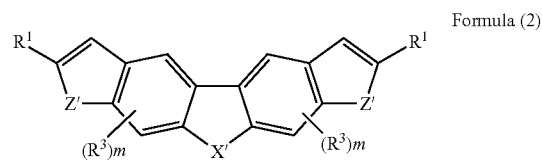

in Formula (2), each X' independently represents an oxygen atom, a sulfur atom, or a selenium atom;

each Z' is independently selected from $NR^7$, an oxygen atom, a sulfur atom, and a selenium atom;

a ring containing Z' is an aromatic heterocycle;

$R^1$ and the aromatic heterocycle containing Z' are optionally bonded to each other through the following group A of divalent linking groups;

$R^3$ and a benzene ring are optionally bonded to each other through the following group A of divalent linking groups;

the group A of divalent linking groups represents any one of divalent linking groups —O—, —S—, —$NR^8$—, —CO—, —SO—, and —$SO_2$— or represents a divalent linking group in which two or more of these divalent linking groups are bonded to each other;

$R^1$, $R^7$, and $R^8$ each independently represent a hydrogen atom, an alkyl group, an alkenyl group, an alkynyl group, an aryl group, or a heteroaryl group and optionally further have a substituent, and two or more $R^1$s are the same as or different from each other;

each $R^3$ independently represents an alkyl group, an alkenyl group, an alkynyl group, an aryl group, or a heteroaryl group and optionally further have a substituent, and in a case where m is 2, $R^3$s are the same as or different from each other;

each m is independently an integer of 0 to 2;

here, a case where both Z' are $NR^7$ is excluded;

in a case where X', Z', and $R^1$ in Formula (2) are a sulfur atom, a sulfur atom, and an alkyl group respectively, $R^1$ and the aromatic heterocycle containing Z' are bonded to each other through the group A of divalent linking groups; and a case where $R^1$ is a hydrogen atom and each m is 0 is excluded.

10. The compound according to claim 9, wherein in Formula (2), each of the aromatic heterocycles containing Z' is independently any one of a thiophene ring, a furan ring, and a pyrrole ring.

11. The compound according to claim 9, wherein in Formula (2), the number of carbon atoms contained in $R^1$, and $R^3$ is equal to or less than 30.

12. The compound according to claim 9, wherein in Formula (2), both m are 0.

13. The compound according to claim 9, wherein in Formula (2), each of $R^1$ is independently an alkyl group having 20 or less carbon atoms, an aryl group having 20 or less carbon atoms, or a heteroaryl group having 20 or less carbon atoms.

14. The compound according to claim 9, wherein in Formula (2), $R^1$ are the same as each other, $R^3$ are the same as each other, and m and n are the same as each other.

15. The compound according to claim 9, wherein the compound which is represented by Formula (2) is a compound which is represented by the following Formula (4);

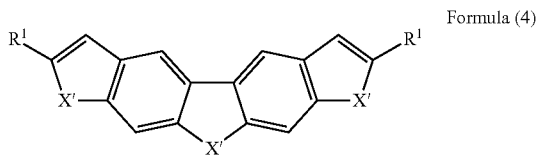

Formula (4)

in Formula (4), each X' independently represents an oxygen atom, a sulfur atom, or a selenium atom;

$R^1$ and an aromatic heterocycle containing X' are optionally bonded to each other through the following group A of divalent linking groups;

the group A of divalent linking groups represents any one of divalent linking groups —O—, —S—, —NR$^8$—, —CO—, —SO—, and —SO$_2$— or represents a divalent linking group in which two or more of these divalent linking groups are bonded to each other; and each $R^1$ independently represents an alkyl group, an alkenyl group, an alkynyl group, an aryl group, or a heteroaryl group and optionally further have a substituent, each $R^8$ independently represents a hydrogen atom, an alkyl group, an alkenyl group, an alkynyl group, an aryl group, or a heteroaryl group and optionally further have a substituent, and two or more $R^1$s are the same as or different from each other.

16. The compound according to claim 15, wherein in Formula (4), $R^1$ is an aryl group optionally substituted with a linear aliphatic hydrocarbon group or a heteroaryl group optionally substituted with a linear aliphatic hydrocarbon group.

17. An organic semiconductor material for a non-light-emitting organic semiconductor device containing the compound according to claim 1.

18. A material for an organic transistor containing the compound according to claim 1.

19. A coating solution for a non-light-emitting organic semiconductor device containing the compound according to claim 1.

20. A method for manufacturing an organic transistor, comprising:

preparing a semiconductor active layer by coating a substrate with the coating solution for a non-light-emitting organic semiconductor device according to claim 19 and drying the coating solution.

21. A method for manufacturing an organic semiconductor film, wherein in a state where a distance between a substrate A and a member B not being fixed to the substrate A is kept constant or in a state where the substrate A and the member B are caused to remain in contact with each other, a coating solution prepared by dissolving the compound according to claim 1 in a solvent is dropped onto a portion within the surface of the substrate A such that the coating solution contacts both of the substrate A and the member B, and the dropped coating solution is slowly dried, such that crystals of the compound according to claim 1 are precipitated and a semiconductor active layer is formed;

here, as long as the distance between the substrate A and the member B is kept constant or as long as the substrate A and the member B are caused to remain in contact with each other, the positional relationship between the substrate A and the member B are optionally maintained or changed when the coating solution is dropped or dried.

22. An organic semiconductor film for a non-light-emitting organic semiconductor device containing the compound according to claim 1.

23. The organic semiconductor film for a non-light-emitting organic semiconductor device according to claim 22, further containing a polymer binder.

* * * * *